US008067386B2

(12) United States Patent
Bhanot et al.

(10) Patent No.: US 8,067,386 B2
(45) Date of Patent: Nov. 29, 2011

(54) MODULATION OF EIF4E-BP2 EXPRESSION

(75) Inventors: Sanjay Bhanot, Carlsbad, CA (US); Kenneth W. Dobie, Del Mar, CA (US); Ravi Jain, Fremont, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 12/274,030

(22) Filed: Nov. 19, 2008

(65) Prior Publication Data

US 2009/0082302 A1    Mar. 26, 2009

Related U.S. Application Data

(62) Division of application No. 11/042,899, filed on Jan. 24, 2005, now Pat. No. 7,468,431.

(60) Provisional application No. 60/538,752, filed on Jan. 22, 2004.

(51) Int. Cl.
| C07H 21/02 | (2006.01) |
| C07H 21/04 | (2006.01) |
| A61K 31/70 | (2006.01) |
| C12Q 1/68 | (2006.01) |
| C12N 5/00 | (2006.01) |

(52) U.S. Cl. ............ 514/44 A; 435/375; 536/23.1; 536/24.1; 536/24.5

(58) Field of Classification Search ............... None
See application file for complete search history.

(56) References Cited

U.S. PATENT DOCUMENTS

| 3,687,808 A | 8/1972 | Merigan et al. |
| 4,426,330 A | 1/1984 | Sears |
| 4,469,863 A | 9/1984 | Ts'o et al. |
| 4,476,301 A | 10/1984 | Imbach et al. |
| 4,534,899 A | 8/1985 | Sears |
| 4,587,044 A | 5/1986 | Miller et al. |
| 4,605,735 A | 8/1986 | Miyoshi et al. |
| 4,667,025 A | 5/1987 | Miyoshi et al. |
| 4,762,779 A | 8/1988 | Snitman |
| 4,789,737 A | 12/1988 | Miyoshi et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Huynh Dinh et al. |
| 4,876,335 A | 10/1989 | Yamane et al. |
| 4,904,582 A | 2/1990 | Tullis |
| 4,948,882 A | 8/1990 | Ruth et al. |
| 4,958,013 A | 9/1990 | Letsinger et al. |
| 4,981,957 A | 1/1991 | Lebleu et al. |
| 5,013,556 A | 5/1991 | Woddle et al. |
| 5,013,830 A | 5/1991 | Ohtsuka et al. |
| 5,023,243 A | 6/1991 | Tullis |
| 5,034,506 A | 7/1991 | Summerton et al. |
| 5,082,830 A | 1/1992 | Brakel et al. |
| 5,108,921 A | 4/1992 | Low et al. |
| 5,109,124 A | 4/1992 | Ramachandran et al. |
| 5,112,963 A | 5/1992 | Pieles et al. |
| 5,118,800 A | 6/1992 | Smith et al. |
| 5,118,802 A | 6/1992 | Smith et al. |
| 5,130,302 A | 7/1992 | Spielvogel et al. |
| 5,134,066 A | 7/1992 | Rogers et al. |
| 5,138,045 A | 8/1992 | Cook et al. |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,213,804 A | 5/1993 | Martin et al. |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,220,007 A | 6/1993 | Pederson et al. |
| 5,227,170 A | 7/1993 | Sullivan |
| 5,235,033 A | 8/1993 | Summerton et al. |
| 5,245,022 A | 9/1993 | Weis et al. |
| 5,254,469 A | 10/1993 | Warren, III et al. |
| 5,256,775 A | 10/1993 | Froehler |
| 5,258,506 A | 11/1993 | Urdea et al. |
| 5,262,536 A | 11/1993 | Hobbs, Jr. |
| 5,264,221 A | 11/1993 | Tagawa et al. |
| 5,264,423 A | 11/1993 | Cohen et al. |
| 5,264,562 A | 11/1993 | Matteucci |
| 5,264,564 A | 11/1993 | Matteucci |
| 5,272,250 A | 12/1993 | Spielvogel et al. |

(Continued)

FOREIGN PATENT DOCUMENTS

WO    WO 93/07883    4/1993

(Continued)

OTHER PUBLICATIONS

U.S. Appl. No. 09/315,298, filed May 20, 1999, Teng et al.
Bennett et al., "Antisense oligonucleotides as a tool for gene functionalization and target validation" Biochimica et Biophysica Acta (1999) 1489:19-30.
Branch et al., "A good antisense molecule is hard to find" TIBS (1998) 23:45-50.
Chiang et al., "Antisense Oligonucleotides Inhibit Intercellular Adhesion Molecule 1 Expression by Two Distinct Mechanisms" J. Biol. Chem. (1991) 266:18162-18171.
Chin, "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Crooke et al., "Basic Principles of Antisense Therapeutics" Antisense Research and Application (1998) Chapter 1:1-50.

(Continued)

Primary Examiner — Sean McGarry
(74) Attorney, Agent, or Firm — Isis Pharmaceuticals Patent Department Jones Day

(57) ABSTRACT

Compounds, compositions and methods are provided for modulating the expression of eIF4E-BP2. The compositions comprise oligonucleotides, targeted to nucleic acid encoding eIF4E-BP2. Methods of using these compounds for modulation of eIF4E-BP2 expression and for diagnosis and treatment of diseases and conditions associated with expression of eIF4E-BP2 are provided.

55 Claims, No Drawings

U.S. PATENT DOCUMENTS

| | | |
|---|---|---|
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,319,080 A | 6/1994 | Leumann |
| 5,321,131 A | 6/1994 | Agrawal et al. |
| 5,354,844 A | 10/1994 | Beug et al. |
| 5,356,633 A | 10/1994 | Woodle et al. |
| 5,359,044 A | 10/1994 | Cook et al. |
| 5,366,878 A | 11/1994 | Pederson et al. |
| 5,367,066 A | 11/1994 | Urdea et al. |
| 5,371,241 A | 12/1994 | Brush |
| 5,391,723 A | 2/1995 | Priest |
| 5,393,878 A | 2/1995 | Leumann |
| 5,395,619 A | 3/1995 | Zalipsky et al. |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,414,077 A | 5/1995 | Lin et al. |
| 5,416,016 A | 5/1995 | Low et al. |
| 5,416,203 A | 5/1995 | Letsinger |
| 5,417,978 A | 5/1995 | Tari et al. |
| 5,432,272 A | 7/1995 | Benner |
| 5,434,257 A | 7/1995 | Matteucci et al. |
| 5,446,137 A | 8/1995 | Maag et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,127 A | 10/1995 | Felgner et al. |
| 5,459,255 A | 10/1995 | Cook et al. |
| 5,462,854 A | 10/1995 | Coassin et al. |
| 5,466,677 A | 11/1995 | Baxter et al. |
| 5,466,786 A | 11/1995 | Buhr et al. |
| 5,469,854 A | 11/1995 | Unger et al. |
| 5,470,967 A | 11/1995 | Huie et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,491,133 A | 2/1996 | Walder et al. |
| 5,502,177 A | 3/1996 | Matteucci et al. |
| 5,510,475 A | 4/1996 | Agrawal et al. |
| 5,512,295 A | 4/1996 | Kornberg et al. |
| 5,512,439 A | 4/1996 | Hornes et al. |
| 5,512,667 A | 4/1996 | Reed et al. |
| 5,514,785 A | 5/1996 | Van Ness et al. |
| 5,519,126 A | 5/1996 | Hecht |
| 5,519,134 A | 5/1996 | Acevedo et al. |
| 5,521,291 A | 5/1996 | Curiel et al. |
| 5,525,465 A | 6/1996 | Haralambidis et al. |
| 5,525,711 A | 6/1996 | Hawkins et al. |
| 5,527,528 A | 6/1996 | Allen et al. |
| 5,527,899 A | 6/1996 | Froehler |
| 5,534,259 A | 7/1996 | Zalipsky et al. |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,541,313 A | 7/1996 | Ruth |
| 5,543,152 A | 8/1996 | Webb et al. |
| 5,543,158 A | 8/1996 | Gref et al. |
| 5,545,730 A | 8/1996 | Urdea et al. |
| 5,547,932 A | 8/1996 | Curiel et al. |
| 5,550,111 A | 8/1996 | Suhadolnik et al. |
| 5,552,538 A | 9/1996 | Urdea et al. |
| 5,552,540 A | 9/1996 | Haralambidis |
| 5,556,948 A | 9/1996 | Tagawa et al. |
| 5,561,225 A | 10/1996 | Maddry et al. |
| 5,563,253 A | 10/1996 | Agrawal et al. |
| 5,565,350 A | 10/1996 | Kmiec |
| 5,565,552 A | 10/1996 | Magda et al. |
| 5,565,555 A | 10/1996 | Froehler et al. |
| 5,567,810 A | 10/1996 | Weis et al. |
| 5,567,811 A | 10/1996 | Misiura et al. |
| 5,571,799 A | 11/1996 | Tkachuk et al. |
| 5,574,142 A | 11/1996 | Meyer, Jr. et al. |
| 5,576,427 A | 11/1996 | Cook et al. |
| 5,578,717 A | 11/1996 | Urdea et al. |
| 5,578,718 A | 11/1996 | Cook et al. |
| 5,580,575 A | 12/1996 | Unger et al. |
| 5,580,731 A | 12/1996 | Chang et al. |
| 5,583,020 A | 12/1996 | Sillivan |
| 5,585,481 A | 12/1996 | Arnold, Jr. et al. |
| 5,586,469 A | 12/1996 | Mitani et al. |
| 5,587,361 A | 12/1996 | Cook et al. |
| 5,587,371 A | 12/1996 | Sessler et al. |
| 5,591,584 A | 1/1997 | Chang et al. |
| 5,591,721 A | 1/1997 | Agrawal et al. |
| 5,591,722 A | 1/1997 | Montgomery et al. |
| 5,594,121 A | 1/1997 | Froehler et al. |
| 5,595,726 A | 1/1997 | Magda et al. |
| 5,595,756 A | 1/1997 | Bally et al. |
| 5,596,086 A | 1/1997 | Matteucci et al. |
| 5,596,091 A | 1/1997 | Switzer |
| 5,597,696 A | 1/1997 | Linn et al. |
| 5,597,909 A | 1/1997 | Urdea et al. |
| 5,599,923 A | 2/1997 | Sessler et al. |
| 5,599,928 A | 2/1997 | Hemmi et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci et al. |
| 5,652,355 A | 7/1997 | Metelev et al. |
| 5,652,356 A | 7/1997 | Agrawal |
| 5,658,873 A | 8/1997 | Bertsch-Frank et al. |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,688,941 A | 11/1997 | Cook et al. |
| 5,700,920 A | 12/1997 | Altmann et al. |
| 5,700,922 A | 12/1997 | Cook |
| 5,714,331 A | 2/1998 | Buchardt et al. |
| 5,719,262 A | 2/1998 | Buchardt et al. |
| 5,721,218 A | 2/1998 | Froehler |
| 5,763,588 A | 6/1998 | Matteucci et al. |
| 5,792,608 A | 8/1998 | Swaminathan et al. |
| 5,792,747 A | 8/1998 | Schally et al. |
| 5,830,653 A | 11/1998 | Froehler et al. |
| 5,874,231 A | 2/1999 | Sonenberg et al. |
| 5,998,148 A | 12/1999 | Bennett et al. |
| 6,005,096 A | 12/1999 | Matteucci et al. |
| 6,287,860 B1 | 9/2001 | Monia et al. |
| 6,361,940 B1 * | 3/2002 | Van Ness et al. ................ 435/6 |
| 6,365,345 B1 * | 4/2002 | Brysch et al. ..................... 435/6 |
| 6,410,715 B1 | 6/2002 | Sonenberge et al. |
| 6,582,908 B2 | 6/2003 | Fodor et al. |
| 6,656,730 B1 | 12/2003 | Manoharan |
| 6,887,906 B1 | 5/2005 | Teng et al. |
| 7,250,496 B2 * | 7/2007 | Bentwich .................. 536/23.1 |
| 7,399,852 B2 * | 7/2008 | Becker et al. .............. 536/24.3 |
| 7,468,431 B2 | 12/2008 | Bhanot et al. |
| 7,618,814 B2 * | 11/2009 | Bentwich ................ 435/320.1 |
| 2003/0027780 A1 | 2/2003 | Hardee et al. |
| 2003/0041341 A1 | 2/2003 | Sonenberg et al. |
| 2005/0196787 A1 | 9/2005 | Bhanot et al. |
| 2009/0203765 A1 | 8/2009 | Bhanot et al. |

FOREIGN PATENT DOCUMENTS

| WO | WO 9401550    | * | 1/1994 |
| WO | WO 98/39352   |   | 9/1998 |
| WO | WO 99/14226   |   | 3/1999 |
| WO | WO 2007/062380 |  | 5/2007 |

OTHER PUBLICATIONS

Elbashir et al., "Duplexes of 21-nucleotide RNAs mediate RNA interference in cultured mammalian cells" Nature (2001) 411:494-498.

Elbashir et al., "RNA interference is mediated by 21- and 22-nucleotide RNAs" Genes Dev. (2001) 15:188-200.

Ferguson et al., "Ser-64 and Ser-111 in PHAS-I are Dispensable for Insulin-stimulated Dissociation from eIF4E*" J. Biol. Chem. (2003) 278(48):47459-47465.

Final Rejection for U.S. Appl. No. 11/042,899 dated Jan. 24, 2008.

Fire et al., "Potent and specific genetic interference by double-stranded RNA in Caenorhabditis elegans" Nature (1998) 391:806-811.

Flynn & Proud, "Serine 209, Not Serine 53, Is the Major Site of Phosphorylation in Initiation Factor eIF-4E in Serum-treated Chinese Hamster Ovary Cells" J. Biol. Chem. (1995) 270:21684-21688.

Grolleau et al., "Differential Regulation of 4E-BP1 and 4E-BP2, Two Repressors of Translation Initiation, During Human Myeloid Cell Differentiation" J. Immunol. (1999) 162:3491-3497.

Hu et al., "Molecular cloning and tissue distribution of PHAS-I, an intracellular target for insulin and growth factors" PNAS (1994) 91:3730-3734.

International Search Report for PCT/US2006/061175 dated Aug. 2, 2007.

Lawrence & Abraham, "PHAS/4E-BPs as regulators of mRNA translation and cell proliferation" Trends Biochem. Sci. (1997) 22:345-349.

Lin et al., "Control of the Translational Regulators PHAS-I and PHAS-II by Insulin and cAMP in 3T3-L1 Adipocytes" The Journal of Biological Chemistry (1996) 271(47):30199-30204.

Mader et al., "The Translation Initiation Factor eIF-4E Binds to a Common Motif Shared by the Translation Factor eIF-4y and the Translation Repressors 4E-Binding Proteins" Mol. Cell Biol. (1995) 15:4990-4997.

Martin et al., "Ein neuer Zugang zu 2'-O-Alkylribonucleosiden und Eigenschaften deren Oligonucleotide" Helv. Chim. Acta (1995) 78:486-504.

Montgomery et al., "RNA as a target of double-stranded RNA-mediated genetic interference in Caenorhabditis elegans" PNAS (1998) 95:15502-15507.

New England Biolabs, 1998/1999 Catalog, pp. 121 and 284.

Nielsen et al., "Sequence-Selective Recognition of DNA by Strand Displacement with a Thymine-Substituted Polyamide" Science (1991) 254:1497-1500.

Office Action for U.S. Appl. No. 11/042,899 dated Jul. 3, 2007.

Pause et al., "Insulin-dependent stimulation of protein synthesis by phosphorylation of a regulator of 5'-cap function" Nature (1994) 371:762-767.

Ptushkina et al., "Repressor binding to a dorsal regulatory site traps human eIF4E in a high cap-affinity state" EMBO J. (1999) 18:4068-4075.

Reynolds et al., "Rational siRNA design for RNA interference" Nature Biotechnology (2004) 22(3):326-330.

Rosenwald et al., "Upregulation of protein synthesis initiation factor eIF-4E is an early event during colon carcinogenesis" Oncogene (1999) 18:2507-2517.

Rousseau et al., "The eIF4E-binding proteins 1 and 2 are negative regulators of cell growth" Oncogene (1996) 13:2415-2420.

Scott, "Diagnosis, Prevention, and Intervention for the Metabolic Syndrome" Am. J. Cardiol. (2003) 92(1A):35i-42i.

Smith & Waterman, "Comparison of Biosequences" Adv. Appl. Math (1981) 2:482-489.

Sreekumar et al., "Sodium aresnite-induced inhibition of eukaryotic translation initiation factore 4E (eIF4E) results in cytotoxicity and cell death" Molecular and Cellular Biochemistry (2005) 279:123-131.

Strudwick & Borden, "The emerging roles of translation factor eIF4E in the nucleus" Differentiation (2002) 70:10-22.

Tabara et al., "RNAi in C. elegans: Soaking in the Genome Sequence" Science (1998) 282:430-431.

Tijsterman et al., "RNA Helicase MUT-14-Dependent Gene Silencing Triggered in C. elegans by Short Antisense RNAs" Science (2002) 295:694-697.

Timmons & Fire, "Specific interference by ingesting dsRNA" Nature (1998) 395:854.

Timmons et al., "Ingestion of bacterially expressed dsRNAs can produce specific potent genetic interference in Caenorhabditis elegans" Gene (2001) 263:103-112.

Tsukiyama-Kohara et al., "Tissue Distribution, Genomic Structure, and Chromosome Mapping of Mouse and Human Eukaryotic Initiation Factor 4E-Binding Proteins 1 and 2" Genomics (1996) 38:353-363.

Tuschl et al., "Targeted mRNA degradation by double-stranded RNA in vitro" Genes Dev. (1999) 13:3191-3197.

Wang et al., "The Phosphorylation of Eukaryotic Initiation Factor eIF4E in Response to Phorbol Esters, Cell Stresses, and Cytokineses is Mediated by Distinct MAP Kinase Pathways" J. Biol. Chem. (1998) 273:9373-9377.

Waskiewicz et al., "Mitogen-activated protein kinases activate the serine/threonine kinases Mnk1 and Mnk2" Embo J. (1997) 16:1909-1920.

Waskiewicz et al., "Phosphorylation of the Cap-Binding Protein Eukaryotic Translation Initiation Factor 4E by Protein Kinase Mnk1 In Vivo" Mol. Cell Biol. (1999) 19:1871-1880.

Whalen et al., "Phosphorylation of eIF-4E on Serine 209 by Protein Kinase C is Inhibited by the Translational Repressors, 4E-binding Proteins" J. Biol. Chem. (1996) 271:11831-11837.

* cited by examiner

SEQUENCE LISTING

<160> NUMBER OF SEQ ID NOS: 263

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
tccgtcatcg ctcctcaggg                                              20

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
gtgcgcgcga gcccgaaatc                                              20

<210> SEQ ID NO 3
<211> LENGTH: 20
<212> TYPE: DNA

<213> ORGANISM: Artificial Sequence
<220> FEATURE:
<223> OTHER INFORMATION: Antisense Oligonucleotide

<400> SEQUENCE: 3
atgcattctg cccccaagga                                              20

<210> SEQ ID NO 4
<211> LENGTH: 2782
<212> TYPE: DNA
<213> ORGANISM: H. sapiens
<220> FEATURE:
<221> NAME/KEY: CDS
<222> LOCATION: (237)...(599)

<400> SEQUENCE: 4

```
cgctgctgcc gctgctgttg ctcctgaggc tgctggctga ggccggagga tcgagcggcg      60
gcggcggcgg cggctgagag ggcggcggcg ggagcggagc gggacgaggg aacgggagga     120
agcgagcgag gagcgcgcag agcgcgcttt tccgtccgcc tgaggagccg aagcagcccc     180
ggccccgccg ccgccgcctg cccgccggac aaagccgaga gcccgcgccc acagcc atg    239
                                                                 Met
                                                                   1 tcc tcg tca gcc ggc agc ggc cac cag ccc agc cag agc cgc gcc atc      287
Ser Ser Ser Ala Gly Ser Gly His Gln Pro Ser Gln Ser Arg Ala Ile
          5                  10                  15 ccc acc cgc acc gtg gcc atc agc gac gcc gcg cag cta cct cat gac      335
Pro Thr Arg Thr Val Ala Ile Ser Asp Ala Ala Gln Leu Pro His Asp
         20                  25                  30 tat tgc acc acg ccc ggg ggg acg ctc ttc tcc acc aca ccg gga gga      383
Tyr Cys Thr Thr Pro Gly Gly Thr Leu Phe Ser Thr Thr Pro Gly Gly
     35                  40                  45 act cga atc att tat gac aga aag ttt ctg ttg gat cgt cgc aat tct      431
Thr Arg Ile Ile Tyr Asp Arg Lys Phe Leu Leu Asp Arg Arg Asn Ser
 50                  55                  60                  65 ccc atg gct cag acc cca ccc tgc cac ctg ccc aat atc cca gga gtc      479
Pro Met Ala Gln Thr Pro Pro Cys His Leu Pro Asn Ile Pro Gly Val
                 70                  75                  80 act agc cct ggc acc tta att gaa gac tcc aaa gta gaa gta aac aat      527
Thr Ser Pro Gly Thr Leu Ile Glu Asp Ser Lys Val Glu Val Asn Asn
             85                  90                  95 ttg aac aac ttg aac aat cac gac agg aaa cat gca gtt ggg gat gat      575
Leu Asn Asn Leu Asn Asn His Asp Arg Lys His Ala Val Gly Asp Asp
            100                 105                 110 gct cag ttc gag atg gac atc tga ctctcctgca aggattagaa gaaaagcagc     629
Ala Gln Phe Glu Met Asp Ile
            115                 120 aacactgata cttgtgtgca cctgatttgg ccaataggat caacagtgaa aagacagaag     689
aggcaatacc agcagtcccc attacagtct ccacctcccc gtcttcctct gggtgccaaa     749
tgatgggaag atgagcttca tctgaccatt tcttctccct gtctcctgtt ccccttccca     809
gttaaacagg ttagattgaa ggcccttgct gtatttctgt agagctaagc agcccttaga     869
ggaaaacagt tcaactctga cttttcctagt tgtttttta ttgagagcca ccctcatacc     929
ctgtaatttt gtcccaaatc aaatatcaac ctaccaacaa ctgcctggct gggaagtctg     989
gggaagggat acagagcttg gtgggcctaa caccattcat attccttacc ctctgtctct    1049
cctccctgta tcccacctat ggttcagtgt tgcaagagtc tgggcttggg gtctttaaaa    1109
ccagcagggg gaaatgataa aaagagagct gctttccctt ttaccttgag gtattcgtcc    1169
ctcgggacag agcacagctt gtgcaactct ggtagcgtta ccctgtgaca ctgttttgag    1229
```

```
gtccacttcc tttctttcct ctgggaggaa tgtcttctgt ctttggtatt atagttcatc    1289
ttcccattct tttacttagt gcatttgtgc agatatttt aactctgtac atcagaagag     1349
agcccttggt aaccagtttt gctcttcttc tgccactcct ccctgcttgc atctcgttgc    1409
tggcagagtc ctcttgtact tcaagaaagc aaagtgattt tgtctgctcc tagagcaggt    1469
ccataccaag taatagaggc actttagctt ccacttggtg ggtaaggcct gatcatagta    1529
ttctgtcaga taatgcctaa gaatgaccgc tgaagaacgt tgacccattt gagtacccgg    1589
tctcagtcgt cattttaag tccagtgagc attgtggtag ttgttcttag attgcagttt     1649
cttatgtttt gagtttgaag ttgattttca gaatgttctt agaaagaac tgcattttt      1709 tcctttgtgg atctgctttg tttggctgct gggatagata agcatgggct taaaaaatgt    1769
gttcctccca gttttcttgc ctttcctgtt gtactctgaa tttctctccc tacctccctc    1829
actttcttcc tctctccttc ctttccttcc tttttctcta ccaggccatt tttcaaattt    1889
acatcaaaga tacctgaagt gttggtatct gagaatatct gtcactcctc ttatctgaga    1949
agtgaccttt tatttttaag atgactacag acctatttt agatatgttt tcagtacaat     2009
tttgaacagc aactttttaa ttaaacatct tccagtgtta ggaagttgag aaacgttcat    2069
aggcaagtct gctgttctat gtcaccatct tttgtctccc ctagtccccc aggagctctt    2129
tcctttcccc tctagttttg ggtgtgcatg tttggagttt gtagtgggtg gtttgtaaaa    2189
ctggaccatt ctgccttgct atgggttgtt caagaaagcc tcattctttt ctgtgaccct    2249
ttcgcttttg cattcaccct ccttcccacc tacctgtcct ggggctgttg agcagcataa    2309
taatcccggg agaatgattc ccctcataga aagacaaaag catccatccc ctcatagtta    2369
agtagccact ggtgtcctgg gaatttctgg ttggatttgg tgccctgaac ttttttatta    2429
agaaatcaga tcccagggtg agagtaacag gccatttggc caagaaagaa acctgtttgt    2489
ttttcttttg aactatgaaa agaccctgtt tgtgaatata ttttagaaag agaggaagga    2549
tgtctgcaga actttgttct gttttctgcc acaaaaatgt gaatagttca gagtgaaaac    2609
cttttgtgat ggttgatgtc tcaggaataa gctggatctc caatgttttg gggatgcttt    2669
gagtctcaaa aaaattgat aatcagaaaa gtaattttg tttgtttgtt taatgtatcc      2729
ctgttctgtt tttaattaaa ctccaagtct cattttaaaa aaaaaaaaa aaa            2782
```

<210> SEQ ID NO 5
<211> LENGTH: 23
<212> TYPE: DNA
<213> ORGANISM: Artificial Sequence
<220> FEATURE:
<223> OTHER INFORMATION: PCR Primer

<400> SEQUENCE: 5
cctctagttt tgggtgtgca tgt                                            23

<210> SEQ ID NO 6
<211> LENGTH: 20
<212> TYPE: DNA
<213> ORGANISM: Artificial Sequence
<220> FEATURE:
<223> OTHER INFORMATION: PCR Primer

<400> SEQUENCE: 6
cccatagcaa ggcagaatgg                                                20

<210> SEQ ID NO 7
<211> LENGTH: 32

-continued

```
<212> TYPE: DNA
<213> ORGANISM: Artificial Sequence
<220> FEATURE:
<223> OTHER INFORMATION: PCR Probe

<400> SEQUENCE: 7
tggagtttgt agtgggtggt ttgtaaaact gg                                    32

<210> SEQ ID NO 8
<211> LENGTH: 19
<212> TYPE: DNA
<213> ORGANISM: Artificial Sequence
<220> FEATURE:
<223> OTHER INFORMATION: PCR Primer

<400> SEQUENCE: 8
gaaggtgaag gtcggagtc                                                   19

<210> SEQ ID NO 9
<211> LENGTH: 20
<212> TYPE: DNA
<213> ORGANISM: Artificial Sequence
<220> FEATURE:
<223> OTHER INFORMATION: PCR Primer

<400> SEQUENCE: 9
gaagatggtg atgggatttc                                                  20

<210> SEQ ID NO 10
<211> LENGTH: 20
<212> TYPE: DNA
<213> ORGANISM: Artificial Sequence
<220> FEATURE:
<223> OTHER INFORMATION: PCR Probe

<400> SEQUENCE: 10
caagcttccc gttctcagcc                                                  20

<210> SEQ ID NO 11
<211> LENGTH: 1781
<212> TYPE: DNA
<213> ORGANISM: M. musculus
<220> FEATURE:
<221> NAME/KEY: CDS
<222> LOCATION: (121)...(483)

<400> SEQUENCE: 11
cgaccgggcg agagcaggcg agttgagagc cgagcgtgag gagccagagc cgccggccc       60 cgccgccgcc gccgccgccg ccgccgctgc tgcacaaagc ctcgagcccg cgtcggagcc     120 atg tcc gcg tcg gcc ggt ggt agc cac cag ccc agc cag agc cgc gcc       168
Met Ser Ala Ser Ala Gly Gly Ser His Gln Pro Ser Gln Ser Arg Ala
 1               5                  10                  15 atc ccc acg cgc acc gtg gct atc agc gac gcc gcg cag cta cct cag       216
Ile Pro Thr Arg Thr Val Ala Ile Ser Asp Ala Ala Gln Leu Pro Gln
             20                  25                  30 gac tac tgc acc acg ccc ggg ggg acg ctg ttc tcc aca acg ccg gga       264
Asp Tyr Cys Thr Thr Pro Gly Gly Thr Leu Phe Ser Thr Thr Pro Gly
         35                  40                  45 gga aca cga atc att tat gac cga aag ttt ctg ttg gac cgt cgc aat       312
Gly Thr Arg Ile Ile Tyr Asp Arg Lys Phe Leu Leu Asp Arg Arg Asn
     50                  55                  60 tct ccc atg gcg cag acc cca cct tgc cat ctg ccc aat atc cct gga       360
Ser Pro Met Ala Gln Thr Pro Pro Cys His Leu Pro Asn Ile Pro Gly
 65                  70                  75                  80
```

| | | |
|---|---|---|
| gtc acc agt cct ggc gcc tta att gaa gac tcc aaa gta gaa gtg aac<br>Val Thr Ser Pro Gly Ala Leu Ile Glu Asp Ser Lys Val Glu Val Asn<br>85 90 95 | | 408 |
| aac tta aac aac ctg aac aat cat gac agg aag cat gca gtt ggg gat<br>Asn Leu Asn Asn Leu Asn Asn His Asp Arg Lys His Ala Val Gly Asp<br>100 105 110 | | 456 |
| gag gct cag ttt gag atg gac atc tga ctactgccat gtggaaggag<br>Glu Ala Gln Phe Glu Met Asp Ile<br>115 120 | | 503 |
| gcctcgtgga gcagcctgtg tgcacctgac tggcccagta ggaacacagt gtacagagaa | | 563 |
| gctcctgtcc ccctgtcccc tctgggtgcc aaataatggg agatgtgcac tgtctgatca | | 623 |
| catcttcccg tctcctgccc tctgcccagt taaggttagg ttgatgaata agcccttgga | | 683 |
| ttattctgtg gagctgacag tccacagaag aaagcagtcc ctgtagcttc cctggtcatt | | 743 |
| tcccaagaat cttcctgccc tgttgagact tgccccaagt ctagggcagt ctccaagcag | | 803 |
| cacctctgct tgtaggggtt gggggtgaag gaggtttagt gcccattgtg ttcctgggct | | 863 |
| ctccctgtcc ttccctacag accactactg gtggagcgct ggatgtgggg gacatttgtc | | 923 |
| ctcagctctg gagcacagtc ctgtacctcc tgcacctctg ctgcattcct gggacatgtg | | 983 |
| acagcagcct ccccttttctc tgggaggaag gcttctgtct tgtcttgggt gtgatagctc | | 1043 |
| atcatccccc cccccccatt cctttaccca tttcattggc acgggtattt tttaagccct | | 1103 |
| cctgaaggga cccccttggtg accagctggt ctttgcctgt ctgacattct ttctacctgc | | 1163 |
| atcccgtagg cagagtctgc cctggcacac ccgtggctct gtctgctttt agagcagaag | | 1223 |
| tgccaacacc ttggcctgca cctggtgagt ccagcctgct ctcagcggtc tgcctgagaa | | 1283 |
| tacatcaggg gcctctgaag aggactgagc cgccgtgcag ccagcctcgg gggtcatggt | | 1343 |
| tttaaaacca ggtgtacctt acgttgggtg tcctgcaggt tactatacct tgagtttaaa | | 1403 |
| gtcgacttcc tcttacattt ctcccctgct ttggatctgc tttgtgcttg gctgctgaga | | 1463 |
| gagcagcaca ggctaagaca gtgtattcct cccaggtctc tcgcccttct catcgtccgt | | 1523 |
| ctgtccgtca gtccgtccgt ccttccctcc ctctcccctt aaattctttc cttctggttc | | 1583 |
| ttccaccggg ccatттттcca catctgcatc agaagagatg cctcccatgt tagtatctga | | 1643 |
| taatatcagt ctctccttat cagaggagag accttttatt tttaagatga ctacagacct | | 1703 |
| atttttagat aagttttcag tacaattttg aactacaact ттттттaacaa aacatcttcc | | 1763 |
| agtattggga aggttatt | | 1781 |

<210> SEQ ID NO 12
<211> LENGTH: 23
<212> TYPE: DNA
<213> ORGANISM: Artificial Sequence
<220> FEATURE:
<223> OTHER INFORMATION: PCR Primer

<400> SEQUENCE: 12
agagcagcac aggctaagac agt     23

<210> SEQ ID NO 13
<211> LENGTH: 19
<212> TYPE: DNA
<213> ORGANISM: Artificial Sequence
<220> FEATURE:
<223> OTHER INFORMATION: PCR Primer

<400> SEQUENCE: 13
cggacagacg gacgatgag     19

```
<210> SEQ ID NO 14
<211> LENGTH: 20
<212> TYPE: DNA
<213> ORGANISM: Artificial Sequence
<220> FEATURE:
<223> OTHER INFORMATION: PCR Probe

<400> SEQUENCE: 14
cctcccaggt ctctcgccct                                              20

<210> SEQ ID NO 15
<211> LENGTH: 20
<212> TYPE: DNA
<213> ORGANISM: Artificial Sequence
<220> FEATURE:
<223> OTHER INFORMATION: PCR Primer

<400> SEQUENCE: 15
ggcaaattca acggcacagt                                              20

<210> SEQ ID NO 16
<211> LENGTH: 20
<212> TYPE: DNA
<213> ORGANISM: Artificial Sequence
<220> FEATURE:
<223> OTHER INFORMATION: PCR Primer

<400> SEQUENCE: 16
gggtctcgct cctggaagat                                              20

<210> SEQ ID NO 17
<211> LENGTH: 27
<212> TYPE: DNA
<213> ORGANISM: Artificial Sequence
<220> FEATURE:
<223> OTHER INFORMATION: PCR Probe

<400> SEQUENCE: 17
aaggccgaga atgggaagct tgtcatc                                      27

<210> SEQ ID NO 18
<211> LENGTH: 497
<212> TYPE: DNA
<213> ORGANISM: R. norvegicus
<220> FEATURE:
<221> NAME/KEY: CDS
<222> LOCATION: (39)...(401)

<400> SEQUENCE: 18
gccgccgctg cacaaagcca cgagcccgcc ccggagcc atg tcc gcg tcg gcc ggt      56
                                         Met Ser Ala Ser Ala Gly
                                           1               5 ggt gga cac cag ccc agc cag agc cgc gcc att ccg aca cgc acc gtg      104
Gly Gly His Gln Pro Ser Gln Ser Arg Ala Ile Pro Thr Arg Thr Val
         10                  15                  20 gct att agc gac gca gcg cag cta cct cag gac tac tgc acc acg ccc      152
Ala Ile Ser Asp Ala Ala Gln Leu Pro Gln Asp Tyr Cys Thr Thr Pro
     25                  30                  35 ggg ggg acg ctg ttc tcc aca aca ccg gga gga aca cga atc att tat      200
Gly Gly Thr Leu Phe Ser Thr Thr Pro Gly Gly Thr Arg Ile Ile Tyr
 40                  45                  50 gac cga aag ttt ctg ttg gac cgt cgc aat tct ccc atg gcg cag acc      248
Asp Arg Lys Phe Leu Leu Asp Arg Arg Asn Ser Pro Met Ala Gln Thr
55                  60                  65                  70 cca cct tgc cat ctg ccc aat atc cct gga gtc acc agt cct ggc gcc      296
```

```
             Pro Pro Cys His Leu Pro Asn Ile Pro Gly Val Thr Ser Pro Gly Ala
                         75                  80                  85 tta atg gaa gac tcc aaa gta gaa gtg aac aac ttg aac aac ctg aac       344
Leu Met Glu Asp Ser Lys Val Glu Val Asn Asn Leu Asn Asn Leu Asn
             90                  95                 100 aat cac gac agg aag cac gca gtt ggg gat gag gct cag ttt gag atg       392
Asn His Asp Arg Lys His Ala Val Gly Asp Glu Ala Gln Phe Glu Met
        105                 110                 115 gac atc tga ccctgctgca gtgtcgaagg cggcccctga cacggcccgt gtgcacctga    451
Asp Ile
    120 ctggaccagt aggaacaccg tgtacagaga agctccagtc cccctg                    497

<210> SEQ ID NO 19
<211> LENGTH: 26
<212> TYPE: DNA
<213> ORGANISM: Artificial Sequence
<220> FEATURE:
<223> OTHER INFORMATION: PCR Primer

<400> SEQUENCE: 19
agtgaacaac ttgaacaacc tgaaca                                          26

<210> SEQ ID NO 20
<211> LENGTH: 21
<212> TYPE: DNA
<213> ORGANISM: Artificial Sequence
<220> FEATURE:
<223> OTHER INFORMATION: PCR Primer

<400> SEQUENCE: 20
actgcagcag ggtcagatgt c                                               21

<210> SEQ ID NO 21
<211> LENGTH: 24
<212> TYPE: DNA
<213> ORGANISM: Artificial Sequence
<220> FEATURE:
<223> OTHER INFORMATION: PCR Probe

<400> SEQUENCE: 21
tcacgacagg aagcacgcag ttgg                                            24

<210> SEQ ID NO 22
<211> LENGTH: 23
<212> TYPE: DNA
<213> ORGANISM: Artificial Sequence
<220> FEATURE:
<223> OTHER INFORMATION: PCR Primer

<400> SEQUENCE: 22
tgttctagag acagccgcat ctt                                             23

<210> SEQ ID NO 23
<211> LENGTH: 21
<212> TYPE: DNA
<213> ORGANISM: Artificial Sequence
<220> FEATURE:
<223> OTHER INFORMATION: PCR Primer

<400> SEQUENCE: 23
caccgacctt caccatcttg t                                               21

<210> SEQ ID NO 24
<211> LENGTH: 24
```

```
<212> TYPE: DNA
<213> ORGANISM: Artificial Sequence
<220> FEATURE:
<223> OTHER INFORMATION: PCR Probe

<400> SEQUENCE: 24
ttgtgcagtg ccagcctcgt ctca                                          24

<210> SEQ ID NO 25
<211> LENGTH: 25324
<212> TYPE: DNA
<213> ORGANISM: H. sapiens
<220> FEATURE:

<400> SEQUENCE: 25
tttttaaaat acagtacatc gtgcatgtag tgcctgaatt aataatgaac aattaaaagt      60
aaaattacat ttttaatgca taggaatgca tgagaaactc aagtctgctc aagtaaagtg     120
gtgttaaccg acaatgacaa acaataagaa gaaagttttc cttgtccgcc ttcaccaggc     180
tcacaaacac ttagctcgcg ctccctctgg ctcttctccc gctcgctggg gttaagccac     240
tctcttcctc agccctgccc ctcgtccccg cccccttcaa caacttcagc cacgcccctc     300
actgcctcgc cccgccccgc ggcgacgtca cctccggccg accagcttcc ccaactccct     360
ctggctcccg ccttcgcccg cttccggtcg tcgtcgtcgc cgctgctgcc gctgctgttg     420
ctcctgaggc tgctggctga ggccggagga tcgagcggcg gcggcggcgg cggctgagag     480
ggcggcggcg ggagcggagc gggacgaggg aacgggagga agcgagcgag gagcgcgcag     540
agcgcgcttt tccgtccgcc tgaggagccg aagcagcccc ggccccgccg ccgccgcctg     600
cccgccggac aaagccgaga gcccgcgccc acagccatgt cctcgtcagc ggcagcggc      660 caccagccca gccagagccg cgccatcccc acccgcaccg tggccatcag cgacgccgcg     720
cagctacctc atgactattg caccacgccc gggggacgc tcttctccac cacaccggga      780
ggtgagcgcc ggccagccgt ccgccgcgcc cggtgtcccg ccgcggtcct ctaactcctc     840
ggcgcctcgg tgcccggccg cttcgccccc gccccagct ccaccgaagc cccggggacg     900
ctgcccttgg gcccgcccga gcgttcggga ccctttactt cgtgttcgct cttgcccgca     960
gctcgagtcg gcgcgcgccc cactcgggaa tgtggctgtc ctgtcgcgaa aaagagctct    1020
tgtttccgct tcgtggcagg cttacgcatt cgacccagtt ctctctctcc tctctgcctc    1080
cttcccgggc ggatttggct ccacttggcc ttgcattaca gtctgcattg cctgtcgtag    1140
attgtgcaaa ttaatgcttg attttggagc tggctccggg gcttttaaa aaagaacttt     1200 gggagaggaa ttcggccctg gcatcctgcg atggcttgtt tttgctgctt ttagaacacc    1260
gggaggaggc tggaatgcgg agtctggaag cctcgcccag cgttatcccg ctttgacagc    1320
attgtttact ttgctggacg aggccccacg ggtgagggga gtccccaggc cgggaggaga    1380
gcgtgataaa ataaagctca agtaatagcc aagggaaagt aggtggggt ggtagggtgc     1440 tgacagcctt aaggtagggt gtctttcggc agcgacgcct ttggaaatgg attgaaggac    1500
ctttgtcaag gacaccccag ttgggtgggg tggttgcttg atcctgtgga agggggctaga   1560 gagaggcaat ccagagagag ggtggttccc tggcattgct tttcaaagca tgaccaggaa    1620
ctgtttacaa ataagtaata ctggggtaga ggtgaagctt ggtcacggga agagagctca    1680
aaggttgtct gtgccctaac tgggctgtcc tccagaggga ggagcctgga aagcgatttt    1740
gaggagcctt attgaaggga acggggcctc cttttaact tcagaacttt gtcttctttt     1800
ggtgctgggg tggcctcttg ctagagggtg gggacttcgc agctcctgcg gtctagagga    1860
```

```
ttgctagcct tgttcctgtg ggcagggctc aggagctgta ctacaaccaa tccgatgcag    1920
ttaggcctgg accatcctta aatcagttgc acaatagcaa ggcctgtgga gtaaggagac    1980
cttcttgcca acaccaaggg ataaaatcta ggagggagct ttacagagaa attcagccag    2040
gccgctctgg gggctgggcg ggctgccttg aaaggctttt taaatgaccc aggcagaagt    2100
tcagtaatat atatggagag ctgggtttaa ggaaatgtta actttgcaga atagtggagt    2160
tcttaggtgg cttaactcat ggaagaaatc tcccccgat atgatcagtt caagaccaac      2220
tcgtgtttga gcatggtaca gggtctcact ctgtcgccca ggctggagta cagtggcacg    2280
acctcggctc actgcactct ctacttcctg ggctcaagcg atcctcccac ctcagcctcc    2340
tgagtagctg gaccacaggc acgtgccacc acgcctggct aattttttg tattttggta     2400 gagtctgggt ttctccatgt tgcccaggct cgtcctgggc tcaagttatt cgccccgtca    2460
gcctcccaaa gtgctgggat tacaggcgtg agccactgca cccggccaag atcttgcttt    2520
ttaatcctga aaaattttgg cagaccagaa tctgctccat ataagagttg tcttgaactt    2580
gaactgatag cttttaagaa atagatgctg ttttccgagg tgatggaaag ggatttataa    2640
cttcttccag aattctttgt ggtattgctc agtaaatgcc tgtgcttcca gaagttcaga    2700
acacgtcata gtgacaactg cactcagcta taatgtattt ggaaagggaa ctaaactttc    2760
agctatatat taatcccctg agggaagagc cacctagaca cgttttttggc ttatgtcaaa   2820 tagtcaagct accatacttt taaaaataag gcatagtct ttaagcgttg cttcaaagat     2880
agaagcctgt ctcatagcct ggattagttc ttaaagtgct tgcaaagagt ctgccagaaa    2940
tactaattca ttacccctcc tcctaacaac actcaatcac tgttttctca aatatcactt    3000
aacttccccc gacattgttt ctacacacag tttcttgttt tggatttaaa tacttgtgat    3060
cttggctctt ctttactgtt gagcttgtat ttattgggag agcccatcat aatctttgga    3120
tttatttgtt tatttattta ttttattttg gagacggagt ttcgctctgt agcctaggct    3180
ggagtgcagt ggcgcgatct cggctcactg caagctctgc ctcctgggtt cacgccattc    3240
tcctgcctca gcctcccgag tagctggggc tacaggcgtc caccaccacg cccagctaat    3300
tttttgtatt tttagtagag atagggtttc accatgttag ccaggatggt ctttttttt      3360 ttgttgttgt tgatcattct tgggtgtttc tcgcagaggg ggatttggca gggtcacagg    3420
acaatagtgg agggaaggtc agcagataaa caagtgaaca aaggtctctg gttttcctag   3480
gcagaggacc ctgtggcctt ccgcagtgtt tgtgtccatg ggtacttgag attagggagt    3540
ggtgatgact cttaacgagc acgctgcctt caagcatctg tttaacaaag cacatcttgc    3600 accacccta atccattcaa ccctgagtgg acacagcaca tgtttcagag agcacagggt     3660
tgggggtaag gtcacagatc aacaggatcc caaggcagaa gaattttct tagtacagaa     3720 caaaatgaaa agtctcccat gtccacctct ttctacacag acacggcaac catccgattt    3780
ctcaatcttt tccccacctt tcccccctt ctattccaca aaaccgccgt tgtcatcatg      3840
gcccgttctc aatgagctgt tgagtacacc tcccagatgg ggtggtggcc gggcagaggg    3900
gctcctcact tccagtagg agcggccggg cagaggcgcc gctcacctcc cgggcggggg     3960 gctgacccc cccccacctc cctcccagac ggggcggctg gccgggcaga ggggctcctc     4020
acttcccagt aggggcggcc gggcagaggc ccctcacc tcccagatggg gcggctggc      4080 cgggcggggg gctgaccccc cacctccctc ccggatgggg cggctggccg ggcagagggg    4140
ctcctcactt cccagtagga gcggccgggc agaggcgccc ctcacctcct ggacggggcg    4200
gctggccggg cggggggctg acccccccac ctccctcccg acggggcgg ctggccgggc     4260
```

```
gggggggctga cccccccacc tccttcctgg acggggcggc tggccgggca gagggctcct    4320
cacttcccag taggggcggc cgggcagagc gcccctcacc tcccgacggg ggcggctggc    4380
caggcggggg gctgaccccc cccacctccc tcccggacgg ggcggctggc cgggcggggg    4440
gctgaccccc ccacctcctt cctggacggg gcggctggcc gggcacaggg tctcctcact    4500
tcccagtagg ggcggccggg cagaggcgcc cctcacctcc cggacggggc ggcttagcca    4560
ggatggtctt aatcttctga cctcgtgatc tgcccgcctc ggcctcccaa agtgctggga    4620
gtacaggcgt cagccactgc gcctggctgt aatcagtgga ttttaacat gagggcttat     4680 ttaatatctt tataaggaca tggtgccgtt gcagttggat ttaatcacta ttacagcaat    4740
gaatactgtt taggtgttct ttacttactg atttaacttc cccctctgac ggtttgtgta    4800
tctctaatgc tacattcatc ttcctctcat catgtaattt tatttccctc aaccagggtg    4860
caatagtttg ttatctggcc acctccagac tcctggatta atatggttag gtatcgttag    4920
taaattttgt gtgcccaggg gagtggttcg cacaaaaggg gacaacagac aaaagtagga    4980
aatacagtcc ttggtctgaa caggtttaaa ttcttgattt gggggtaggg gcagacagat    5040
aagattttta gttctgaaag agtagagtca agtgctaaca tatatttcag acttgaaaac    5100
atttagaaaa atgagtgata ggcttgtatt ggaaatctct atttagtggt aagggagggg    5160
attaacattt cctgcctcaa acttctagaa atcttctgga gggtcacata catgtcagag    5220
cattccagca taacaacagt tgatggaccg aatgccctaa atgatcagac tgagcaggga    5280
cattcacagc atagcaaact tagagtttct cccccttgaa gagttcttta ttcattgggg    5340
atcacaggag atacagctta cccttgagct ttctcaaaat tgtctttctg tggtttggga    5400
agtgagaagt gggtgaaaac acacttgctg taacctcttg gatttctcat attgctggaa    5460
gagtacccct tctccttatg aaggaagagg aaacttttg ttgggcaaat tccaggccaa    5520 aaaaaagct cttggatttt atttttttt ctatctgcct gtggaggagt ggggatgata    5580
tttggttctt ccattgagaa gctacctctg ccctcaaagg aagtaaagt tactatagtt    5640 ggctccactt ttaataacac tagtgaccta gaagaaacct aatgctttca ttttattatt    5700
gagagaaatt gggacccaga gaagttaagt aacttgttag tattaaacag ctaattattg    5760
tccgtgagtc cctcaaattt agtatcctga tcactattcc agttttttcc tctactgttt    5820
tgagatgctt atcttactag gaaaggaagt ttgcaaacat ttaaagagac ttttctacct    5880
ctggaatgct agctaatatg attctttccg ctaccttatt tcctttctag gtgctgaact    5940
gccccctttt agaagagttg ttttgctctg cggaatgagc agaaacagag cacctctttt    6000
taccctttct ctttgccttt cttttccttc acagagttct catcagccat ggaaaagtat    6060
gctgttacca taacaagggc agcagagggg aactaactgt gatggtctga aattttgtct    6120
gggttgtagc tcttctgcct cttggatagt tgatatgatt ggttcattgg gacagaattt    6180
cataaaggtc attggatggg tttggaaaaa aggagaaagc aggaagaagg gaaaataatc    6240
cactgggagt gaaagtgaac tataccaaaa taaagagtat tgggggtgaa gggagctgct    6300 ttttttttc tttctttctt tgagacagag tttcactctt gttgcccagg ctggagtgca    6360
atggcgccat cttggctcac cgcaacctcc gcctcctggg ttcaagtgat tctcctgcct    6420
cagcctcctg agtagctggg attacgggcg cccaccacca cgcgtggctg attttttgtat   6480 tttagtaga gatggggttt taccatgttg gccaggctgg tctcgaactc ctgacctcaa    6540
gtgatccgcc cacctcggcc tcccagagtg ctgggattga accaccatgc ccagccctgt    6600
ttcttttgtt aagataaaaa ttgtctttgt tggtttatta gcacttcaga gatttgatgg    6660
```

```
ttgtgcacag tgaatgtggt ttggccacca cctgtctccc tgaagaatac agagttaggc    6720
agcttttagt ttcctctggg ttatttgcca tagagctttt caggagtctg tctcttcatc    6780
cagagtctcc atgaagaaca gatgtttaaa actgaagttc attcatgaat gttctataac    6840
tcagtcaata aaacatagac cttgttctac cttcctaagt tgaaagaata aaaagcagag    6900
aaaacacttt ctttgttaag tcctttctgt ttttccttt cttattttcc cttatggggg    6960
tgggagagag aaagacaggc ttagacttct tttctgagtg cattagaagc acttgctgct    7020
tgttcatctt gtatctgttt ctcatctttt ggtgggccct tatgtgagac atagctggag    7080
aattgtcaag aattcctagt agaaattgaa gttacatgcc aaatgctttg tttctttttt    7140
taattcaatg tctaggcttg aaggatacct tcctcctcgt ggtccctgct gccctagcag    7200
tgttggtttg tatgtatgta tttataagat attttgtaag catctttttt cttagttcct    7260
tataatggtt ttttaataca ctatctcttg atgttttaaa catacataac aaaaatttcc    7320
attttagtca tttttaattg tacagctcag tgggattaaa tatattcacc ttgttttgca    7380
accatcacca ccatccatct tcagaacgtt tttcatcttc ctaaactgaa acctcatacc    7440
aattaaacaa taacttccca ttaagcagta ccaccgcagc ctccggcagc taatcatcct    7500
actttgtgtc ttcatgaatt tgactactct aggaatctca gttaaatgga accacgtagt    7560
aattgtccct tcgtaaatga acattcatca gtgttcatgc ttttttttctt gccattttgc    7620 tttttttttt tattattatt acattttttt aatacctatg aaagcaacaa agttgtaaaa    7680
gtcatatagt cttactggcc acacaacaaa aagcaacatt ccgatgcccc gttccttcat    7740
ctccatttcc actctcagag aaaccatttt aaactcattt agctaatgtg cactgcagcc    7800
ttgacctcct gggctcagcc tcctgggatc ataggagtgc caccaagcac ggctaatttt    7860 taaaatttt gtaaagatga tttctcacca tgtttcccaa gctggtctta aactcctggg    7920
ctcagatgac cctcttgcct cagcctccca aagtgctgtg attataggtg tgagcccta    7980 tgcccagcct atttcttagt ttgggatatt aattcatttt ctgctatgga agatgaggat    8040
ttagttgtta tatacaccct tctcccaatg tatatacttc tgtctcctat cctcttaatt    8100
taactttttt ttacccttt tggtcaaact aatatgtatg taatctttac taaattttgg    8160
taaatattga atgcagatgt ggctgacatt gttggtttcc tgctcaatag ctattccctc    8220
ttcttgcttg ctgccagatt ccctcatttt ttaaatggca aggtgctaaa ccccaggata    8280
tagactgtga cagctcttaa gtcagtcata gtttccccag tgtttggtct ggtgggcatc    8340
tgaaccagtt ctggacaaat gagatgtaaa ggaagtctgc tgatggcttc tgagattttc    8400
ccctccaacg gagaaagtcc caggaggaaa gccctgtttg acttcatgtt ctcctttcct    8460
gcttggaact ctattttatg agggtgtggg tccatctcag cctttttgga gggcttgtgg    8520
gcaagttact taatgtttcg ttctccaggc tgtctatttg cgtgagtaaa tggttaattc    8580
taattctgga agcagactta gttaaacaga atttttatgat ggcggccggg gggtgggggt    8640
gggggctccc tgtaaaaata tagttaacaa ctaccctgta agttaaccat gttatagtgg    8700
actttctctg tgtggtttaa tttcagctta cataatttct taactatata gcttaatgca    8760
tggattattt atcatttaaa ctaaggtact tggtattgaa agaggccgtt acgcttgaat    8820
gaccttgttt ctatactagc catcttggca agcataactt tgggctttat tcattgacct    8880
tcttgttgtt ttctgcagtt tgagaatcac tggtttttag attcaaaggt agatagggtt    8940 tttccccct ctctgtcaaa gggactcagt tttactctca tatttcccta gtaatgttaa    9000
atctagaaag tcctggatga aagtattaga tttatcctaa tatctggtca ctaagggatg    9060
```

```
aaaaatttat aaatagctaa tgttaaccta gatctaaagc ttcctattct gaaatccaaa    9120
catgaagact aagaaaaata tgtacatttt gaaacaaagc agaaaaatga aacttcaaca    9180
atgtaaaaga gggtaaaatg ccagtagaca gccactttca gcagtttctg tttacagtgc    9240
ttttgctggc taccattgtt gctgtaaata atatatgtat actgtgattt ctttaacatt    9300
agacaatact gttaactccc cattatgaaa gatgaggaat ctaagatact tttattactt    9360
tctgtctctt gtttctcatc ctctctccat ttactaattt ctgtaaattg tattatcatt    9420
tttggctcct ctagtagtta tctttaaagc tctaaataat atgtgtctca acctgtcaac    9480
tttagctctc cactgtataa aagtacacca ttcacctgtc ctcctgcctt tactttgctg    9540
gtatgtaacc tcattatgtt tataatatca gggtttgtgg gcaggcttgg tggcgtacac    9600
ctataatccc aacactttgt gaggccaagg caggagaatc gcttgagccc aggagtttga    9660
gaccagtcag ggcaacgtaa tgagacccca tctctacaaa atataaaatt agttggactg    9720
tagtcccagc tacttgggag gctaaggtgg gaggatcacc tgagcccagg aggtcaaggt    9780
tgcagtaagc cgtgatcatg ccactgcact caagcctggg tgatagagca agaccctgac    9840
tctcaaaaaa aaaaaaaaaa aaaaagaaa tcagagtttg taacatttac gtactgttcc    9900
ttaactgtta attcttctat gcttttacta tagtttgatt ataaacgttg aaaatcaaac    9960
agcatataca atattgtgat tttttttcat aactttccaa tataagacta aggagcatga   10020
ttattttcat agagaaggaa tggaaaattg tttttttaatt tttgtaacac tccatcaatt   10080
gatcacaatc atgccccatt ttaatactgt gttatatgag ctatggattt cttgtgtagt   10140
ctgttttcct tcttcagtag cttaaggtta acttgtttct agttacttat ggctgcattg   10200
gttgacatta aattgagctg acatagcgtt ggagggagtc tgggtgaaat gtgaattgct   10260
aggaagtcct tgcttcagaa aatgtacatc tgtgcatgca tatgtataag aaaccttaaa   10320
tattttagat ttttttaatag attgtcttgg aattgatgta agtttatagt aaacataata   10380
ttcaataaag gaaataaagg gttttttcct gccattttat ccatggttga atcttaattt   10440 ttttctttg aataattttg gttttttaaa aggtcagttt cttttgaatt acaccctaaa   10500
atcattagtg attaacaagc tgattctgta tttttgcttt atcccacta caattaaatt   10560 tttttagct tgcagagatt actaaaattc aaaaacttat aaatactata ctttcatagt   10620 catattttc ctggctatat ttgagaacat tacagcatta agacgctagt tcttcagtgt   10680
gtcttgttgt ctgaattatt tactgtgttg gcattcaaaa tcaaacatat cttaggaatg   10740
cattaaaaaa actattagaa ataataggtg agtttgccaa ggttgcaaga taaaagagcc   10800
atatagaaaa acctgttttt ggcccagcac agtggctcat gcctgtaatc ctagcacttt   10860
gggaggccaa ggcttgcaga tcacttgagg tcaggagttc gagaccagcc tggccaacat   10920
ggtgaaaccc catctctact aaaaatacaa aaattagctg gcatggtag cgcatacctg   10980 taatcccagc tatttgggag gctgaggcag aagaatcact tgaacccaga gggtggaggt   11040
tgcagtgagc tgagatcaca ccctgcactc cgcctgggc agcagaggga aaatccatct   11100
caaaagcaaa aacaaagaaa actggtcacg cttgttatcc catcattttg gaaggctgag   11160
gtgggcagat ggcttgagcc caggagttca agaccagcct gggcaacatg gtgaaacccc   11220
gtctctacaa aaaatacaaa aattatttttt ttctgggtga catgtgcctg tagtcccaac   11280
tgctagggag gctgaggcag gaggaccgct tgagcccagg aggtgtaggt tgcagtgagc   11340
caagattgca cttctgccct ctagcttgga cgacagagca agaccctctc tcgaaaaaaa   11400 aaaaaagaa aagaaaaaga aagcaatccc atttacaata gcatgaaaac aatttgatag   11460
```

```
gaataacttt agtcacaaag cataaaactt ttactctgga aactacaaaa cattgttgaa   11520
agaaattaaa gaagacccaa ataagtggaa agacatttgg tggccatgga tcagaagact   11580
taatattgtt aagatggtag tactccacaa attgaccttc acattcagca cagtccctat   11640
cataatctca gctggcttct ttgacaagct gacaaaattc atatggaact ttaagggacc   11700
taaaatatcc agaacaatct tgaaaagaa aaactaagtt ggaggactta cactttgtgg    11760
tttcaaaact tattacaagt caagacagtg gggtactagc atatggatat acatatagat   11820
caatggaata aaattgagag tccagaaata aacccagcaa taatggccca ttgatcttca   11880
acaagggtgc caagacaatt ctgtggaaaa agaacagttt tcaacagata gtgctgatac   11940
aactggatat gcacacagaa aaactgaagg tggaccagat ggctcaaaga cctaaatgtc   12000
agagcaaaag ctattaatgt acaaccttta gaagaagaca gaggcaaatc tttatgacct   12060
tggattaggc agtggcctga gatatgactc caaaagcaca aacaaagaa  aaaaaaaaa    12120 acatacattg gacatcatga aaattaagaa cttttgtgct tcgaagatca tgaagaaaat   12180
gaaaagataa cccacagaat aggagactat atttgcagtc acataagaga tttatatcca   12240
gaataaagaa ctatcataat ttagtaataa agacaaatca ttgaaaaatg ggtaaaggtt   12300
ctgaatagac agtttcttca aaagaagata tgtggtggaa tggcctgtta agtacatgaa   12360
aacagcatgt tcaacataat tagccatcag ggaaatgcaa attaagatca aaccacagtg   12420
agaaaccact tcatatctgc taatgttggc tacaatatat aaaaattaga actcttacac   12480
actgctgatg ggaatgtaaa atagtacaac cactttgaaa aacaggcagt tctggccggg   12540
cgcggtggct cacgcctgta atcctaacac tttgggaggc cgagctgggc agatcacgag   12600
gtcaagagat cgagaccatc ctagccgaca tggtgaaacc ctgtctctac tagaaataca   12660
aaaattagcc gggcatggta gcatgcacct gtagtcccag gtacttggga ggctgaggca   12720
ggagaatcgc ttgaacccag gaggcggagg ttgcagtgag ccaagatcat gcagctgtac   12780
tccagcctgg tgacatagcg agactctgtc tcaaaaaaaa aaaaaaaaaa ccaggcaatt   12840
tttcaagggg ttaaaggtag agttaccata tgacccagta gttctacctt aattttttaa   12900
tttttttttt ttttttttga dacagggtct cactctgtca tctaagctga gtgcagtggt   12960
gcaatcatgg ctcactgtaa cctccatctc ctgggcttaa gtgatcctcc cacctcagcc   13020
tccccagcag ctgggactat aggcatgcaa caccacgcct ggctaatttt tgtatttttt   13080
tttaagagac gggattttgc catgttgccc aggctggtct tgaacttgtg aggtcaagta   13140
atacacgttg gcctcccaaa gtgctgggat tacaggtgtg agccatgcct ggctaattcc   13200 actttttag tttggtatat acccaagaga atggaaatgt gttcacatga aaacttgtac    13260
gtgaatgtta ttcataatag acaaaaagtg gaaacaaccc atttatcagt tgatggactt   13320 gttttatcg  acttaccagt ccatcaactg ataaattgat aaggtgcgat atatacatac   13380
aatgaaatat ttggtaatga aaagaaatg aggtactgat aaatgctaca acataaatga    13440
actttgaaga cattatgaaa gtgaaagaag cagtcacaaa agactgtatt gtatgattcc   13500
atttatatga aatggccaga gtaggtaaaa ctatatagag acagaaagta gattagtggt   13560
tgcctagggt cagagggtgt ggggagatca ggtggcatct aaggggttgg gggaggttat   13620
gggggtaatg aaagggttct aaaattgatt atggtgatga ttgtacagtc ctgcgaatca   13680
actaaaacta ttgaattata cactgtaagt ggatcaattg taaatgaatg ctatttcaat   13740
aaacttgtaa aataccgtat cttatcagct ctttaaggtc atagaggttc ttcgagtttt   13800
ctcttatacc tcacacattt aggcagaatc tccactacct atatcctagt tggtttaatt   13860
```

```
gcaattctttt aatgtatgcg ttgttgctga tacataattt agaaagcttg cttctgtgct    13920 gtgcttttttt caccacctca tctccacaat ttccaagctt gatgtactac agaagtaaga    13980
ataatcttgt tccagtttgc aagttgactc atctgacagt gaaacctcac ccttctgaaa     14040
tctcatcatg aacaaaagtg gggtaactca aacagatagg caaagtccat tgttaaagct    14100
ccttcccttt gttcattgga aggccatcag accccctttc agcctatttg cccttatttt    14160
acatagcatg ctaataagca agttgctgat ttccaaccc accagactag aaacaccaag     14220
ttagaaaggg tgttaagggt gtgctataca gattgaattg tgtctcccca aaattcttat    14280
gttgaaacct taattcccaa catgatagta ttaggaggtg gtgcctttgg gagttaatta    14340
ggctgagttg aggtcataaa ggtgggaccc tcatgatggg atttgtgccc ttataagatg    14400
gaacaccaca gagttgaggc cccttacccc ccatgtaagg gacacaaaga gaaggcagct    14460
acctacaagc caggaagaga gccctcacca gaaaccatcc atgctggcat cttagtgttg    14520
gacttctagc ctccagaact atgagacaat ttctgttgtt taagttgtgc agtctgtggt    14580
attttgttat ggcagcctaa gctgactgag tcatagtagt agcctggaaa aaaggtagct    14640
cttagtctaa ggggacaagg gcactgtggg ggaggggtgc accagcacaa ctttgaccat    14700
ccgaactctg tatagtgatg ttcagctgta cagagcacca acttgatagg gcttagagac    14760
ttcttaggtc acaacatagt ataataaaca atttttcataa tactgtgatt catcaagagg    14820
gttgaatcat tttctgttga aggccataaa gggatttaaa tctgtattag aagtattttc    14880
attcaagata attgaaattg tttacccttt gaaagttgaa ctaagttttg tgctacccag    14940
aatgcctcgt tcctcataat ttctagatgc ctttttgagt gctactctag tttttgtttt    15000
tcaaagcaaa gaggttgaag gtaagttttct actttccttg tcctaaaatt atattttgatt    15060 tacattttga ggcaggatct tgctctgttg cccaggctgg agtgcagtgg tgcagtcata    15120
gctcactgta gcctcgaact cctggactca agctattctc ctggctcaac ccccgagtag    15180
tagggacttc agaccaacag cacctcactt ggctcttttt aaaataattt ttttagagac    15240
agggtctcac tatgtggccc agactagact cagactcctg ggctcaagca gtcctcctgc    15300
cttggactcc caaactgttg gaattacagg catgagccac catgcccagg ctctcttgtc    15360
tttttgataa tagccatcct aagagatgtg aagtgatatc tcattgtcgt tttgatttgc    15420
atttccttga tgattagtga tgtcgagcac cttttaatgt acctgttgac catttgtaag    15480
cagcacgttt ccataactgt ttatcagtta aagtgtactc ttcaaaacta ttgtttttaa    15540
aacattcagg tagcacttaa ctggtaagca gattgttttg tagaatagag aggggctgcc    15600
agtttcagct ttgactatag ctgtgagaag aatgttagtc tcagtccttc tttggaaagc    15660
ctttaaaagg ggctgtttat ttttttctcat acttgtttat tctttcattt aaaacttttt    15720
ttttcttaaa gatgttaatg ttagggccta ggtcacatat aaataagaca tagccctgac    15780
ataagaaact cagagtctat aaagagagac agatggataa acaggagtcc tgtaatacat    15840
gatgtgtgta agatggagag gaagaacctt ttaaaaaagt gaggggtggg ggtggcttca    15900
taaaggaagt gatggttgga gctgagtctt gaaggatcaa caggagtgtc cctggcagaa    15960
gagaaagggc attccagatg gcagaagagc ctgtttacag gcagagaggt tagagattat    16020
gctttcaact tgaattgtaa aatccttaaa agttaggatt acatgggatt taaattaaat    16080
tcctgggtgg tattatatgt tgataacccc ttaaattgtt tcaaactctt tttaaccctg    16140
ttttccagga actcgaatca tttatgacag aaagtttctg ttggatcgtc gcaattctcc    16200
catggctcag accccaccct gccacctgcc caatatccca ggagtcacta gccctggcac    16260
```

```
cttaattgaa gactccaaag tagaagtaaa caatttgaac aacttgaaca atcacgacag    16320
gaaacatgca gttggtaaga gaatggcgat gttggagacc tagagcgtgg ctcttggaat    16380
ttgaatgtct gtttgctgta ggttgagaag ctattgattc ttcagttttg ttttttgttt    16440
tttgtttttt ttgagacaca gtctcattct gtcactgagg ctggagtgca gtggcacaat    16500
ctcagcacac tgcaacctcc gcctcctggg ttcaagcgtt tctcctgcct cagcctcccg    16560
agtagcgggg attacaggcg cctgccacca cgcctggcaa attttttgtat ttttttagtag   16620 agacggggtt tcgccatgtt gcttaggctg ttcttgaact cctgacctca ggtgatccac    16680
ctgcctcagc ctcccaaagt gctaggatta caggtgtgag ccactgtgcc tggccaattc    16740
ttcagttaat aactaatgtt cagttatatg tctctaaggt ttccctcctc ccccaaaggt    16800
ttcttgaaat actctgaaaa ccctgaattc taaatcataa atctgatgta gttggtggga    16860
gaaaagaatc cagaatcagg atgataaacc ccaaaaatga ctctttgaac catgccttaa    16920
ggacttcctg gcctaggctt cattggacta aggataacac acacagaaaa caaaacaatt    16980
tcatagcccc catttccatc accctcaggc aaatagacct tgtttctttt gttttgtttt    17040
gttttttgag acgagtcttg ctctgttgc ccaggctgga gtgcagtggc acgatctcgg    17100
ctcactgcaa gctctggttc ccgggttcac gccattctcc tgcctcagcc tcccaagtag    17160
ctggggctac aggcgcctgc caccacgccc ggctaatttt ttgtattttt tagtagagac    17220
ggggtttcac catgttagcc aggatggtct cgatctcctg acctcgtgat ccgcccgcct    17280
cagcctccca agtgctgag attacaggtg tgagccactg cgcctggccg accttgtttc    17340
ttatatgagt ttcttttata tggtgtgagg aaaagcggta tggtttattt cctctatttt    17400
ccagaactgc gtttaaggtt tacctaaatt acccctcctc caacacattc ttttttttctt   17460 tatcactgta gaagcagaat ggtgcggtag gagtggccag ctcctgaaat attcctcagg    17520
gactgcactt ggtgacccct agatgggggc cagcattccg ctttgtcata tttcagatga    17580 gtttttaat ggacaaagtg ttagtttgga gcagggccaa agtccaaagc ctccagaaga    17640
atgtgctccc ctgagagatg gcaaagagct ccccaagagc tgctgtttag tcatcctgaa    17700
gacaaaggga caatggggat gttttcactt gtgtccttttt ccccaaaact tctccccatg    17760
ggtgatggga ctgccattct tattttttcag attaagacca gccaaagcaa agcagagtaa    17820 ttgtttttaag gcagcagaga gtgggacaat ttgaattact ttttgtctct catttagagg    17880
gaatgacagt taaaactgtt atgcttcttt gtgtacgtgc taaactcttc attttattgg    17940
tcctaactag gggatgatgc tcagttcgag atggacatct gactctcctg caaggattag    18000
aagaaaagca gcaacactga tacttgtgtg cacctgattt ggccaatagg atcaacagtg    18060
aaaagacaga agaggcaata ccagcagtcc ccattacagt ctccacctcc ccgtcttcct    18120
ctgggtgcca aatgatggga agatgagctt catctgacca ttttcttctcc ctgtctcctg    18180 ttccccttcc cagttaaaca ggttagattg aaggcccttg ctgtatttct gtagagctaa    18240
gcagccctta gaggaaaaca gttcaactct gactttccta gttgttttttt tattgagagc    18300 caccctcata ccctgtaatt ttgtcccaaa tcaaatatca acctaccaac aactgcctgg    18360
ctgggaagtc tggggaaggg atacagagct tggtgggcct aacaccattc atattcctta    18420
ccctctgtct ctcctccctg tatcccacct atggttcagt gttgcaagag tctgggcttg    18480
gggtctttaa aaccagcagg gggaaatgat aaaaagagag ctgctttccc ttttaccttg    18540
aggtattcgt ccctcgggac agagcacagc ttgtgcaact ctggtagcgt tacctgtga     18600 cactgttttg aggtccactt cctttctttc ctctgggagg aatgtcttct gtctttggta    18660
```

```
ttatagttca tcttcccatt cttttactta gtgcatttgt gcagatattt ttaactctgt    18720
acatcagaag agagcccttg gtaaccagtt ttgctcttct tctgccactc ctccctgctt    18780
gcatctcgtt gctggcagag tcctcttgta cttcaagaaa gcaaagtgat tttgtctgct    18840
cctagagcag gtccatacca agtaatagag gcacttagc ttccacttgg tgggtaaggc    18900
ctgatcatag tattctgtca gataatgcct aagaatgacc gctgaagaac gttgacccat    18960
ttgagtaccc ggtctcagtc gtcatttta agtccagtga gcattgtggt agttgttctt    19020
agattgcagt tcttatgtt ttgagtttga agttgatttt cagaatgttc ttagaaaaga    19080
actgcatttt tttcctttgt ggatctgctt tgtttggctg ctgggataga taagcatggg    19140
cttaaaaaat gtgttcctcc cagttttctt gcctttcctg ttgtactctg aatttctctc    19200
cctacctccc tcactttctt cctctctcct tcctttcctt cctttttctc taccaggcca    19260
tttttcaaat ttacatcaaa gatacctgaa gtgttggtat ctgagaatat ctgtcactcc    19320
tcttatctga gaagtgacct tttattttta agatgactac agacctattt ttagatatgt    19380
tttcagtaca atttttgaaca gcaactttt aattaaacat cttccagtgt taggaagttg    19440
agaaacgttc ataggcaagt ctgctgttct atgtcaccat cttttgtctc ccctagtccc    19500
ccaggagctc tttcctttcc cctctagttt tgggtgtgca tgtttggagt ttgtagtggg    19560
tggtttgtaa aactggacca ttctgccttg ctatggggttg ttcaagaaag cctcattctt    19620
ttctgtgacc ctttcgcttt tgcattcacc ctccttccca cctacctgtc ctggggctgt    19680
tgagcagcat aataatcccg ggagaatgat tcccctcata gaaagacaaa agcatccatc    19740
ccctcatagt taagtagcca ctggtgtcct gggaatttct ggttggattt ggtgccctga    19800
acttttttat taagaaatca gatcccaggg tgagagtaac aggccatttg gccaagaaag    19860
aaacctgttt gtttttcttt tgaactatga aaagaccctg tttgtgaata tattttagaa    19920
agagaggaag gatgtctgca gaactttgtt ctgttttctg ccacaaaaat gtgaatagtt    19980
cagagtgaaa acctttgtg atggttgatg tctcaggaat aagctggatc tccaatgttt    20040
tggggatgct ttgagtctca aaaaaaattg ataatcagaa aagtaatttt tgtttgtttg    20100
tttaatgtat ccctgttctg tttttaatta aactccaagt ctcattttac atattcttgg    20160
aaaaacctaa gttgctctgt aatttacata agaagcatgc tcaggacctc tttgtacccc    20220
ggggagcctg attctttggg aatgaagctt ttcattcttc atacactggc cttggcatcc    20280
tgtggaattt gacccaacta gcagctagtc agtctgtcag tgagcagaag agtgaactct    20340
tcttgatctt tattgctatg tgtgaaaact tggcttcctc actgaacggt gaggaatgga    20400
tttaaagcat gagctttagt agtatcaaga tgccattttc ctttttcttg ctgtcttggg    20460
gagcttctgc atgtgacccc ctaatcagaa ggcatgtttt tagtatttct tgggagtgtc    20520
agctgtataa tgcagcagct gttcaatccc ttacccttct ctgcaaggac ttccttacag    20580
cttggtgcag ttcttcccca gaggccacca ctactagaca gtctttcttt tatcttatgg    20640
agataaattg gcatttaaaa aataatttca caaggcatga gataaacttt caatagatga    20700
taccttttgtg tcatgcctca tggaattatt tttagaacaa gccagagtcc attgagtggt    20760
ttacctctgc atgtttggag ggaacctcac agatgaaacc cttaatgaat aatgtgtccg    20820
gggttttta gagagaagga gcactcttaa gttaccactt tgagacagct cttaacatct    20880
tagtgaccat ttgtagttttt ctttttatga ggaacccatg cttctatact tgggcggaca    20940
atcgagctta atgagaagtg acttcccttc aaattccaac agcagacatg cattgtcatg    21000
attctgtctt ctttttagtg tggtttattg agttcagcag ttctcatatt ctgtttaaat    21060
```

```
aggtacagca ttttcaaggg cacagataca gagaagctgg ctttctaggt attgggcttc    21120
caagccaaga gttttgtcct tccacctgta ttagttatct attgctgtgt aaaaaattac    21180
cctaaattta gtatgttaaa atagtaaaca ttatctgtca gtttctgtgg gttaagaatt    21240
tgggagtagt ttaacatgat ggttctggcc catggtatca tgaagttaca gtcaagattg    21300 aacagggct gcagtcagct ggagctggag aaaccacttc caagttctct ctttgtggcc     21360
gttggcagga tgcctcagtt tcttcccatg tgggtctctg cgtagggcag catgagtgtc    21420
ctcacaccat gacacctggc ttctccctga gcagctgatt ccagagatca tggggcaggg    21480
ccaggagaaa gctgcagtgc cttttaagac atagtcttgg aaaggacaca ccgtcacttc    21540
ttatcctagt tgttagaagc aagccactaa gttcagcctg cactcaagga gagaggaatt    21600
acacatacct ctaccccaat ggagcagtag caaagaattt atggacatat cttaaaagca    21660
ccacacccca actggggatg aaagtaggtc aacaggagg taggtttaat ctagataagc      21720
tgaaagatag attgctatca aaaacagttc tccaagatgt gcatagccaa actgggatag    21780 aaggcaaaact ccccaaagct acctgctggt tttgagaggg gtggtaagac atggcaattc    21840
ccaggagtag tagaaaataa tatgcctgac taccaacagc tcaagtatgc ttatttgcac    21900
atcctagact tggtgtctgt aagactcagt taccactttt attttcctgt agctaggagt    21960
tagcaaaagg aactgggcc ttccagccga gccactaaac ctgtcttatt tggaatgggg     22020
attgtccagc aaagggagca acatgaatt agatgttaag ctattgagct gaagaaaaga     22080
aagcagttca catttaggtg aaatagatga tgttatcagg aagccaggtt cccaccagag    22140
tcggtgcttg gtacctggtc tctccagtct caacagactc aggtcaggtc tctcacccag    22200
gaagcaacca ctcaataaaa tagagaacat ctgagaatta caaatgtcta tgcttgattg    22260
ctcctctaaa tccagtgcat aggttaaccc tgcatgccca tttcttcctg ggcttcttga    22320
tggcaatgtg ttcttaaata actggtcttg tgttcatgct aaagacaaac ttacatgaag    22380
tttttcagtt taagacattc tagtgaatgg ctgctatgtg tttctggcac tcattcctaa    22440
ccaagtcttt agagatttca gatgacctta aagatgcaat atcttttct ttctttcttt     22500 cttctttttt ttctgagaca agagttgcgc cctgtcgccc aggctggggt gctggagtgc    22560
agtggtgcga tctcagctca ctgcagcctc tgcttcccag gttcaagtgt ttctcctgcc    22620
tcagccttcc gagtagctgg gattacaggc atgtaccact atgcctggct aattttatt     22680 tctatatttt tagtagagat gggtttcat catgtttgcc aggctggtct cgaactcctg     22740
gcctcaagtg atccgcccac ctcagcctcc caaagtgctg ggattacagg cgcgagccac    22800
cgcgcctggc caaagatgca aattcttgtt tggatttatg ctctgcctct tcccagcatt    22860
ttcttatctg tagccctgct tgcttgagag tatacttgga taagaagtat tgctgttgag    22920
ggagctataa gaaaaggatt cttcttccag aagtaaagaa ctcatcttta gagtaccttt    22980
aaatgaattt tgttttctt tcttattttg aggtggattg tcttctctt tttttgggtt      23040 tccagctcac tgggactctc agaccttacc tttccagctc aaacaccatt agttaaattc    23100
cttcattctc attagaatgc agcctgctga gtatgtgggt ttcactgccg gagtccatca    23160
tttagccagt atacatagag gaactgcttc gaatcaaggc aactggtgaa gggcttagca    23220
tgttggcagc aatatcccag agattgaatc tgtttgcatt ttcctcatct aggataacag    23280
ctgcttgaag ccagggctct tagcccttg cattcccctt gagcgaggaa gccacactgc     23340
ctttctgtgt ctggttcaga gctcttcctt cttggcatgt tttctggact acatgcacat    23400
gggcagctat agattaatct gcaaaaccta gtcacttacc tacccataat atctgggaag    23460
```

-continued

```
gtgtggtatt tgttttaaag aaacattgtt tctttgggag ggcagtttct gtctggactt   23520
tgaggtggac ttagttatcc ctacagttct ttaactctca gctttaata aaagatgaaa    23580
tcagatattg atgcagttgg gtcacaattc tttagaatgc ttctaccccca gggccgcttc   23640
ctgttcctag tcatggtttt ccagtttagt agtggagttt cttgaggcta acttacagaa   23700
atttctaact gaaaacttta agagttattg atacttgttt tttcagtcag tcacttacat   23760
cacctagcct actctctgga atttaaattt atttctctag gctggtcctg gaagttgata   23820
acctttttggc aaagcttaga tttaggagaa ggcttgagtc cctgttcagc gggtctgtgg   23880
attctctttg cttatggctc tctgcctgca gccctggcag accatactgt atgtcatgga   23940
tacccagtgg aaatattact gagatgaaac acatttccaa gggtatttaa actctcactc   24000
tgccacctttt ctaagggtgg gaggctggca gagatgctgc aatgcttgat aatcatttgg   24060
ccacactgaa atttccaaag ggagctcttg ccggtgctta aaaccaaaac tcctggacac   24120
ttagaaaatt ccatgaatct agcacaaaat atccattctt gcccaagtgt atccccttc    24180
tctccagctt aatctttttt tttttttttt ttttaaagcc caggccaagg gtactttaa    24240
ctggaaactg ggggaggaggg aagaacacta gcagggagct aagaggcagg ttgctgggta   24300
agccatcctg ctcctacctg gtgcctgtat ctacattgct gagtgctgtg cgccagtgcc   24360
tttccttcat ctgcagatgg agcccatctc tttccacctg ggtgaggaga ccctctgcta   24420
ctccaggggt aaaccttaaa gaaggtgtct tgaagagccc agaggacact cacgtgctaa   24480
ggtgtccatt ttatgcatct ttaaaatatt ttatttaaaa aaaaaaatag ccctgccctg   24540
tcttagtgcc actaacggcc cagttccatc cattctgaat ggaaaagcgg agactgccag   24600
cactttcctt ggtcttccct ttgtctccca tgatgtgttg ttccctcatc cctcccatcc   24660
atttcactgt gtgtggatgg atagcagagg gtaccacgca gtccttgagg cagtcctgtg   24720
tgattccatg atcagttgtt tttgtatttt aactattctt ccaaaccagc agatgtttgg   24780
aaattaagga aaaattaaa ttctcatcaa tggttgctgt tatagttaaa tcagtaaaga   24840
tcttgagtat caacttggtg ttttaatttt taaaaatttt ctggtgaaat cctgctaagg   24900
ttatttcaca tttcaggagt ttcagctggt gggggagatg ggcagaggta agaggcagtt   24960
ggctctttat ctgtcagttc tccacacttg cggagcatgc actttgtcaa tgtggacctg   25020
tgtatgcaaa ggagatggtg ggactctcag ggagcatgac cctggtcctg tgctcaggag   25080
cttgcaggtg aacatgtata tgctgggctg acggcaccca agcatgtcct tctcttaagt   25140
gccagccctg aggaagccca aacaacttttt cctttctcag aagaggggct gcctgtgccc   25200
ctgggagcac tggttagatg cccatcatgc ctgttacctc aaaccaagct gtgctgcatg   25260
agcgtcagat tccctgctgt taactaatcc agcgggtttc atgtattagt cctgagaatg   25320
agaa                                                                 25324
```

<210> SEQ ID NO 26
<211> LENGTH: 3188
<212> TYPE: DNA
<213> ORGANISM: H. sapiens
<220> FEATURE:

<400> SEQUENCE: 26

```
gttgattttc agaatgttct tagaaaagaa ctgcattttt ttcctttgtg gatctgcttt      60
gtttggctgc tgggatagat aagcatgggc ttaaaaaatg tgttcctccc agttttcttg     120
cctttcctgt tgtactctga atttctctcc ctacctccct cacttcttc ctctctcctt     180
cctttccttc cttttttctct accaggccat ttttcaaatt tacatcaaag ataccgaag    240
```

```
tgttggtatc tgagaatatc tgtcactcct cttatctgag aagtgacctt ttattttaa    300 gatgactaca gacctatttt tagatatgtt ttcagtacaa ttttgaacag caactttta    360 attaaacatc ttccagtgtt aggaagttga gaaacgttca taggcaagtc tgctgttcta    420
tgtcaccatc ttttgtctcc cctagtcccc caggagctct ttcctttccc ctctagtttt    480
gggtgtgcat gtttggagtt tgtagtgggt ggtttgtaaa actggaccat tctgccttgc    540
tatgggttgt tcaagaaagc ctcattcttt tctgtgaccc tttcgctttt gcattcaccc    600
tccttcccac ctacctgtcc tggggcagtt gagcagcata ataatcccgg gagaatgatt    660
cccctcatag aaagacaaaa gcatccatcc cctcatagtt aagtagccac tggtgtcctg    720
ggaatttctg gttggatttg gtgccctgaa cttttttatt aagaaatcag atcccagggt    780
gagagtaaca ggccatttgg ccaagaaaga aacctgtttg tttttctttt gaactatgaa    840
aagaccctgt ttgtgaatat atttagaaa gagaggaagg atgtctgcag aactttgttc    900
tgttttctgc cacaaaatg tgaatagttc agagtgaaaa ccttttgtga tggttgatgt    960
ctcaggaata agctggatct ccaatgtttt ggggatgctt tgagtctcaa aaaaattga    1020 taatcagaaa agtaattttt gtttgtttgt ttaatgtacc cctgttctgt ttttaattaa    1080
actccaagtc tcatttaca tattcttgga aaaacctaag ttgcgctgta atttacataa    1140
gaagcatgct caggacctct ttgtaccccg gggagcctga ttctttggga atgaagcttt    1200
tcattcttca tacactggcc ttggcatcct gtggaatttg acccaactag cagctagtca    1260
gtctgtcagt gagcagaaga gtgaactctt cttgatcttt attgctatgt gtgaaaactt    1320
ggcttcctca ctgaacggtg aggaatggat ttaaagcatg agctttagta gtatcaagat    1380 gccatttcc ttttcttgc tgtcttgggg agcttctgca tgtgaccccc taatcagaag    1440
gcatgttttt agtatttctt gggagtgtca gctgtataat gcagcagctg ttcaatccct    1500 taccttctc tgcaaggact tccttacagc ttggtgcagt tcttccag aggccaccac    1560 tactagacag tcttctttt atcttatgga gataaattgg catttaaaaa ataatttcac    1620
aaggcatgag ataaactttc aatagatgat accttgtgt catgcctcat ggaattattt    1680
ttagaacaag ccagagtcca ttgagtggtt tacctctgca tgtttggagg gaacctcaca    1740
gatgaaaccc ttaatgaata atgtgtccgg ggttttttag agagaaggag cactcttaag    1800
ttaccacttt gagacagctc ttaacatctt agtgaccatt tgtagtttc ttttatgag    1860 gaacccatgc ttctatactt gggcggacaa tcgagcttaa tgagaagtga cttcccttca    1920
aattccaaca gcagacatgc attgtcatga ttctgtcttc tttttagtgt ggtttattga    1980
gttcagcagt tctcatattc tgtttaaata ggtacagcat tttcaagggc acagatacag    2040
agaagctggc tttctaggta ttgggcttcc aagccaagag ttttgtcctt ccacctgtat    2100
tagttatcta ttgctgtgta aaaaattacc ctaaatttag tatgttaaaa tagtaaacat    2160
tatctgtcag tttctgtggg ttaagaattt gggagtagtt taacatgatg gttctggccc    2220
atggtatcat gaagttacag tcaagattga acagggctg cagtcagctg agctggaga    2280 aaccacttcc aagttctctc tttgtggccg ttggcaggat gcctcagttt cttcccatgt    2340
gggtctctgc gtagggcagc atgagtgtcc tcacaccatg acacctggct tctccctgag    2400
cagctgattc cagagatcat ggggcagggc caggagaaag ctgcagtgcc ttttaagaca    2460
tagtcttgga aaggacacac cgtcacttct tatcctagtt gttagaagca agccactaag    2520
ttcagcctgc actcaaggag agaggaatta cacatacctc taccccaatg gagcagtagc    2580
aaagaattta tggacatatc ttaaaagcac cacaccccaa ctggggatga agtaggtca    2640
```

```
acagggaggt aggtttaatc tagataagct gaaagataga ttgctatcaa aaacagttct    2700
ccaagatgtg catagccaaa ctgggataga aggcaaactc cccaaagcta cctgctggtt    2760
ttgagagggg tggtaagaca tggcaattcc caggagtagt agaaaataat atgcctgact    2820
accaacagct caagtatgct tatttgcaca tcctagactt ggtgtctgta agactcagtt    2880
accactttta ttttcctgta gctaggagtt agcaaaagga actggggcct tccagccgag    2940
ccactaaacc tgtcttattt ggaatgggga ttgtccagca aagggagcaa acatgaatta    3000
gatgttaagc tattgagctg aagaaaagaa agcagttcac atttaggtga aatagatgat    3060
gttatcagga agccaggttc ccaccagagt cggtgcttgg tacctggtct ctccagtctc    3120
aacagactca ggtcaggtct ctcacccagg aagcaaccac tcaataaaat agagaacatc    3180
tgagaatt                                                              3188

<210> SEQ ID NO 27
<211> LENGTH: 1835
<212> TYPE: DNA
<213> ORGANISM: H. sapiens
<220> FEATURE:

<400> SEQUENCE: 27
ctccaagatg tgcatagcca aactgggata gaaggcaaac tccccaaagc tacctgctgg      60
ttttgagagg ggtggtaaga catggcaatt cccaggagta gtagaaaata atatgcctga    120
ctaccaacag ctcaagtatg cttatttgca catcctagac ttggtgtctg taagactcag    180
ttaccacttt tattttcctg tagctaggag ttagcaaaag gaactggggc cttccagccg    240
agccactaaa cctgtcttat ttggaatggg gattgtccag cgaagggagc aaacatgaat    300
tagatgttaa gctattgagc tgaagaaaag aaagcagttc acatttaggt gaaatagatg    360
atgttatcag gaagccaggt tcccaccaga gtcggtgctt ggtacctggt ctctccagtc    420
tcaacagact caggtcaggt ctctcaccca ggaagcaacc actcaataaa atagagaaca    480
tctgagaatt acaaatgtct atgcttgatt gctcctctaa atccagtgca taggttaacc    540
ctgcatgccc atttcttcct gggcttcttg atggcaatgt gttctaataa ctggtcttgt    600
gttcatgcta aagacaaact tacatgaagt ttttcagttt aagacattct agtgaatggc    660
tgctatgtgt ttctggcact cattcctaac caagtcttta gagatttcag atgaccttaa    720
agatgcaata tctttttctt tctttcttc tttcttttt tctgagacaa gagttgcgcc    780
ctgtcgccca gactggggtg ctggagtgca gtggtgcgat ctcagctcac tgcagcctct    840
gcttcccagg ttcaagtgtt tctcctgcct cagccttccg agtagctgga attacaggca    900
tgtaccacta tgcctggcta atttttttatt tctatatttt tagtagagat ggggtttcat    960
catgtttgcc aggctggtct cgaactcctg gcctcaagtg atccgcccac ctcagcctcc   1020
caaagtgctg ggattacagg cgcgagccac cgcgcctggc caaagatgca aattcttgtt   1080
tggatttatg ctctgcctct tcccagcatt ttcttatctg tagccctgct tgcttgagag   1140
tatacttgga taagaagtat tgctgttgag ggagctataa gaaaaggatt cttcttccag   1200
aagtaaagaa ctcatcttta gagtaccttt aaatgaattt tgttttttctt tcttattttg   1260 aggtggattg tcttctctt ttttttgggtt tccagctcac tgggactctc agaccttacc   1320
tttccagctc aaacaccatt agttaaattc cttcattctc attagaatgc agcctgctga   1380
gtatgtgggt ttcactgccg gagtccatca tttagccagt atacatagag gaactgcttc   1440
gaatcaaggc aactggtgaa gggcttagca tgttggcagc aatatcccag agattgaatc   1500
```

```
tgtttgcatt ttcctcatct aggataacag ctgcttgaag ccagggctct tagccctttg    1560
cattcccctt gagcgaggaa gccacactgc ctttctgtgt ctggttcaga gctcttcctt    1620
cttggcatgt tttctggact acatgcacat gggcagctat agattaatct gcaaaaccta    1680
gtcacttacc tacccataat atctgggaag gtgtggtatt tgttttaaag aaacattgtt    1740
tctttgggag ggcagtttct gtctggactt tgaggtggac ttagttatcc ctacagttct    1800
ttaactctca gcttttaat aaaagatgaa atcag                                1835

<210> SEQ ID NO 28
<211> LENGTH: 908
<212> TYPE: DNA
<213> ORGANISM: H. sapiens
<220> FEATURE:
<221> NAME/KEY: unsure
<222> LOCATION: 754
<223> OTHER INFORMATION: unknown

<400> SEQUENCE: 28
gcctacagtt ctttaactct cagcttttaa taaaagatga atcagatat gatgcagtgg      60 gtcacaattc tttagaatgc ttctaccccca gggccgcttc ctgttcctag tcatggtttt   120
ccagtttagt agtggagttt cttgaggcta acttacagaa atttctaact gaaaacttta   180
agagttattg atactgtttt tttcagtcag tcacttacat cacctagcct actctctgga   240
atttaaattt atttctctag gctggtcctg gaagttgata acctttggca aagcttagat   300
ttaggagaag gcttgagtcc ctgttcagcg ggtctgtgga ttctcttgct tatggctctc   360
tgcctgcagc cctggcagac catactgtat gtcatggata cccagtggaa atattactga   420
gatgaaacac atttccaagg gtatttaaac tctcactctg ccaccttct aagggtggga   480 ggctggcaga gatgctgcaa tgcttgataa tcatttggcc acactgaaat tccaaaggg    540 agctcttgcc ggtgcttaaa accaaaactc ctggacactt agaaaattcc atgaatctag   600
cacaaaatat ccattcttgc ccaagtgtat ccccttctc tccaggctta atcttttttt    660
tttttttaaa gaccagggca gggtacttta actggaactg cggggggag aaccttaggg    720 agtcagaggc ggtgcggtag cactgtctac ctgngcccgt ttattgcgat gcgggcgggc   780
ttcttattgg agggcatctc ccgggagaac cgtccggact aaggtgaaca ggacgcgctt   840
ggttatttta caacggtcg ggaagagttc ctagagctag cgtatctctg tgtggacact   900
aattaacg                                                             908

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
gccatgggag aattgcgacg                                                 20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
tttggagtct tcaattaagg                                                 20
```

```
<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
tctactttgg agtcttcaat                                               20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
gtctgtagtc atcttaaaaa                                               20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
acttctactt tggagtcttc                                               20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
tagaccgcag gagctgcgaa                                               20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
agtgattctc aaactgcaga                                               20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
tcttctgatc catggccacc                                               20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 37
tcagcactat ctgttgaaaa                                               20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
attcgagttc ctggaaaaca                                               20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
ttctcttacc aactgcatgt                                               20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
gcatcatccc ctagttagga                                               20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
cctcaggcgg acggaaaagc                                               20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
cgggcgtggt gcaatagtca                                               20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
attcgagttc ctcccggtgt                                               20

<210> SEQ ID NO 44
<211> LENGTH: 20
<212> TYPE: DNA
```

```
<213> ORGANISM: Artificial Sequence
<220> FEATURE:
<223> OTHER INFORMATION: Antisense Oligonucleotide

<400> SEQUENCE: 44
gaaactttct gtcataaatg                                               20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
caacagaaac tttctgtcat                                               20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
gtgccagggc tagtgactcc                                               20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
attgttcaag ttgttcaaat                                               20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
tgcatgtttc ctgtcgtgat                                               20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
ccaactgcat gtttcctgtc                                               20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
gcatcatccc caactgcatg                                               20
```

```
<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
gtccatctcg aactgagcat                                              20

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52
gcaggagagt cagatgtcca                                              20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53
aagtatcagt gttgctgctt                                              20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
tcaggtgcac acaagtatca                                              20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
atcatttggc acccagagga                                              20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
agctcatctt cccatcattt                                              20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 57
acagggagaa gaaatggtca                                              20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
taacctgttt aactgggaag                                              20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
cagaaataca gcaagggcct                                              20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
ctctaagggc tgcttagctc                                              20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
agagttgaac tgttttcctc                                              20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
caaaattaca gggtatgagg                                              20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
aagaccccaa gcccagactc                                              20

<210> SEQ ID NO 64
<211> LENGTH: 20
<212> TYPE: DNA
```

```
<213> ORGANISM: Artificial Sequence
<220> FEATURE:
<223> OTHER INFORMATION: Antisense Oligonucleotide

<400> SEQUENCE: 64
atttccccct gctggtttta                                               20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
aagggaaagc agctctcttt                                               20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
agagttgcac aagctgtgct                                               20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
agtggacctc aaaacagtgt                                               20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
tctgcacaaa tgcactaagt                                               20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
aaaactggtt accaagggct                                               20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
gaagagcaaa actggttacc                                               20
```

```
<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
ccagcaacga gatgcaagca                                              20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
agtacaagag gactctgcca                                              20

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
tggtatggac ctgctctagg                                              20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
gtgcctctat tacttggtat                                              20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
ttcttaggca ttatctgaca                                              20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
agcggtcatt cttaggcatt                                              20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 77
acgactgaga ccgggtactc                                               20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
acaactacca caatgctcac                                               20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79
attctgaaaa tcaacttcaa                                               20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
tcccagcagc caaacaaagc                                               20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
atttgaaaaa tggcctggta                                               20

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82
acacttcagg tatctttgat                                               20

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
agataccaac acttcaggta                                               20

<210> SEQ ID NO 84
<211> LENGTH: 20
<212> TYPE: DNA
```

```
<213> ORGANISM: Artificial Sequence
<220> FEATURE:
<223> OTHER INFORMATION: Antisense Oligonucleotide

<400> SEQUENCE: 84
acagatattc tcagatacca                                              20

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
atgtttaatt aaaaagttgc                                              20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
acactggaag atgtttaatt                                              20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
cagttttaca aaccacccac                                              20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88
aagaatgagg ctttcttgaa                                              20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
cagaaaagaa tgaggctttc                                              20

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 90
tgaatgcaaa agcgaaaggg                                              20
```

```
<210> SEQ ID NO 91
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 91
tcccgggatt attatgctgc                                                    20

<210> SEQ ID NO 92
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 92
gaaattccca ggacaccagt                                                    20

<210> SEQ ID NO 93
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 93
aaccagaaat tcccaggaca                                                    20

<210> SEQ ID NO 94
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 94
caaatccaac cagaaattcc                                                    20

<210> SEQ ID NO 95
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 95
ccaaatggcc tgttactctc                                                    20

<210> SEQ ID NO 96
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 96
aacaaacagg tttctttctt                                                    20

<210> SEQ ID NO 97
<211> LENGTH: 20
<212> TYPE: DNA
<213> ORGANISM: Artificial Sequence
<220> FEATURE:
<223> OTHER INFORMATION: Antisense Oligonucleotide
```

<400> SEQUENCE: 97
cttttcatag ttcaaaagaa                                              20

<210> SEQ ID NO 98
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 98
cagacatcct tcctctcttt                                              20

<210> SEQ ID NO 99
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 99
ttgtggcaga aaacagaaca                                              20

<210> SEQ ID NO 100
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 100
aactattcac atttttgtgg                                              20

<210> SEQ ID NO 101
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 101
tggagatcca gcttattcct                                              20

<210> SEQ ID NO 102
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 102
aagaatgaaa agcttcattc                                              20

<210> SEQ ID NO 103
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 103
tttaaatcca ttcctcaccg                                              20

<210> SEQ ID NO 104
<211> LENGTH: 20
<212> TYPE: DNA

```
<213> ORGANISM: Artificial Sequence
<220> FEATURE:
<223> OTHER INFORMATION: Antisense Oligonucleotide

<400> SEQUENCE: 104
ataactaata caggtggaag                                                   20

<210> SEQ ID NO 105
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 105
ggtcatctga aatctctaaa                                                   20

<210> SEQ ID NO 106
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 106
gcctcccacc cttagaaagg                                                   20

<210> SEQ ID NO 107
<211> LENGTH: 598
<212> TYPE: DNA
<213> ORGANISM: M. musculus
<220> FEATURE:

<400> SEQUENCE: 107
aaattctttc cttctggttc ttccaccggg ccatttccca catctgcatc agaagagatg       60
cctcccatgt tagtatctga taatatcagt ctctccttat cagaggagag acctttatt      120 tttaagatga ctacagacct attttagat aagttttcag tacaattttg aactacaact      180 ttttttaacaa acatcttcc agtattggga aggttatttt aaaagaaaa aaaaacaatg      240 tttgtaggca agtccactgc tgtcactgtc ctttgtctcc catagcccct tctgagctct      300
cctgtgccct tgagctttgg ggctatttgg agtgtagaat gggtgttttg tgaaactgga      360
ccagtctgcc ttgccatgag ctgttgaaga aaactccgtg tccctctcat ccgaaggtac      420
acgatcacaa gctacgccac acatagaaga gcagttcaag agactatcag cgaaggaacg      480
caacgcgcag ccacagaggc agcaagaaag gaagccgcac gaaaaaacac gagtgagaga      540
gtgaagaata cgaagcacag gaaagtccat ggagaaaagg aacgagaaag acaaaagg       598

<210> SEQ ID NO 108
<211> LENGTH: 431
<212> TYPE: DNA
<213> ORGANISM: M. musculus
<220> FEATURE:

<400> SEQUENCE: 108
cgcatcggga cgaccgggcg agagcaggcg agttgagagc cgagcgtgaa gagccgccgc       60
cgccgccgct gctgcacaaa gcctcgagcc cgcgtcggag ccatgtccgc gtcggccggt      120
ggtagccacc agcccagcca gagccgcgcc atccccacgc gcaccgtggc tatcagcgac      180
gccgcgcagc tacctcagga ctactgcacc acgcccgggg ggacgctgtt ctccacaacg      240
ccgggaggaa cacgaatcat ttatgaccga aagtttctgt tggaccgtcg caattctccc      300
```

-continued

```
atggcgcaga ccccaccttg ccatctgccc aatatccctg gagtcaccag tcctggcgcc    360
ttaattgaag actccaaaga gaagtgaaca acttaaacaa cctgaacaat catgacagga    420
agcatgcagt t                                                         431
```

```
<210> SEQ ID NO 109
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 109
tctcaactcg cctgctctcg                                                 20
```

```
<210> SEQ ID NO 110
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 110
ggctcctcac gctcggctct                                                 20
```

```
<210> SEQ ID NO 111
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 111
tcgaggcttt gtgcagcagc                                                 20
```

```
<210> SEQ ID NO 112
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 112
gctggtggct accaccggcc                                                 20
```

```
<210> SEQ ID NO 113
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 113
gctgggctgg tggctaccac                                                 20
```

```
<210> SEQ ID NO 114
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 114
gtcgctgata gccacggtgc                                                 20
```

```
<210> SEQ ID NO 115
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 115
agtcctgagg tagctgcgcg                                               20

<210> SEQ ID NO 116
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 116
gtggtgcagt agtcctgagg                                               20

<210> SEQ ID NO 117
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 117
cataaatgat tcgtgttcct                                               20

<210> SEQ ID NO 118
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 118
tcggtcataa atgattcgtg                                               20

<210> SEQ ID NO 119
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 119
aactttcggt cataaatgat                                               20

<210> SEQ ID NO 120
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 120
caacagaaac tttcggtcat                                               20

<210> SEQ ID NO 121
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 121
```
cggtccaaca gaaactttcg                                           20

<210> SEQ ID NO 122
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 122
gggagaattg cgacggtcca                                           20

<210> SEQ ID NO 123
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 123
tctgcgccat gggagaattg                                           20

<210> SEQ ID NO 124
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 124
caggactggt gactccaggg                                           20

<210> SEQ ID NO 125
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 125
ttcacttcta ctttggagtc                                           20

<210> SEQ ID NO 126
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 126
aaactgagcc tcatccccaa                                           20

<210> SEQ ID NO 127
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 127
atctcaaact gagcctcatc                                           20

<210> SEQ ID NO 128
<211> LENGTH: 20
<212> TYPE: DNA
<213> ORGANISM: Artificial Sequence
<220> FEATURE:

```
<223> OTHER INFORMATION: Antisense Oligonucleotide

<400> SEQUENCE: 128
gatgtccatc tcaaactgag                                               20

<210> SEQ ID NO 129
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 129
tggcagtagt cagatgtcca                                               20

<210> SEQ ID NO 130
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 130
ggctgctcca cgaggcctcc                                               20

<210> SEQ ID NO 131
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 131
tgggccagtc aggtgcacac                                               20

<210> SEQ ID NO 132
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 132
ctgtacactg tgttcctact                                               20

<210> SEQ ID NO 133
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 133
atgtgatcag acagtgcaca                                               20

<210> SEQ ID NO 134
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 134
cgggaagatg tgatcagaca                                               20

<210> SEQ ID NO 135
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 135
ttcttctgtg gactgtcagc                                               20

<210> SEQ ID NO 136
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 136
gtgctgcttg gagactgccc                                               20

<210> SEQ ID NO 137
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 137
tacaagcaga ggtgctgctt                                               20

<210> SEQ ID NO 138
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 138
ggcactaaac ctccttcacc                                               20

<210> SEQ ID NO 139
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 139
acacaatggg cactaaacct                                               20

<210> SEQ ID NO 140
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 140
gagcccagga acacaatggg                                               20

<210> SEQ ID NO 141
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 141
```
aatgtccccc acatccagcg                                                  20

<210> SEQ ID NO 142
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 142
ctgaggacaa atgtccccca                                                  20

<210> SEQ ID NO 143
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 143
caggactgtg ctccagagct                                                  20

<210> SEQ ID NO 144
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 144
ggaggtacag gactgtgctc                                                  20

<210> SEQ ID NO 145
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 145
gaggctgctg tcacatgtcc                                                  20

<210> SEQ ID NO 146
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 146
aagccttcct cccagagaaa                                                  20

<210> SEQ ID NO 147
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 147
tatcacaccc aagacaagac                                                  20

<210> SEQ ID NO 148
<211> LENGTH: 20
<212> TYPE: DNA
<213> ORGANISM: Artificial Sequence
<220> FEATURE:

```
<223> OTHER INFORMATION: Antisense Oligonucleotide

<400> SEQUENCE: 148
gatgatgagc tatcacaccc                                           20

<210> SEQ ID NO 149
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 149
cccttcagga gggcttaaaa                                           20

<210> SEQ ID NO 150
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 150
cagacaggca aagaccagct                                           20

<210> SEQ ID NO 151
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 151
tgcctacggg atgcaggtag                                           20

<210> SEQ ID NO 152
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 152
cttctgctct aaaagcagac                                           20

<210> SEQ ID NO 153
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 153
caggccaagg tgttggcact                                           20

<210> SEQ ID NO 154
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 154
gctgagagca ggctggactc                                           20

<210> SEQ ID NO 155
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 155
tctcaggcag accgctgaga                                              20

<210> SEQ ID NO 156
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 156
gcccctgatg tattctcagg                                              20

<210> SEQ ID NO 157
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 157
tcagaggccc ctgatgtatt                                              20

<210> SEQ ID NO 158
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 158
gtcctcttca gaggcccctg                                              20

<210> SEQ ID NO 159
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 159
tgcacggcgg ctcagtcctc                                              20

<210> SEQ ID NO 160
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 160
ctggctgcac ggcggctcag                                              20

<210> SEQ ID NO 161
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 161
```

```
aaaaccatga cccccgaggc                                          20

<210> SEQ ID NO 162
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 162
tacacctggt tttaaaacca                                          20

<210> SEQ ID NO 163
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 163
acacccaacg taaggtacac                                          20

<210> SEQ ID NO 164
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 164
tgcaggacac ccaacgtaag                                          20

<210> SEQ ID NO 165
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 165
aaactcaagg tatagtaacc                                          20

<210> SEQ ID NO 166
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 166
aagtcgactt taaactcaag                                          20

<210> SEQ ID NO 167
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 167
taagaggaag tcgactttaa                                          20

<210> SEQ ID NO 168
<211> LENGTH: 20
<212> TYPE: DNA
<213> ORGANISM: Artificial Sequence
<220> FEATURE:
```

```
<223> OTHER INFORMATION: Antisense Oligonucleotide

<400> SEQUENCE: 168
ctgtgctgct ctctcagcag                                          20

<210> SEQ ID NO 169
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 169
cactgtctta gcctgtgctg                                          20

<210> SEQ ID NO 170
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 170
tggaaaatgg cccggtggaa                                          20

<210> SEQ ID NO 171
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 171
tactaacatg ggaggcatct                                          20

<210> SEQ ID NO 172
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 172
tgataaggag agactgatat                                          20

<210> SEQ ID NO 173
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 173
taaaaggtct ctcctctgat                                          20

<210> SEQ ID NO 174
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 174
taaaaataaa aggtctctcc                                          20

<210> SEQ ID NO 175
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 175
aacttatcta aaaataggtc                                            20

<210> SEQ ID NO 176
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 176
tgtactgaaa acttatctaa                                            20

<210> SEQ ID NO 177
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 177
atactggaag atgttttgtt                                            20

<210> SEQ ID NO 178
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 178
ataaccttcc caatactgga                                            20

<210> SEQ ID NO 179
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 179
acagctcatg gcaaggcaga                                            20

<210> SEQ ID NO 180
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 180
aactgctctt ctatgtgtgg                                            20

<210> SEQ ID NO 181
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 181
```
tcgctgatag tctcttgaac                                                  20

<210> SEQ ID NO 182
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 182
ggctcttcac gctcggctct                                                  20

<210> SEQ ID NO 183
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 183
ggctcgtggc tttgtgcagc                                                  20

<210> SEQ ID NO 184
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 184
tggtgtccac caccggccga                                                  20

<210> SEQ ID NO 185
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 185
tggctgggct ggtgtccacc                                                  20

<210> SEQ ID NO 186
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 186
tctggctggg ctggtgtcca                                                  20

<210> SEQ ID NO 187
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 187
gaatggcgcg gctctggctg                                                  20

<210> SEQ ID NO 188
<211> LENGTH: 20
<212> TYPE: DNA
<213> ORGANISM: Artificial Sequence
<220> FEATURE:

-continued

```
<223> OTHER INFORMATION: Antisense Oligonucleotide

<400> SEQUENCE: 188
ctaatagcca cggtgcgtgt                                                      20

<210> SEQ ID NO 189
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 189
gtcgctaata gccacggtgc                                                      20

<210> SEQ ID NO 190
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 190
gctgcgtcgc taatagccac                                                      20

<210> SEQ ID NO 191
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 191
tgaggtagct gcgctgcgtc                                                      20

<210> SEQ ID NO 192
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 192
cctgaggtag ctgcgctgcg                                                      20

<210> SEQ ID NO 193
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 193
tagtcctgag gtagctgcgc                                                      20

<210> SEQ ID NO 194
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 194
agtagtcctg aggtagctgc                                                      20

<210> SEQ ID NO 195
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 195
tgcagtagtc ctgaggtagc                                              20

<210> SEQ ID NO 196
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 196
ggtgcagtag tcctgaggta                                              20

<210> SEQ ID NO 197
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 197
cgtggtgcag tagtcctgag                                              20

<210> SEQ ID NO 198
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 198
ggcgtggtgc agtagtcctg                                              20

<210> SEQ ID NO 199
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 199
ggtgttgtgg agaacagcgt                                              20

<210> SEQ ID NO 200
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 200
ctcccggtgt tgtggagaac                                              20

<210> SEQ ID NO 201
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 201
```

-continued

```
gttcctcccg gtgttgtgga                                          20

<210> SEQ ID NO 202
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 202
aaactttcgg tcataaatga                                          20

<210> SEQ ID NO 203
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 203
agaaactttc ggtcataaat                                          20

<210> SEQ ID NO 204
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 204
acagaaactt tcggtcataa                                          20

<210> SEQ ID NO 205
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 205
aacagaaact ttcggtcata                                          20

<210> SEQ ID NO 206
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 206
tccaacagaa actttcggtc                                          20

<210> SEQ ID NO 207
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 207
ggtccaacag aaactttcgg                                          20

<210> SEQ ID NO 208
<211> LENGTH: 20
<212> TYPE: DNA
<213> ORGANISM: Artificial Sequence
<220> FEATURE:
```

<223> OTHER INFORMATION: Antisense Oligonucleotide

<400> SEQUENCE: 208
gcgacggtcc aacagaaact                                           20

<210> SEQ ID NO 209
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 209
ttgcgacggt ccaacagaaa                                           20

<210> SEQ ID NO 210
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 210
gaattgcgac ggtccaacag                                           20

<210> SEQ ID NO 211
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 211
gagaattgcg acggtccaac                                           20

<210> SEQ ID NO 212
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 212
tgggagaatt gcgacggtcc                                           20

<210> SEQ ID NO 213
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 213
cgccatggga gaattgcgac                                           20

<210> SEQ ID NO 214
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 214
tgcgccatgg gagaattgcg                                           20

<210> SEQ ID NO 215

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 215
gtctgcgcca tgggagaatt                                                     20

<210> SEQ ID NO 216
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 216
attgggcaga tggcaaggtg                                                     20

<210> SEQ ID NO 217
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 217
ggtgactcca gggatattgg                                                     20

<210> SEQ ID NO 218
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 218
ggactggtga ctccagggat                                                     20

<210> SEQ ID NO 219
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 219
cgccaggact ggtgactcca                                                     20

<210> SEQ ID NO 220
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 220
ggagtcttcc attaaggcgc                                                     20

<210> SEQ ID NO 221
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 221
```

```
ttggagtctt ccattaaggc                                                 20

<210> SEQ ID NO 222
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 222
tactttggag tcttccatta                                                 20

<210> SEQ ID NO 223
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 223
cacttctact ttggagtctt                                                 20

<210> SEQ ID NO 224
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 224
tgttcacttc tactttggag                                                 20

<210> SEQ ID NO 225
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 225
caagttgttc acttctactt                                                 20

<210> SEQ ID NO 226
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 226
gttcaagttg ttcacttcta                                                 20

<210> SEQ ID NO 227
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 227
tcaggttgtt caagttgttc                                                 20

<210> SEQ ID NO 228
<211> LENGTH: 20
<212> TYPE: DNA
<213> ORGANISM: Artificial Sequence
<220> FEATURE:
```

```
<223> OTHER INFORMATION: Antisense Oligonucleotide

<400> SEQUENCE: 228
tgttcaggtt gttcaagttg                                              20

<210> SEQ ID NO 229
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 229
gattgttcag gttgttcaag                                              20

<210> SEQ ID NO 230
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 230
cgtgattgtt caggttgttc                                              20

<210> SEQ ID NO 231
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 231
tgtcgtgatt gttcaggttg                                              20

<210> SEQ ID NO 232
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 232
ttcctgtcgt gattgttcag                                              20

<210> SEQ ID NO 233
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 233
gcttcctgtc gtgattgttc                                              20

<210> SEQ ID NO 234
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 234
gtgcttcctg tcgtgattgt                                              20

<210> SEQ ID NO 235
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 235
actgcgtgct tcctgtcgtg                                           20

<210> SEQ ID NO 236
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 236
caactgcgtg cttcctgtcg                                           20

<210> SEQ ID NO 237
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 237
ccccaactgc gtgcttcctg                                           20

<210> SEQ ID NO 238
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 238
atccccaact gcgtgcttcc                                           20

<210> SEQ ID NO 239
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 239
ctcatcccca actgcgtgct                                           20

<210> SEQ ID NO 240
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 240
gcctcatccc caactgcgtg                                           20

<210> SEQ ID NO 241
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 241
```

```
gagcctcatc cccaactgcg                                                   20

<210> SEQ ID NO 242
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 242
ctgagcctca tccccaactg                                                   20

<210> SEQ ID NO 243
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 243
tcaaactgag cctcatcccc                                                   20

<210> SEQ ID NO 244
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 244
cagcagggtc agatgtccat                                                   20

<210> SEQ ID NO 245
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 245
ccttcgacac tgcagcaggg                                                   20

<210> SEQ ID NO 246
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 246
gccgccttcg acactgcagc                                                   20

<210> SEQ ID NO 247
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 247
gtgcacacgg gccgtgtcag                                                   20

<210> SEQ ID NO 248
<211> LENGTH: 20
<212> TYPE: DNA
<213> ORGANISM: Artificial Sequence
<220> FEATURE:
```

```
<223> OTHER INFORMATION: Antisense Oligonucleotide

<400> SEQUENCE: 248
ccagtcaggt gcacacgggc                                           20

<210> SEQ ID NO 249
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 249
ggtccagtca ggtgcacacg                                           20

<210> SEQ ID NO 250
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 250
tactggtcca gtcaggtgca                                           20

<210> SEQ ID NO 251
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 251
tcctactggt ccagtcaggt                                           20

<210> SEQ ID NO 252
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 252
gtgttcctac tggtccagtc                                           20

<210> SEQ ID NO 253
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 253
cacggtgttc ctactggtcc                                           20

<210> SEQ ID NO 254
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 254
tgtacacggt gttcctactg                                           20

<210> SEQ ID NO 255
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 255
tctctgtaca cggtgttcct                                                    20

<210> SEQ ID NO 256
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 256
cttctctgta cacggtgttc                                                    20

<210> SEQ ID NO 257
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 257
tggagcttct ctgtacacgg                                                    20

<210> SEQ ID NO 258
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 258
actggagctt ctctgtacac                                                    20

<210> SEQ ID NO 259
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 259
ctgctagcct ctggatttga                                                    20

<210> SEQ ID NO 260
<211> LENGTH: 19
<212> TYPE: RNA
<213> ORGANISM: Artificial Sequence
<220> FEATURE:
<223> OTHER INFORMATION: Synthetic Oligonucleotide

<400> SEQUENCE: 260
cgagaggcgg acgggaccg                                                     19

<210> SEQ ID NO 261
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(19)
```

```
<223> OTHER INFORMATION: bases at these positions are RNA

<400> SEQUENCE: 261
cgagaggcgg acgggaccgt t                                          21

<210> SEQ ID NO 262
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 1, 2, 3, 5, 6, 7, 8, 10, 11, 12, 13, 14, 16, 18, 19
<223> OTHER INFORMATION: bases at these positions are RNA

<400> SEQUENCE: 262
cggtcccgtc cgcctctcgt t                                          21

<210> SEQ ID NO 263
<211> LENGTH: 19
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 1, 2, 3, 5, 6, 7, 8, 10, 11, 12, 13, 14, 16, 18, 19
<223> OTHER INFORMATION: bases at these positions are RNA

<400> SEQUENCE: 263
cggtcccgtc cgcctctcg                                             19
```

MODULATION OF EIF4E-BP2 EXPRESSION

CROSS REFERENCE TO RELATED APPLICATIONS

This application is a divisional application of U.S. patent application Ser. No. 11/042,889 filed Jan. 24, 2005, now U.S. Pat. No. 7,468,431 which claims priority to U.S. Application Ser. No. 60/538,752, filed on Jan. 22, 2004, both of which are incorporated herein by reference in their entirety.

SEQUENCE LISTING

The present application is being filed along with a Sequence Listing in electronic format. The Sequence Listing is provided as a file entitled RTS0731USC1SEQ.txt, created on Nov. 19, 2008 which is 100 Kb in size. The information in the electronic format of the sequence listing is incorporated herein by reference in its entirety.

FIELD OF THE INVENTION

The present invention provides compositions and methods for modulating the expression of eIF4E-BP2. In particular, this invention relates to antisense compounds, particularly oligonucleotide compounds, which, in preferred embodiments, hybridize with nucleic acid molecules encoding eIF4E-BP2. Such compounds are shown herein to modulate the expression of eIF4E-BP2.

BACKGROUND OF THE INVENTION

Eukaryotic gene expression must be regulated such that cells can rapidly respond to a wide range of different conditions. The process of mRNA translation is one step at which gene expression is highly regulated. In response to hormones, growth factors, cytokines and nutrients, animal cells generally activate translation in preparation for the proliferative response. The rate of protein synthesis typically decreases under stressful conditions, such as oxidative or osmotic stress, DNA damage or nutrient withdrawal. Activation or suppression of mRNA translation occurs within minutes and control over this process is thought to be exerted at the initiation phase of protein synthesis (Rosenwald et al., *Oncogene*, 1999, 18, 2507-2517; Strudwick and Borden, *Differentiation*, 2002, 70, 10-22).

Translation initiation necessitates the coordinated activities of several eukaryotic initiation factors (eIFs), proteins which are classically defined by their cytoplasmic location and ability to regulate the initiation phase of protein synthesis. One of these factors, eukaryotic initiation factor 4E (eIF4E), is present in limiting amounts relative to other initiation factors and is one component of the eIF4F initiation complex, which is also comprised of the scaffold protein eIF4G and the RNA helicase eIF4A. In the cytoplasm, eIF4E catalyzes the rate-limiting step of cap-dependent protein synthesis by specifically binding to the 5' terminal 7-methyl GpppX cap structure present on nearly all mature cellular mRNAs, which serves to deliver the mRNAs to the eIF4F complex. Once bound, the eIF4F complex scans from the 5' to the 3' end of the cap, permitting the RNA helicase activity of eIF4A to resolve any secondary structure present in the 5' untranslated region (UTR), thus revealing the translation initiation codon and facilitating ribosome loading onto the mRNA (Graff and Zimmer, *Clin. Exp. Metastasis*, 2003, 20, 265-273; Strudwick and Borden, *Differentiation*, 2002, 70, 10-22).

eIF4E availability for incorporation into the eIF4E complex is regulated through phosphorylation as well as through the binding of inhibitory proteins. eIF4E is a phosphoprotein that is phosphorylated on serine 209 by the mitogen-activated protein kinase-interacting kinase Mnk1, as well as by protein kinase C (Flynn and Proud, *J. Biol. Chem.*, 1995, 270, 21684-21688; Wang et al., *J. Biol. Chem.*, 1998, 273, 9373-9377; Waskiewicz et al., *Embo J.* 1997, 16, 1909-1920). The inhibitory eIF4E-binding proteins 1 and 2 (eIF4E-BP1 and eIF4E-BP2) act as effective inhibitors of cap-dependent translation by competing with eIF4G for binding to the dorsal surface of eIF4E (Pause et al., Nature, 1994, 371, 762-767; Ptushkina et al., *Embo J.*, 1999, 18, 4068-4075). When complexed with bp1, eIF4E is not a substrate for phosphorylation by protein kinase C or Mnk1, indicating that dissociation of bp1 from eIF4E is a prerequisite for eIF4E phosphorylation (Wang et al., *J. Biol. Chem.*, 1998, 273, 9373-9377; Whalen et al., *J Biol Chem*, 1996, 271, 11831-11837). Phosphorylation of eIF4E increases its affinity for mRNA caps, thus elevating translation rates (Waskiewicz et al., *Mol. Cell Biol.*, 1999, 19, 1871-1880).

eIF4E-BP2 (also known as PHAS-II; 4EBP2; 4E-binding protein 2; EIF4EBP2) was cloned through use of the eIF4E protein in probing a cDNA expression library (Hu et al., *Proc Natl Acad Sci USA*, 1994, 91, 3730-3734; Pause et al., *Nature*, 1994, 371, 762-767). eIF4E-BP2 is ubiquitously expressed in human tissues, including heart, brain, placenta, lung, liver, kidney and spleen, as well as adipose tissue and skeletal muscle, the major insulin-responsive tissues (Hu et al., *Proc Natl Acad Sci USA*, 1994, 91, 3730-3734; Tsukiyama-Kohara et al., *Genomics*, 1996, 38, 353-363). The human gene maps to chromosome 10q21-q22 (Tsukiyama-Kohara et al., *Genomics*, 1996, 38, 353-363). The mouse bp1 gene consists of three exons, spans approximately 20 kb and maps to mouse chromosome 10 (Tsukiyama-Kohara et al., *Genomics*, 1996, 38, 353-363). The expression of eIF4E-BP2 does not appear to be altered in mice bearing a systemic disruption of bp1 (Blackshear et al., *J Biol Chem*, 1997, 272, 31510-31514).

Rather than preventing the binding of eIF4E to mRNA caps, eIF4E-BP2 prohibits the binding of eIF4E to eIF4G, thereby preventing formation of a complex that is necessary for efficient binding and proper positioning of the 40S ribosomal subunit on the target mRNA. When eIF4E-BP2 is bound to eIF4E, eIF4E does not serve as a substrate for phosphorylation by protein kinase C, suggesting that dissociation of eIF4E-BP2 from eIF4E is a prerequisite for phosphorylation of eIF4E (Whalen et al., *J Biol Chem*, 1996, 271, 11831-11837). The region to which eIF4E binds is a common motif shared by eIF4G and eIF4E-BP2, and point mutations in this region of eIF4E-BP2 abolish binding to eIF4E (Mader et al., *Mol Cell Biol*, 1995, 15, 4990-4997). Two conserved motifs are present in the eIF4E-BP2: the RAIP motif, which is found in the NH2-terminal region of EIF4E-BP2 and the TOS motif, which is formed by the last five amino acids of eIF4E-BP2 (Schalm and Blenis, *Curr Biol*, 2002, 12, 632-639; Tee and Proud, *Mol Cell Biol*, 2002, 22, 1674-1683).

Like eIF4E-BP1, insulin stimulates the phosphorylation of eIF4E-BP2 in cultured cells, which promotes the release of eIF4E-BP2 from eIF4E and allows for cap-dependent translation to proceed (Ferguson et al., *J Biol Chem*, 2003, 278, 47459-47465). Mitogen-activated protein kinase, the major insulin-stimulated kinase in rat adipocytes, can phosphorylate recombinant eIF4E-BP2 in vitro. However, treatment of 3T3-L1 rat adipocytes with rapamycin attenuates the effects of insulin on the phosphorylation of eIF4E-BP2, indicating that elements of the mTOR signaling pathway mediate the actions of insulin on eIF4E-BP2 (Lin and Lawrence, *J Biol*

Chem, 1996, 271, 30199-30204). Additionally, serine-65 of eIF4E-BP2 represents an ideal consensus site for phosphorylation by cyclic AMP-dependent protein kinase. In rat 3T3-L1 adipocytes, where insulin or epidermal growth factor markedly increased the phosphorylation of eIF4E-BP2, compounds that increase cyclic AMP decrease the amount of radiolabeled phosphate incorporated into eIF4E-BP2, and attenuate the effects of insulin on increasing the phosphorylation of eIF4E-BP2. Incubation of eIF4E-BP2 with the catalytic subunit of cyclic AMP-dependent protein kinase results in the rapid phosphorylation of eIF4E-BP2. Together, these data suggest that increasing cyclic AMP may selectively increase eIF4E-BP2 phosphorylation (Lin and Lawrence, *J Biol Chem*, 1996, 271, 30199-30204).

Induction of cellular differentiation and reduction of cellular proliferation are concomitant with a reduction in translation rates, as is observed in conjunction with differential regulation of eIF4E-BPs during human myeloid cell differentiation. When induced to differentiate into monocytes/macrophages, cells from the HL-60 promyelocytic leukemia cell or U-937 monoblastic cell lines exhibit a decrease in the phosphorylation of bp1. In contrast, when HL-60 cells are stimulated to differentiate into granulocytic cells, the amount of bp1 is decreased, whereas phosphorylation of bp1 is not affected. Conversely, eIF4E-BP2 levels are markedly increased. These findings suggest that translation machinery is differentially regulated during human myeloid cell differentiation (Grolleau et al., *J Immunol*, 1999, 162, 3491-3497).

The disregulation of signaling networks that promote cell proliferation is often observed in association with cancer (Lawrence and Abraham, *Trends Biochem Sci*, 1997, 22, 345-349). Expression of excess eIF4E-BP2 in cells transformed by eIF4E or v-src results in significant reversion of the transformed phenotype, demonstrating that eIF4E-BP2 can function as an inhibitor of cell growth (Rousseau et al., *Oncogene*, 1996, 13, 2415-2420).

The U.S. Pat. No. 6,410,715 describes a purified human nucleic acid sequence encoding a cellular component that binds to eIF4E comprising a coding sequence for the protein eIF4E-BP2, and discloses a method for screening a non-hormone agent potentially useful to treat a hormone disorder (Sonenberg et al., 2000).

Currently, there are no known therapeutic agents that target eIF4E-BP2. Consequently, there remains a long felt need for agents capable of effectively inhibiting eIF4E-BP2. Antisense technology is an effective means of reducing the expression of specific gene products and therefore is uniquely useful in a number of therapeutic, diagnostic and research applications for the modulation of eIF4E-BP2 expression.

The present invention provides compositions and methods for inhibiting eIF4E-BP2 expression.

SUMMARY OF THE INVENTION

The present invention is directed to antisense compounds, especially nucleic acid and nucleic acid-like oligomers, which are targeted to a nucleic acid encoding eIF4E-BP2, and which modulate the expression of eIF4E-BP2. Pharmaceutical and other compositions comprising the compounds of the invention are also provided. Further provided are methods of screening for modulators of eIF4E-BP2 and methods of modulating the expression of eIF4E-BP2 in cells, tissues or animals comprising contacting said cells, tissues or animals with one or more of the compounds or compositions of the invention. Methods of treating an animal, particularly a human, suspected of having or being prone to a disease or condition associated with expression of eIF4E-BP2, thereby in some instances delaying onset of said disease or condition, are also set forth herein. Such methods comprise administering a therapeutically or prophylactically effective amount of one or more of the compounds or compositions of the invention to the person in need of treatment.

DETAILED DESCRIPTION OF THE INVENTION

A. Overview of the Invention

The present invention employs antisense compounds, preferably oligonucleotides and similar species for use in modulating the function or effect of nucleic acid molecules encoding eIF4E-BP2. This is accomplished by providing oligonucleotides which specifically hybridize with one or more nucleic acid molecules encoding eIF4E-BP2. As used herein, the terms "target nucleic acid" and "nucleic acid molecule encoding eIF4E-BP2" have been used for convenience to encompass DNA encoding eIF4E-BP2, RNA (including pre-mRNA and mRNA or portions thereof) transcribed from such DNA, and also cDNA derived from such RNA. The hybridization of a compound of this invention with its target nucleic acid is generally referred to as "antisense". Consequently, the preferred mechanism believed to be included in the practice of some preferred embodiments of the invention is referred to herein as "antisense inhibition." Such antisense inhibition is typically based upon hydrogen bonding-based hybridization of oligonucleotide strands or segments such that at least one strand or segment is cleaved, degraded, or otherwise rendered inoperable. In this regard, it is presently preferred to target specific nucleic acid molecules and their functions for such antisense inhibition.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA. One preferred result of such interference with target nucleic acid function is modulation of the expression of eIF4E-BP2. In the context of the present invention, "modulation" and "modulation of expression" mean either an increase (stimulation) or a decrease (inhibition) in the amount or levels of a nucleic acid molecule encoding the gene, e.g., DNA or RNA. Inhibition is often the preferred form of modulation of expression and mRNA is often a preferred target nucleic acid.

In the context of this invention, "hybridization" means the pairing of complementary strands of oligomeric compounds. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

In the present invention the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated.

"Complementary," as used herein, refers to the capacity for precise pairing between two nucleobases of an oligomeric compound. For example, if a nucleobase at a certain position of an oligonucleotide (an oligomeric compound), is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligonucleotide and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an antisense compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). It is preferred that the antisense compounds of the present invention comprise at least 70%, or at least 75%, or at least 80%, or at least 85% sequence complementarity to a target region within the target nucleic acid, more preferably that they comprise at least 90% sequence complementarity and even more preferably comprise at least 95% or at least 99% sequence complementarity to the target region within the target nucleic acid sequence to which they are targeted. For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., *J. Mol. Biol.*, 1990, 215, 403-410; Zhang and Madden, *Genome Res.*, 1997, 7, 649-656).

Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). In some preferred embodiments, homology, sequence identity or complementarity, between the oligomeric and target is between about 50% to about 60%. In some embodiments, homology, sequence identity or complementarity, is between about 60% to about 70%. In preferred embodiments, homology, sequence identity or complementarity, is between about 70% and about 80%. In more preferred embodiments, homology, sequence identity or complementarity, is between about 80% and about 90%. In some preferred embodiments, homology, sequence identity or complementarity, is about 90%, about 92%, about 94%, about 95%, about 96%, about 97%, about 98%, about 99% or about 100%.

B. Compounds of the Invention

According to the present invention, antisense compounds include antisense oligomeric compounds, antisense oligonucleotides, siRNAs, external guide sequence (EGS) oligonucleotides, alternate splicers, primers, probes, and other oligomeric compounds which hybridize to at least a portion of the target nucleic acid. As such, these compounds may be introduced in the form of single-stranded, double-stranded, circular or hairpin oligomeric compounds and may contain structural elements such as internal or terminal bulges or loops. Once introduced to a system, the compounds of the invention may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded antisense compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While the preferred form of antisense compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

The first evidence that dsRNA could lead to gene silencing in animals came in 1995 from work in the nematode, *Caenorhabditis elegans* (Guo and Kempheus, *Cell*, 1995, 81, 611-620). Montgomery et al. have shown that the primary interference effects of dsRNA are posttranscriptional (Montgomery et al., *Proc. Natl. Acad. Sci. USA*, 1998, 95, 15502-15507). The posttranscriptional antisense mechanism defined in *Caenorhabditis elegans* resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., *Nature*, 1998, 391, 806-811). Recently, it has been shown that it is, in fact, the single-stranded RNA oligomers of antisense polarity of the dsRNAs which are the potent inducers of RNAi (Tijsterman et al., *Science*, 2002, 295, 694-697).

The antisense compounds of the present invention also include modified compounds in which a different base is present at one or more of the nucleotide positions in the compound. For example, if the first nucleotide is an adenosine, modified compounds may be produced which contain thymidine, guanosine or cytidine at this position. This may be done at any of the positions of the antisense compound. These compounds are then tested using the methods described herein to determine their ability to inhibit expression of eIF4E-BP2 mRNA.

In the context of this invention, the term "oligomeric compound" refers to a polymer or oligomer comprising a plurality of monomeric units. In the context of this invention, the term "oligonucleotide" refers to an oligomer or polymer of ribonucleic acid (RNA) or deoxyribonucleic acid (DNA) or mimetics, chimeras, analogs and homologs thereof. This term includes oligonucleotides composed of naturally occurring nucleobases, sugars and covalent internucleoside (backbone) linkages as well as oligonucleotides having non-naturally occurring portions which function similarly. Such modified or substituted oligonucleotides are often preferred over native forms because of desirable properties such as, for example, enhanced cellular uptake, enhanced affinity for a target nucleic acid and increased stability in the presence of nucleases.

While oligonucleotides are a preferred form of the antisense compounds of this invention, the present invention comprehends other families of antisense compounds as well, including but not limited to oligonucleotide analogs and mimetics such as those described herein.

The antisense compounds in accordance with this invention preferably comprise from about 8 to about 80 nucleobases (i.e. from about 8 to about 80 linked nucleosides). One of ordinary skill in the art will appreciate that the invention embodies compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length.

In one preferred embodiment, the antisense compounds of the invention are 13 to 50 nucleobases in length. One having ordinary skill in the art will appreciate that this embodies compounds of 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length.

In another preferred embodiment, the antisense compounds of the invention are 15 to 30 nucleobases in length. One having ordinary skill in the art will appreciate that this embodies compounds of 15, 16, 17, 18, 19, 20, 21, 22, 23, 24, 25, 26, 27, 28, 29, or 30 nucleobases in length.

Particularly preferred compounds are oligonucleotides from about 12 to about 50 nucleobases, even more preferably those comprising from about 15 to about 30 nucleobases.

Antisense compounds 13-80 nucleobases in length comprising a stretch of at least thirteen (13) consecutive nucleobases selected from within the illustrative antisense compounds are considered to be suitable antisense compounds as well.

While oligonucleotides are one form of antisense compound, the present invention comprehends other oligomeric antisense compounds, including but not limited to oligonucleotide mimetics such as are described below. The compounds in accordance with this invention can comprise from about 8 to about 80 nucleobases. In another embodiment, the oligonucleotide is about 10 to 50 nucleotides in length. In yet another embodiment, the oligonucleotide is 12 to 30 nucleotides in length. In yet another embodiment, the oligonucleotide is 12 to 24 nucleotides in length. In yet another embodiment, the oligonucleotide is 19 to 23 nucleotides in length. Some embodiments comprise at least an 8-nucleobase portion of a sequence of an oligomeric compound which inhibits expression of eIF4E-BP1. dsRNA or siRNA molecules directed to eIF4E-BP1, and their use in inhibiting eIF4E-BP1 mRNA expression, are also embodiments within the scope of the present invention.

The oligonucleotides of the present invention also include variants in which a different base is present at one or more of the nucleotide positions in the oligonucleotide. For example, if the first nucleotide is an adenosine, variants may be produced which contain thymidine (or uridine if RNA), guanosine or cytidine at this position. This may be done at any of the positions of the oligonucleotide. Thus, a 20-mer may comprise 60 variations (20 positions×3 alternates at each position) in which the original nucleotide is substituted with any of the three alternate nucleotides. These oligonucleotides are then tested using the methods described herein to determine their ability to inhibit expression of eIF4E-BP1 mRNA.

Exemplary preferred antisense compounds include oligonucleotide sequences that comprise at least the 13 consecutive nucleobases from the 5'-terminus of one of the illustrative preferred antisense compounds (the remaining nucleobases being a consecutive stretch of the same oligonucleotide beginning immediately upstream of the 5'-terminus of the antisense compound which is specifically hybridizable to the target nucleic acid and continuing until the oligonucleotide contains about 13 to about 80 nucleobases). Similarly preferred antisense compounds are represented by oligonucleotide sequences that comprise at least the 8 consecutive nucleobases from the 3'-terminus of one of the illustrative preferred antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains about 8 to about 80 nucleobases). It is also understood that preferred antisense compounds may be represented by oligonucleotide sequences that comprise at least 13 consecutive nucleobases from an internal portion of the sequence of an illustrative preferred antisense compound, and may extend in either or both directions until the oligonucleotide contains about 13 to about 80 nucleobases.

One having skill in the art armed with the preferred antisense compounds illustrated herein will be able, without undue experimentation, to identify further preferred antisense compounds.

C. Targets of the Invention

"Targeting" an antisense compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes eIF4E-BP2.

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding eIF4E-BP2, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the antisense compounds of the present invention.

The open reading frame (ORF) or "coding region," which is known in the art to refer to the region between the translation initiation codon and the translation termination codon, is also a region which may be targeted effectively. Within the context of the present invention, a preferred region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. It is also preferred to target the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also preferred target sites. mRNA transcripts produced via the process of splicing of two (or more) mRNAs from different gene sources are known as "fusion transcripts". It is also known that introns can be effectively targeted using antisense compounds targeted to, for example, DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also preferred target nucleic acids.

The locations on the target nucleic acid to which the preferred antisense compounds hybridize are hereinbelow referred to as "preferred target segments." As used herein the term "preferred target segment" is defined as at least an 8-nucleobase portion of a target region to which an active antisense compound is targeted. While not wishing to be bound by theory, it is presently believed that these target segments represent portions of the target nucleic acid which are accessible for hybridization.

While the specific sequences of certain preferred target segments are set forth herein, one of skill in the art will recognize that these serve to illustrate and describe particular embodiments within the scope of the present invention. Additional preferred target segments may be identified by one having ordinary skill.

Target segments 8-80 nucleobases in length comprising a stretch of at least eight (8) consecutive nucleobases selected from within the illustrative preferred target segments are considered to be suitable for targeting as well.

Target segments can include DNA or RNA sequences that comprise at least the 8 consecutive nucleobases from the 5'-terminus of one of the illustrative preferred target segments (the remaining nucleobases being a consecutive stretch of the same DNA or RNA beginning immediately upstream of the 5'-terminus of the target segment and continuing until the DNA or RNA contains about 8 to about 80 nucleobases). Similarly preferred target segments are represented by DNA or RNA sequences that comprise at least the 8 consecutive nucleobases from the 3'-terminus of one of the illustrative preferred target segments (the remaining nucleobases being a consecutive stretch of the same DNA or RNA beginning immediately downstream of the 3'-terminus of the target segment and continuing until the DNA or RNA contains about 8 to about 80 nucleobases). It is also understood that preferred antisense target segments may be represented by DNA or RNA sequences that comprise at least 8 consecutive nucleobases from an internal portion of the sequence of an illustrative preferred target segment, and may extend in either or both directions until the oligonucleotide contains about 8 to about 80 nucleobases. One having skill in the art armed with the preferred target segments illustrated herein will be able, without undue experimentation, to identify further preferred target segments.

Once one or more target regions, segments or sites have been identified, antisense compounds are chosen which are sufficiently complementary to the target, i.e., hybridize sufficiently well and with sufficient specificity, to give the desired effect.

The oligomeric antisense compounds may also be targeted to regions of the target nucleobase sequence (e.g., such as those disclosed in Example 13) comprising nucleobases 1-80, 81-160, 161-240, 241-320, 321-400, 401-480, 481-560, 561-640, 641-720, 721-800, 801-880, 881-960, 961-1040, 1041-1120, 1121-1200, 1201-1280, 1281-1360, 1361-1440, 1441-1520, 1521-1600, 1601-1680, 1681-1760, 1761-1840, 1841-1920, 1921-2000, 2001-2080, 2081-2160, 2161-2240, 2241-2320, 2321-2400, 2401-2480, 2481-2560, 2561-2640, 2641-2720, 2721-2782, or any combination thereof.

In one embodiment of the invention, the antisense compounds are targeted to a nucleic acid molecule encoding human eIF4E-BP2, for example nucleotides 146-165 in the 5' UTR, nucleotides 372-391, 420-520 or 544-593 in the coding region, nucleotides 589-608 in the stop codon region, nucleotides 623-766, 803-940, 1105-1599, 1868-1887, 1900-1919, 1962-1981, 2218-2242, 2377-2401, 2449-2490, 2536-2555 or 2578-2597 in the 3' UTR, all of SEQ ID NO: 4; nucleotides 8892-8911 and 11559-11937 in intron 1, and nucleotides 17941-17960 in the intron 1:exon 2 junction, all of SEQ ID NO: 25; nucleotides 2088-2107 in the 3' UTR of SEQ ID NO: 26; and nucleotides 697-716 in the 3'UTR of SEQ ID NO: 27, wherein said compound inhibits the expression of human eIF4E-BP2 mRNA.

In another embodiment of the invention, the antisense compounds are targeted to a nucleic acid molecule encoding mouse eIF4E-BP2, for example nucleotides 9-105 in the 5'UTR; nucleotides 132-480 in the coding region; nucleotides 473-492 in the stop codon region; and nucleotides 500-1175, 1222-1638, 1662-1780 in the 3' UTR, all of SEQ ID NO: 11; nucleotides 365-384 in the 3' UTR of SEQ ID NO: 107; and nucleotides 36-55 in the 5' UTR of SEQ ID NO: 108; wherein said compound inhibits the expression of mouse eIF4E-BP2 mRNA.

In a further embodiment of the invention, antisense compounds are targeted to a nucleic acid molecule encoding rat eIF4E-BP2, for example nucleotides 7-26 in the 5'UTR, nucleotides 7-151, 164-247, 270-313, or 303-388 in the coding region; nucleotides 390-409 in the stop codon region and nucleotides 402-490 in the 3' UTR, all of SEQ ID NO: 18; wherein said compound inhibits the expression of rat eIF4E-BP2 mRNA.

D. Screening and Target Validation

In a further embodiment, the "preferred target segments" identified herein may be employed in a screen for additional compounds that modulate the expression of eIF4E-BP2. "Modulators" are those compounds that decrease or increase the expression of a nucleic acid molecule encoding eIF4E-BP2 and which comprise at least an 8-nucleobase portion which is complementary to a preferred target segment. The screening method comprises the steps of contacting a preferred target segment of a nucleic acid molecule encoding eIF4E-BP2 with one or more candidate modulators, and selecting for one or more candidate modulators which decrease or increase the expression of a nucleic acid molecule encoding eIF4E-BP2. Once it is shown that the candidate modulator or modulators are capable of modulating (e.g. either decreasing or increasing) the expression of a nucleic acid molecule encoding eIF4E-BP2, the modulator may then be employed in further investigative studies of the function of eIF4E-BP2, or for use as a research, diagnostic, or therapeutic agent in accordance with the present invention.

The preferred target segments of the present invention may be also be combined with their respective complementary antisense compounds of the present invention to form stabilized double-stranded (duplexed) oligonucleotides.

Such double stranded oligonucleotide moieties have been shown in the art to modulate target expression and regulate translation as well as RNA processing via an antisense mechanism. Moreover, the double-stranded moieties may be subject to chemical modifications (Fire et al., *Nature*, 1998, 391, 806-811; Timmons and Fire, *Nature* 1998, 395, 854; Timmons et al., *Gene*, 2001, 263, 103-112; Tabara et al., *Science*, 1998, 282, 430-431; Montgomery et al., *Proc. Natl. Acad. Sci. USA*, 1998, 95, 15502-15507; Tuschl et al., *Genes Dev.*, 1999, 13, 3191-3197; Elbashir et al., *Nature*, 2001, 411, 494-498; Elbashir et al., *Genes Dev.* 2001, 15, 188-200). For example, such double-stranded moieties have been shown to inhibit the target by the classical hybridization of antisense strand of the duplex to the target, thereby triggering enzymatic degradation of the target (Tijsterman et al., *Science*, 2002, 295, 694-697).

The antisense compounds of the present invention can also be applied in the areas of drug discovery and target validation. The present invention comprehends the use of the compounds and preferred target segments identified herein in drug discovery efforts to elucidate relationships that exist between eIF4E-BP2 and a disease state, phenotype, or condition. These methods include detecting or modulating eIF4E-BP2 comprising contacting a sample, tissue, cell, or organism with the compounds of the present invention, measuring the nucleic acid or protein level of eIF4E-BP2 and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene

E. Kits, Research Reagents, Diagnostics, and Therapeutics

The antisense compounds of the present invention can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics, the compounds of the present invention, either alone or in combination with other compounds or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17-24; Celis, et al., *FEBS Lett.*, 2000, 480, 2-16), SAGE (serial analysis of gene expression) (Madden, et al., *Drug Discov. Today,* 2000, 5, 415-425), READS (restriction enzyme amplification of digested cDNAs) (Prashar and Weissman, *Methods Enzymol.*, 1999, 303, 258-72), TOGA (total gene expression analysis) (Sutcliffe, et al., *Proc. Natl. Acad. Sci. U.S.A.*, 2000, 97, 1976-81), protein arrays and proteomics (Celis, et al., *FEBS Lett.*, 2000, 480, 2-16; Jungblut, et al., *Electrophoresis,* 1999, 20, 2100-10), expressed sequence tag (EST) sequencing (Celis, et al., *FEBS Lett.*, 2000, 480, 2-16; Larsson, et al., *J. Biotechnol.*, 2000, 80, 143-57), subtractive RNA fingerprinting (SuRF) (Fuchs, et al., *Anal. Biochem.*, 2000, 286, 91-98; Larson, et al., *Cytometry,* 2000, 41, 203-208), subtractive cloning, differential display (DD) (Jurecic and Belmont, *Curr. Opin. Microbiol.*, 2000, 3, 316-21), comparative genomic hybridization (Carulli, et al., *J. Cell Biochem. Suppl.*, 1998, 31, 286-96), FISH (fluorescent in situ hybridization) techniques (Going and Gusterson, *Eur. J. Cancer,* 1999, 35, 1895-904) and mass spectrometry methods (To, *Comb. Chem. High Throughput Screen,* 2000, 3, 235-41).

The antisense compounds of the invention are useful for research and diagnostics, because these compounds hybridize to nucleic acids encoding eIF4E-BP2. For example, oligonucleotides that are shown to hybridize with such efficiency and under such conditions as disclosed herein as to be effective eIF4E-BP2 inhibitors will also be effective primers or probes under conditions favoring gene amplification or detection, respectively. These primers and probes are useful in methods requiring the specific detection of nucleic acid molecules encoding eIF4E-BP2 and in the amplification of said nucleic acid molecules for detection or for use in further studies of eIF4E-BP2. Hybridization of the antisense oligonucleotides, particularly the primers and probes, of the invention with a nucleic acid encoding eIF4E-BP2 can be detected by means known in the art. Such means may include conjugation of an enzyme to the oligonucleotide, radiolabelling of the oligonucleotide or any other suitable detection means. Kits using such detection means for detecting the level of eIF4E-BP2 in a sample may also be prepared.

The specificity and sensitivity of antisense is also harnessed by those of skill in the art for therapeutic uses. Antisense compounds have been employed as therapeutic moieties in the treatment of disease states in animals, including humans. Antisense oligonucleotide drugs, including ribozymes, have been safely and effectively administered to humans and numerous clinical trials are presently underway. It is thus established that antisense compounds can be useful therapeutic modalities that can be configured to be useful in treatment regimes for the treatment of cells, tissues and animals, especially humans.

For therapeutics, an animal, preferably a human, suspected of having a disease or disorder which can be treated by modulating the expression of eIF4E-BP2 is treated by administering antisense compounds in accordance with this invention. For example, in one non-limiting embodiment, the methods comprise the step of administering to the animal in need of treatment, a therapeutically effective amount of a eIF4E-BP2 inhibitor. The eIF4E-BP2 inhibitors of the present invention effectively inhibit the activity of the eIF4E-BP2 protein or inhibit the expression of the eIF4E-BP2 protein. In one embodiment, the activity or expression of eIF4E-BP2 in an animal is inhibited by about 10%. Preferably, the activity or expression of eIF4E-BP2 in an animal is inhibited by about 30%. More preferably, the activity or expression of eIF4E-BP2 in an animal is inhibited by 50% or more. Thus, the oligomeric antisense compounds modulate expression of eIF4E-BP2 mRNA by at least 10%, by at least 20%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100%.

For example, the reduction of the expression of eIF4E-BP2 may be measured in serum, adipose tissue, liver or any other body fluid, tissue or organ of the animal. Preferably, the cells contained within said fluids, tissues or organs being analyzed contain a nucleic acid molecule encoding eIF4E-BP2 protein and/or the eIF4E-BP2 protein itself.

The antisense compounds of the invention can be utilized in pharmaceutical compositions by adding an effective amount of a compound to a suitable pharmaceutically acceptable diluent or carrier. Use of the compounds and methods of the invention may also be useful prophylactically.

The compounds of the present inventions are inhibitors of eIF4E-BP2 expression. Thus, the compounds of the present invention are believed to be useful for treating metabolic diseases and conditions, particularly diabetes, obesity, hyperlipidemia or metabolic syndrome X. The compounds of the invention are also believed to be useful for preventing or delaying the onset of metabolic diseases and conditions, particularly diabetes, obesity, hyperlipidemia or metabolic syndrome X. Metabolic syndrome, metabolic syndrome X or simply Syndrome X refers to a cluster of risk factors that include obesity, dyslipidemia, particularly high blood triglycerides, glucose intolerance, high blood sugar and high blood pressure. Scott, C. L., Am J Cardiol. 2003 Jul. 3; 92(1A):35i-42i. The compounds of the invention have surprisingly been found to be effective for lowering blood glucose, including plasma glucose, and for lowering blood lipids, including serum lipids, particularly serum cholesterol and serum triglycerides. The compounds of the invention are therefore particularly useful for the treatment, prevention and delay of onset of type 2 diabetes, high blood glucose and hyperlipidemia.

F. Modifications

As is known in the art, a nucleoside is a base-sugar combination. The base portion of the nucleoside is normally a heterocyclic base sometimes referred to as a "nucleobase" or simply a "base". The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Internucleoside Linkages (Backbones)

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones containing a phosphorus atom therein include, for example, phosphorothioates, chiral phosphorothioates, phosphorodithioates, phosphotriesters, aminoalkylphosphotriamidonalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

Modified Sugar and Internucleoside Linkages-Mimetics

In other preferred antisense compounds, e.g., oligonucleotide mimetics, both the sugar and the internucleoside linkage (i.e. the backbone), of the nucleotide units are replaced with novel groups. The nucleobase units are maintained for hybridization with an appropriate target nucleic acid. One such compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science*, 1991, 254, 1497-1500.

Preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified Sugars

Modified antisense compounds may also contain one or more substituted sugar moieties. Preferred are antisense compounds, preferably antisense oligonucleotides, comprising one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3]_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta*, 1995, 78, 486-504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$, also described in examples hereinbelow.

Other preferred modifications include 2'-methoxy (2'-O—$CH_3$), 2'-aminopropoxy (2'-$OCH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Antisense compounds may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

A further preferred modification of the sugar includes Locked Nucleic Acids (LNAs) in which the 2'-hydroxyl group is linked to the 3' or 4' carbon atom of the sugar ring, thereby forming a bicyclic sugar moiety. The linkage is preferably a methylene (—$CH_2$—)$_n$ group bridging the 2' oxygen atom and the 4' carbon atom wherein n is 1 or 2. LNAs and preparation thereof are described in WO 98/39352 and WO 99/14226.

Natural and Modified Nucleobases

Antisense compounds may also include nucleobase (often referred to in the art as heterocyclic base or simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Conjugates

Another modification of the antisense compounds of the invention involves chemically linking to the antisense compound one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application PCT/US92/09196, filed Oct. 23, 1992, and U.S. Pat. No. 6,287,860, the entire disclosure of which are incorporated herein by reference. Conjugate moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Antisense compounds of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

Chimeric Compounds

It is not necessary for all positions in a given compound to be uniformly modified, and in fact more than one of the aforementioned modifications may be incorporated in a single compound or even at a single nucleoside within an oligonucleotide.

The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. Chimeric antisense oligonucleotides are thus a form of antisense compound. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL which cleaves both cellular and viral RNA. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

G. Formulations

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein in its entirety. For oligonucleotides, presently preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine. Sodium salts are presently believed to be more preferred.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogenous systems of one liquid dispersed in another in the form of droplets usually exceeding 0.1 μm in diameter. Emulsions may contain additional components in addition to the dispersed phases, and the active drug which may be present as a solution in either the aqueous phase, oily phase or itself as a separate phase. Microemulsions are included as an embodiment of the present invention. Emulsions and their uses are well known in the art and are further described in U.S. Pat. No. 6,287,860, which is incorporated herein in its entirety.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein in its entirety.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein in its entirety.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

One of skill in the art will recognize that formulations are routinely designed according to their intended use, i.e. route of administration.

Preferred formulations for topical administration include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters, pharmaceutically acceptable salts thereof, and their uses are further described in U.S. Pat. No. 6,287,860, which is incorporated herein in its entirety. Topical formulations are described in detail in U.S. patent application Ser. No. 09/315,298 filed on May 20, 1999, which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287, 860, which is incorporated herein in its entirety. Also preferred are combinations of penetration enhancers, for example, fatty acids/salts in combination with bile acids/ salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein in its entirety. Oral formulations for oligonucleotides and their preparation are described in detail in U.S. application Ser. No. 09/108,673 (filed Jul. 1, 1998), Ser. No. 09/315, 298 (filed May 20, 1999) and Ser. No. 10/071,822, filed Feb. 8, 2002, each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more oligomeric compounds and one or more other chemotherapeutic agents which function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of antisense compounds and other non-antisense drugs are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Alternatively, compositions of the invention may contain two or more antisense compounds targeted to different regions of the same nucleic acid target. Numerous examples of antisense compounds are known in the art. Two or more combined compounds may be used together or sequentially.

H. Dosing

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same. Each of the references, GenBank® accession numbers, and the like recited in the present application is incorporated herein by reference in its entirety.

EXAMPLES

Example 1

Design and Screening of Duplexed Antisense Compounds Targeting eIF4E-BP2

In accordance with the present invention, a series of nucleic acid duplexes comprising the antisense compounds of the present invention and their complements can be designed to target eIF4E-BP2. The nucleobase sequence of the antisense strand of the duplex comprises at least a 8-nucleobase portion of an oligonucleotide in Table 1. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini. Overhangs can range from 2 to 6 nucleobases and these nucleobases may or may not be complementary to the target nucleic acid. In another embodiment, the duplexes may have an overhang on only one terminus.

For example, a duplex comprising an antisense strand having the sequence CGAGAGGCGGACGGGACCG (SEQ ID NO: 260) and having a two-nucleobase overhang of deoxythymidine (dT) would have the following structure:

```
cgagaggcggacgggaccgTT    Antisense Strand (SEQ ID NO: 261)
|||||||||||||||||||
TTgctctccgcctgccctggc    Complement (SEQ ID NO: 262)
```

In another embodiment, a duplex comprising an antisense strand having the same sequence CGAGAGGCGGACGGGACCG (SEQ ID NO: 260) may be prepared with blunt ends (no single stranded overhang) as shown:

```
cgagaggcggacgggaccg      Antisense Strand (SEQ ID NO: 260)
|||||||||||||||||||
gctctccgcctgccctggc      Complement (SEQ ID NO: 263)
```

The RNA duplex can be unimolecular or bimolecular; i.e., the two strands can be part of a single molecule or may be separate molecules.

RNA strands of the duplex can be synthesized by methods disclosed herein or purchased from Dharmacon Research Inc., (Lafayette, Colo.). Once synthesized, the complementary strands (or alternatively, the complementary portions of a single RNA strand in the case of a unimolecular duplex) are annealed. The single strands are aliquoted and diluted to a concentration of 50 uM. Once diluted, 30 uL of each strand is combined with 15 uL of a 5× solution of annealing buffer. The final concentration of said buffer is 100 mM potassium acetate, 30 mM HEPES-KOH pH 7.4, and 2 mM magnesium acetate. The final volume is 75 uL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 uM. This solution can be stored frozen (−20° C.) and freeze-thawed up to 5 times.

Once prepared, the duplexed antisense compounds are evaluated for their ability to modulate eIF4E-BP2 expression.

When cells reached 80% confluency, they are treated with duplexed antisense compounds of the invention. For cells grown in 96-well plates, wells are washed once with 200 μL OPTI-MEM™-1 reduced-serum medium (Invitrogen Life Technologies, Carlsbad, Calif.) and then treated with 130 μL of OPTI-MEM™-1 containing 12 μg/mL LIPOFECTIN™ (Invitrogen Life Technologies, Carlsbad, Calif.) per 200 nM of the desired duplex antisense compound. After 5 hours of treatment, the medium is replaced with fresh medium. Cells are harvested 16 hours after treatment, at which time RNA is isolated and target reduction measured by real-time PCR.

Example 2

Oligonucleotide Isolation

After cleavage from the controlled pore glass solid support and deblocking in concentrated ammonium hydroxide at 55° C. for 12-16 hours, the oligonucleotides or oligonucleosides are recovered by precipitation out of 1 M NH OAc with >3 volumes of ethanol. Synthesized oligonucleotides were analyzed by electrospray mass spectroscopy (molecular weight determination) and by capillary gel electrophoresis and judged to be at least 70% full length material. The relative amounts of phosphorothioate and phosphodiester linkages obtained in the synthesis was determined by the ratio of correct molecular weight relative to the −16 amu product (+/−32+/−48). For some studies oligonucleotides were purified by HPLC, as described by Chiang et al., *J. Biol. Chem.* 1991, 266, 18162-18171. Results obtained with HPLC-purified material were similar to those obtained with non-HPLC purified material.

Example 3

Oligonucleotide Synthesis

96 Well Plate Format

Oligonucleotides were synthesized via solid phase P(III) phosphoramidite chemistry on an automated synthesizer capable of assembling 96 sequences simultaneously in a 96-well format. Phosphodiester internucleotide linkages were afforded by oxidation with aqueous iodine. Phosphorothioate internucleotide linkages were generated by sulfurization utilizing 3,H-1,2 benzodithiole-3-one 1,1′ dioxide (Beaucage Reagent) in anhydrous acetonitrile. Standard base-protected beta-cyanoethyl-diiso-propyl phosphoramidites were purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides were cleaved from support and deprotected with concentrated NH OH at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 4

Oligonucleotide Analysis

96-Well Plate Format

The concentration of oligonucleotide in each well was assessed by dilution of samples and UV absorption spectroscopy. The full-length integrity of the individual products was evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 5

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following cell types are provided for illustrative purposes, but other cell types can be routinely used, provided that the target is expressed in the cell type chosen. This can be readily determined by methods routine in the art, for example Northern blot analysis, ribonuclease protection assays, or real-time PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Invitrogen Life Technologies, Carlsbad, Calif.) supplemented with 10% fetal bovine serum (Invitrogen Life Technologies, Carlsbad, Calif.), penicillin 100 units per mL, and streptomycin 100 micrograms per mL (Invitrogen Life Technologies, Carlsbad, Calif.). Cells were routinely passaged by trypsinization and dilution when they reached 90% confluence. Cells were seeded into 96-well plates (e.g., Falcon-Primaria #353872, BD Biosciences, Bedford, Mass.) at a density of approximately 7000 cells/well for use in oligonucleotide transfection experiments and real-time PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Invitrogen Life Technologies, Carlsbad, Calif.) supplemented with 10% fetal bovine serum (Invitrogen Life Technologies, Carlsbad, Calif.), penicillin 100 units per mL, and streptomycin 100 micrograms per mL (Invitrogen Life Technologies, Carlsbad, Calif.). Cells were routinely passaged by trypsinization and dilution when they reached 90% confluence. Cells were seeded onto 96-well plates (e.g., Falcon-Primaria #353872, BD Biosciences, Bedford, Mass.) at a density of approximately 5000 cells per well for use in oligonucleotide transfection experiments and real-time PCR analysis.

NHDF Cells:

Human neonatal dermal fibroblast (NHDF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

b.END Cells:

The mouse brain endothelial cell line b.END was obtained from Dr. Werner Risau at the Max Plank Instittiute (Bad Nauheim, Germany). b.END cells were routinely cultured in DMEM, high glucose (Invitrogen Life Technologies, Carlsbad, Calif.) supplemented with 10% fetal bovine serum (Invitrogen Life Technologies, Carlsbad, Calif.). Cells were routinely passaged by trypsinization and dilution when they reached 90% confluence. Cells were seeded into 96-well plates (e.g., Falcon-Primaria #3872, BD Biosciences, Bedford, Mass.) at a density of approximately 3000 cells/well for use in oligonucleotide transfection experiments and real-time PCR analysis.

For Northern blotting or other analyses, cells may be seeded onto 100 mm or other standard tissue culture plates and treated similarly, using appropriate volumes of medium and oligonucleotide.

A10 Cells:

The rat aortic smooth muscle cell line A10 was obtained from the American Type Culture Collection (Manassas, Va.). A10 cells were routinely cultured in DMEM, high glucose (American Type Culture Collection, Manassas, Va.) supplemented with 10% fetal bovine serum (Invitrogen Life Technologies, Carlsbad, Calif.). Cells were routinely passaged by trypsinization and dilution when they reached 80% confluence. Cells were seeded into 96-well plates (e.g., Falcon-Primaria #3872, BD Biosciences, Bedford, Mass.) at a density of approximately 2500 cells/well for use in oligonucleotide transfection experiments and real-time PCR analysis.

For Northern blotting or other analyses, cells may be seeded onto 100 mm or other standard tissue culture plates and treated similarly, using appropriate volumes of medium and oligonucleotide.

EMT-6 Cells:

The mouse mammary epithelial carcinoma cell line EMT-6 was obtained from American Type Culture Collection (Manassus, Va.). They were grown in serial monolayer culture in DMEM, high glucose (Invitrogen Life Technologies, Carlsbad, Calif.) supplemented with 10% fetal bovine serum, (Invitrogen Life Technologies, Carlsbad, Calif.), 100 ug/ml penicillin and 100 ug/ml streptomycin (Invitrogen Life Technologies, Carlsbad, Calif.) in a humidified atmosphere of 90% air-10% $CO_2$ at 37° C. Cells were routinely passaged by trypsinization and dilution when they reached 85-90% confluencey. Cells were seeded into 96-well plates (e.g., Falcon-Primaria #353872, BD Biosciences, Bedford, Mass.) at a density of approximately 1000 cells/well for use in oligonucleotide transfection experiments and real-time PCR analysis.

Treatment with Antisense Compounds:

When cells reached 65-75% confluency, they were treated with oligonucleotide. Oligonucleotide was mixed with LIPOFECTIN™ (Invitrogen Life Technologies, Carlsbad, Calif.) in OPTI-MEM™-1 reduced-serum medium (Invitrogen Life Technologies, Carlsbad, Calif.) to achieve the desired concentration of oligonucleotide and a concentration of 2.5 to 3 ug/mL LIPOFECTIN™ per 100 nM oligonucleotide. For cells grown in 96-well plates, wells were washed once with 100 μL OPTI-MEM™-1 reduced-serum medium and then treated with 130 μL of the LIPOFECTIN™/oligonucleotide mixture. Cells are treated and data are obtained in duplicate or triplicate. After 4-7 hours of treatment at 37° C., the medium was replaced with fresh medium. Cells were harvested 16-24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is selected from either ISIS 13920 (TCCGTCATCGCTCCTCAGGG, SEQ ID NO: 1) which is targeted to human H-ras, or ISIS 18078, (GTGCGCGCGAGCCCGAAATC, SEQ ID NO: 2) which is targeted to human Jun-N-terminal kinase-2 (JNK2). Both controls are 2'-O-methoxyethyl gapmers (2'-O-methoxyethyls shown in bold) with a phosphorothioate backbone. For mouse or rat cells the positive control oligonucleotide is ISIS 15770, ATGCATTCTGCCCCCAAGGA, SEQ ID NO: 3, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-H-ras (for ISIS 13920), JNK2 (for ISIS 18078) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of c-H-ras, JNK2 or c-raf mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM.

Example 6

Analysis of Oligonucleotide Inhibition of eIF4E-BP2 Expression

Antisense modulation of eIF4E-BP2 expression can be assayed in a variety of ways known in the art. For example, eIF4E-BP2 mRNA levels can be quantitated by, e.g., Northern blot analysis, competitive polymerase chain reaction (PCR), or real-time PCR. Real-time quantitative PCR is presently preferred. RNA analysis can be performed on total cellular RNA or poly(A)+ mRNA. The preferred method of RNA analysis of the present invention is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of eIF4E-BP2 can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to eIF4E-BP2 can be identified and obtained from a variety of sources, such as the MSRS catalog of antibodies (Aerie Corporation, Birmingham, Mich.), or can be prepared via conventional monoclonal or polyclonal antibody generation methods well known in the art.

Example 7

Design of Phenotypic Assays for the Use of eIF4E-BP2 Inhibitors

Once eIF4E-BP2 inhibitors have been identified by the methods disclosed herein, the compounds are further investigated in one or more phenotypic assays, each having measurable endpoints predictive of efficacy in the treatment of a particular disease state or condition.
Phenotypic assays, kits and reagents for their use are well known to those skilled in the art and are herein used to investigate the role and/or association of eIF4E-BP2 in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with eIF4E-BP2 inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Measurement of the expression of one or more of the genes of the cell after treatment is also used as an indicator of the efficacy or potency of the eIF4E-BP2 inhibitors. Hallmark genes, or those genes suspected to be associated with a specific disease state, condition, or phenotype, are measured in both treated and untreated cells.

Example 8

RNA Isolation

Poly(A)+ mRNA isolation
Poly(A)+ mRNA was isolated according to Miura et al., (Clin. Chem., 1996, 42, 1758-1764). Other methods for poly (A)+ mRNA isolation are routine in the art. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C., was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.
Total RNA Isolation
Total RNA was isolated using an RNEASY 96™ kit and buffers purchased from Qiagen Inc. (Valencia, Calif.) following the manufacturer's recommended procedures. Briefly, for cells grown on 96-well plates, growth medium was removed from the cells and each well was washed with 200 µL cold PBS. 150 µL Buffer RLT was added to each well and the plate vigorously agitated for 20 seconds. 150 µL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 1 minute. 500 µL of Buffer RW1 was added to each well of the RNEASY 96™ plate and incubated for 15 minutes and the vacuum was again applied for 1 minute. An additional 500 µL of Buffer RW1 was added to each well of the RNEASY 96™ plate and the vacuum was applied for 2 minutes. 1 mL of Buffer RPE was then added to each well of the RNEASY 96™ plate and the vacuum applied for a period of 90 seconds. The Buffer RPE wash was then repeated and the vacuum was applied for an additional 3 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 140 µL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 9

Real-Time Quantitative PCR Analysis of eIF4E-BP2 mRNA Levels

Quantitation of eIF4E-BP2 mRNA levels was accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

Isolated RNA is subjected to a reverse transcriptase (RT) reaction, for the purpose of generating complementary DNA (cDNA), which is the substrate for the real-time PCR. Reverse transcriptase and real-time PCR reagents were obtained from Invitrogen Life Technologies, (Carlsbad, Calif.). The RT reaction and real-time PCR were carried out by adding 20 µL PCR cocktail (2.5×PCR buffer minus $MgCl_2$, 6.6 mM $MgCl_2$, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 µL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by real-time PCR are normalized using either the expression level of GAPDH, a gene whose expression is constant, or by quantifying total RNA using RiboGreen™ (Molecular Probes, Inc. Eugene, Oreg.). GAPDH expression is quantified by real time real-time PCR, by being run simultaneously with the target, multiplexing, or separately. Total RNA is quantified using RiboGreen™ RNA quantification reagent (Molecular Probes, Inc. Eugene, Oreg.). Methods of RNA quantification by RiboGreen™ are taught in Jones, L. J., et al, (Analytical Biochemistry, 1998, 265, 368-374).

In this assay, 170 µL of RiboGreen™ working reagent (RiboGreen™ reagent diluted 1:350 in 10 mM Tris-HCl, 1 mM EDTA, pH 7.5) is pipetted into a 96-well plate containing 30 µL purified, cellular RNA. The plate is read in a CytoFluor 4000 (PE Applied Biosystems) with excitation at 485 nm and emission at 530 nm.

Probes and primers to human eIF4E-BP2 were designed to hybridize to a human eIF4E-BP2 sequence, using published sequence information (GenBank® accession number NM_004096.3, incorporated herein as SEQ ID NO: 4). For human eIF4E-BP2 the PCR primers were:
forward primer: CCTCTAGTTTTGGGTGTGCATGT (SEQ ID NO: 5)
reverse primer: CCCATAGCAAGGCAGAATGG (SEQ ID NO: 6) and the PCR probe was: FAM-TGGAGTTTG-TAGTGGGTGGTTTGTAAAACTGG-TAMRA (SEQ ID NO: 7) where FAM is the fluorescent dye and TAMRA is the quencher dye. For human GAPDH the PCR primers were:

forward primer: GAAGGTGAAGGTCGGAGTC (SEQ ID NO: 8)
reverse primer: GAAGATGGTGATGGGATTTC (SEQ ID NO: 9) and the PCR probe was: 5' JOE-CAAGCTTCCCGT-TCTCAGCC-TAMRA 3' (SEQ ID NO: 10) where JOE is the fluorescent reporter dye and TAMRA is the quencher dye.

Probes and primers to mouse eIF4E-BP2 were designed to hybridize to a mouse eIF4E-BP2 sequence, using published sequence information (GenBank® accession number NM_010124.1, incorporated herein as SEQ ID NO: 11). For mouse eIF4E-BP2 the PCR primers were:
forward primer: GGCAAATTCAACGGCACAGT (SEQ ID NO: 12)
reverse primer: CGGACAGACGGACGATGAG (SEQ ID NO: 13) and the PCR probe was: FAM-CCTCCCAG-GTCTCTCGCCCT-TAMRA
(SEQ ID NO: 14) where FAM is the fluorescent reporter dye and TAMRA is the quencher dye. For mouse GAPDH the PCR primers were:
forward primer: GGCAAATTCAACGGCACAGT (SEQ ID NO: 15)
reverse primer: GGGTCTCGCTCCTGGAAGAT (SEQ ID NO: 16) and the PCR probe was: 5' JOE-AAGGC-CGAGAATGGGAAGCTTGTCATC-TAMRA 3' (SEQ ID NO: 17) where JOE is the fluorescent reporter dye and TAMRA is the quencher dye.

Probes and primers to rat eIF4E-BP2 were designed to hybridize to a rat eIF4E-BP2 sequence, using published sequence information (GenBank® accession number XM_215414.1, incorporated herein as SEQ ID NO: 18). For rat eIF4E-BP2 the PCR primers were:
forward primer: AGTGAACAACTTGAACAACCT-GAACA (SEQ ID NO: 19)
reverse primer: ACTGCAGCAGGGTCAGATGTC (SEQ ID NO: 20) and the PCR probe was: FAM-TCACGACAG-GAAGCACGCAGTTGG-TAMRA
(SEQ ID NO: 21) where FAM is the fluorescent reporter dye and TAMRA is the quencher dye. For rat GAPDH the PCR primers were:
forward primer: TGTTCTAGAGACAGCCGCATCTT (SEQ ID NO: 22)
reverse primer: CACCGACCTTCACCATCTTGT (SEQ ID NO: 23) and the PCR probe was: 5' JOE-TTGTGCAGTGC-CAGCCTCGTCTCA-TAMRA 3' (SEQ ID NO: 24) where JOE is the fluorescent reporter dye and TAMRA is the quencher dye.

Example 10

Northern Blot Analysis of eIF4E-BP2 mRNA Levels

Eighteen hours after antisense treatment, cell monolayers were washed twice with cold PBS and lysed in 1 mL RNA-ZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AM-RESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER UV Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect human eIF4E-BP2, a human eIF4E-BP2 specific probe was prepared by PCR using the forward primer CCTCTAGTTTTGGGTGTGCATGT (SEQ ID NO: 5) and the reverse primer CCCATAGCAAGGCAGAATGG (SEQ ID NO: 6). To normalize for variations in loading and transfer efficiency membranes were stripped and probed for human glyceraldehyde-3-phosphate dehydrogenase (GAPDH) RNA (Clontech, Palo Alto, Calif.).

To detect mouse eIF4E-BP2, a mouse eIF4E-BP2 specific probe was prepared by PCR using the forward primer AGAG-CAGCACAGGCTAAGACAGT (SEQ ID NO: 12) and the reverse primer CGGACAGACGGACGATGAG (SEQ ID NO: 13). To normalize for variations in loading and transfer efficiency membranes were stripped and probed for mouse glyceraldehyde-3-phosphate dehydrogenase (GAPDH) RNA (Clontech, Palo Alto, Calif.).

To detect rat eIF4E-BP2, a rat eIF4E-BP2 specific probe was prepared by PCR using the forward primer AGTGAA-CAACTTGAACAACCTGAACA (SEQ ID NO: 19) and the reverse primer ACTGCAGCAGGGTCAGATGTC (SEQ ID NO: 20). To normalize for variations in loading and transfer efficiency membranes were stripped and probed for rat glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 11

Antisense Inhibition of Human eIF4E-BP2 Expression by Chimeric Phosphorothioate Oligonucleotides Having 2'-MOE Wings and a Deoxy Gap In accordance with the present invention, a series of antisense compounds was designed to target different regions of the human eIF4E-BP2 RNA, using published sequences (GenBank® accession number NM_004096.3, incorporated herein as SEQ ID NO: 4, nucleotides 20714677 to 20740000 of the sequence with GenBank® accession number NT_008583.16, incorporated herein as SEQ ID NO: 25, GenBank® accession number AK057643.1, incorporated herein as SEQ ID NO: 26, GenBank® accession number AK001936.1, incorporated herein as SEQ ID NO: 27, and GenBank® accession number BF686401.1, incorporated herein as SEQ ID NO: 28). The compounds are shown in Table 1. "Target site" indicates the first (5'-most) nucleotide number on the particular target sequence to which the compound binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl (2'-MOE) nucleotides. The internucleoside (backbone) linkages are phosphorothioate (P=S) throughout the oligonucleotide. All cytidine residues are 5-methylcytidines. The compounds were analyzed for their effect on human eIF4E-BP2 mRNA levels by quantitative real-time PCR as described in other examples herein. Data are averages from two experiments in which A549 cells were treated with 75 nM of the antisense oligonucleotides of the present invention. SEQ ID NO: 2 was used as the control oligonucleotide in this assay. If present, "N. D." indicates "no data".

TABLE 1

Inhibition of human eIF4E-BP2 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 232773 | Coding | 4 | 420 | gccatgggagaattgcgacg | 68 | 29 |
| 232776 | Coding | 4 | 493 | tttggagtcttcaattaagg | 31 | 30 |
| 232777 | Coding | 4 | 498 | tctactttggagtcttcaat | 2 | 31 |
| 232828 | 3'UTR | 4 | 1962 | gtctgtagtcatcttaaaaa | 52 | 32 |
| 322947 | Coding | 4 | 501 | acttctactttggagtcttc | 60 | 33 |
| 347546 | Intron 1 | 25 | 1836 | tagaccgcaggagctgcgaa | 0 | 34 |
| 347547 | Intron 1 | 25 | 8892 | agtgattctcaaactgcaga | 38 | 35 |
| 347548 | Intron 1 | 25 | 11559 | tcttctgatccatggccacc | 52 | 36 |
| 347549 | Intron 1 | 25 | 11918 | tcagcactatctgttgaaaa | 39 | 37 |
| 347550 | Intron 1: Exon 2 junction | 25 | 16139 | attcgagttcctggaaaaca | 0 | 38 |
| 347551 | Exon 2: Intron 2 junction | 25 | 16324 | ttctcttaccaactgcatgt | 0 | 39 |
| 347552 | Intron 2: exon 3 junction | 25 | 17941 | gcatcatcccctagttagga | 27 | 40 |
| 347553 | 5'UTR | 4 | 146 | cctcaggcggacggaaaagc | 39 | 41 |
| 347554 | Coding | 4 | 332 | cgggcgtggtgcaatagtca | 63 | 42 |
| 347555 | Coding | 4 | 372 | attcgagttcctcccggtgt | 55 | 43 |
| 347556 | Coding | 4 | 392 | gaaactttctgtcataaatg | 0 | 44 |
| 347557 | Coding | 4 | 397 | caacagaaactttctgtcat | 15 | 45 |
| 347558 | Coding | 4 | 474 | gtgccagggctagtgactcc | 43 | 46 |
| 347559 | Coding | 4 | 526 | attgttcaagttgttcaaat | 0 | 47 |
| 347560 | Coding | 4 | 544 | tgcatgtttcctgtcgtgat | 59 | 48 |
| 347561 | Coding | 4 | 549 | ccaactgcatgtttcctgtc | 54 | 49 |
| 347562 | Coding | 4 | 558 | gcatcatcccaactgcatg | 54 | 50 |
| 347563 | Coding | 4 | 574 | gtccatctcgaactgagcat | 46 | 51 |
| 347564 | Stop Codon | 4 | 589 | gcaggagagtcagatgtcca | 47 | 52 |
| 347565 | 3'UTR | 4 | 623 | aagtatcagtgttgctgctt | 45 | 53 |
| 347566 | 3'UTR | 4 | 635 | tcaggtgcacacaagtatca | 43 | 54 |
| 347567 | 3'UTR | 4 | 734 | atcatttggcacccagagga | 54 | 55 |
| 347568 | 3'UTR | 4 | 747 | agctcatcttcccatcattt | 38 | 56 |
| 347569 | 3'UTR | 4 | 772 | acagggagaagaaatggtca | 13 | 57 |
| 347570 | 3'UTR | 4 | 803 | taacctgtttaactgggaag | 59 | 58 |
| 347571 | 3'UTR | 4 | 829 | cagaaatacagcaagggcct | 70 | 59 |
| 347572 | 3'UTR | 4 | 851 | ctctaagggctgcttagctc | 71 | 60 |
| 347573 | 3'UTR | 4 | 868 | agagttgaactgttttcctc | 78 | 61 |

TABLE 1-continued

Inhibition of human eIF4E-BP2 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 347574 | 3'UTR | 4 | 921 | caaaattacagggtatgagg | 63 | 62 |
| 347575 | 3'UTR | 4 | 1085 | aagaccccaagcccagactc | 9 | 63 |
| 347576 | 3'UTR | 4 | 1105 | atttcccctgctggtttta | 62 | 64 |
| 347577 | 3'UTR | 4 | 1130 | aagggaaagcagctctcttt | 70 | 65 |
| 347578 | 3'UTR | 4 | 1180 | agagttgcacaagctgtgct | 40 | 66 |
| 347579 | 3'UTR | 4 | 1217 | agtggacctcaaaacagtgt | 64 | 67 |
| 347580 | 3'UTR | 4 | 1303 | tctgcacaaatgcactaagt | 65 | 68 |
| 347581 | 3'UTR | 4 | 1350 | aaaactggttaccaagggct | 34 | 69 |
| 347582 | 3'UTR | 4 | 1357 | gaagagcaaaactggttacc | 27 | 70 |
| 347583 | 3'UTR | 4 | 1393 | ccagcaacgagatgcaagca | 65 | 71 |
| 347584 | 3'UTR | 4 | 1410 | agtacaagaggactctgcca | 56 | 72 |
| 347585 | 3'UTR | 4 | 1458 | tggtatggacctgctctagg | 51 | 73 |
| 347586 | 3'UTR | 4 | 1472 | gtgcctctattacttggtat | 48 | 74 |
| 347587 | 3'UTR | 4 | 1533 | ttcttaggcattatctgaca | 70 | 75 |
| 347588 | 3'UTR | 4 | 1541 | agcggtcattcttaggcatt | 59 | 76 |
| 347589 | 3'UTR | 4 | 1580 | acgactgagaccgggtactc | 67 | 77 |
| 347590 | 3'UTR | 4 | 1614 | acaactaccacaatgctcac | 0 | 78 |
| 347591 | 3'UTR | 4 | 1664 | attctgaaaatcaacttcaa | 0 | 79 |
| 347592 | 3'UTR | 4 | 1724 | tcccagcagccaaacaaagc | 0 | 80 |
| 347593 | 3'UTR | 4 | 1868 | atttgaaaaatggcctggta | 47 | 81 |
| 347594 | 3'UTR | 4 | 1892 | acacttcaggtatctttgat | 6 | 82 |
| 347595 | 3'UTR | 4 | 1900 | agataccaacacttcaggta | 49 | 83 |
| 347596 | 3'UTR | 4 | 1912 | acagatattctcagatacca | 0 | 84 |
| 347597 | 3'UTR | 4 | 2018 | atgtttaattaaaaagttgc | 0 | 85 |
| 347598 | 3'UTR | 4 | 2028 | acactggaagatgtttaatt | 17 | 86 |
| 347599 | 3'UTR | 4 | 2173 | cagttttacaaaccacccac | 0 | 87 |
| 347600 | 3'UTR | 4 | 2218 | aagaatgaggctttcttgaa | 47 | 88 |
| 347601 | 3'UTR | 4 | 2223 | cagaaaagaatgaggctttc | 34 | 89 |
| 347602 | 3'UTR | 4 | 2246 | tgaatgcaaaagcgaaaggg | 0 | 90 |
| 347603 | 3'UTR | 4 | 2301 | tcccgggattattatgctgc | 0 | 91 |
| 347604 | 3'UTR | 4 | 2377 | gaaattcccaggacaccagt | 63 | 92 |
| 347605 | 3'UTR | 4 | 2382 | aaccagaaattcccaggaca | 47 | 93 |
| 347606 | 3'UTR | 4 | 2389 | caaatccaaccagaaattcc | 0 | 94 |
| 347607 | 3'UTR | 4 | 2449 | ccaaatggcctgttactctc | 26 | 95 |
| 347608 | 3'UTR | 4 | 2471 | aacaaacaggtttcttcct | 40 | 96 |
| 347609 | 3'UTR | 4 | 2492 | cttttcatagttcaaaagaa | 19 | 97 |

TABLE 1-continued

Inhibition of human eIF4E-BP2 mRNA levels by chimeric
phosphorothioate oligonucleotides having 2'-MOE wings
and a deoxy gap

| ISIS # | REGION | TARGET SEQ ID NO | TARGET SITE | SEQUENCE | % INHIB | SEQ ID NO |
|---|---|---|---|---|---|---|
| 347610 | 3'UTR | 4 | 2536 | cagacatccttcctctcttt | 33 | 98 |
| 347611 | 3'UTR | 4 | 2564 | ttgtggcagaaaacagaaca | 0 | 99 |
| 347612 | 3'UTR | 4 | 2578 | aactattcacatttttgtgg | 62 | 100 |
| 347613 | 3'UTR | 4 | 2632 | tggagatccagcttattcct | 49 | 101 |
| 347614 | 3'UTR | 26 | 1189 | aagaatgaaaagcttcattc | 0 | 102 |
| 347615 | 3'UTR | 26 | 1336 | tttaaatccattcctcaccg | 0 | 103 |
| 347616 | 3'UTR | 26 | 2088 | ataactaatacaggtggaag | 41 | 104 |
| 347617 | 3'UTR | 27 | 697 | ggtcatctgaaatctctaaa | 45 | 105 |
| 347618 | 3'UTR | 28 | 464 | gcctcccacccttagaaagg | 2 | 106 |

As shown in Table 1, SEQ ID NOs 29, 30, 32, 33, 35, 36, 37, 40, 41, 42, 43, 46, 48, 49, 50, 51, 52, 53, 54, 55, 56, 58, 59, 60, 61, 62, 64, 65, 66, 67, 68, 69, 70, 71, 72, 73, 74, 75, 76, 77, 81, 83, 88, 89, 92, 93, 95, 96, 98, 100, 101, 104 and 105 demonstrated at least 25% inhibition of human eIF4E-BP2 expression in this assay and are therefore preferred. The target regions to which these preferred sequences are complementary are herein referred to as "preferred target segments" and are therefore preferred for targeting by compounds of the present invention. These preferred target segments are shown in Table 5. These sequences are shown to contain thymine (T) but one of skill in the art will appreciate that thymine (T) is generally replaced by uracil (U) in RNA sequences. The sequences represent the reverse complement of the preferred antisense compounds disclosed herein. "Target site" indicates the first (5'-most) nucleotide number on the particular target nucleic acid to which the oligonucleotide binds. Also shown in Table 5 is the species in which each of the preferred target segments was found.

SEQ ID NOs 29, 30, 31 and 32 are cross species oligonucleotides which are also complementary to the mouse eIF4E-BP2 nucleic acid target. SEQ ID NOs 29 and 33 are cross species oligonucleotides which are also complementary to rat eIF4E-BP2.

Example 12

Antisense Inhibition of Mouse eIF4E-BP2 Expression by Chimeric Phosphorothioate Oligonucleotides Having 2'-MOE Wings and a Deoxy Gap In accordance with the present invention, a second series of antisense compounds was designed to target different regions of the mouse eIF4E-BP2 RNA, using published sequences (GenBank® accession number NM_010124.1, incorporated herein as SEQ ID NO: 11, GenBank® accession number BI696127.1, incorporated herein as SEQ ID NO: 107, and GenBank® accession number BE332409.1, incorporated herein as SEQ ID NO: 108). The compounds are shown in Table 2. "Target site" indicates the first (5'-most) nucleotide number on the particular target nucleic acid to which the compound binds. All compounds in Table 2 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl (2'-MOE) nucleotides. The internucleoside (backbone) linkages are phosphorothioate (P=S) throughout the oligonucleotide. All cytidine residues are 5-methylcytidines. The compounds were analyzed for their effect on mouse eIF4E-BP2 mRNA levels by quantitative real-time PCR as described in other examples herein. Data, shown in Table 2, are averages from two experiments in which b.END cells were treated with 150 nM of the antisense oligonucleotides of the present invention. SEQ ID NO: 2 was used as the control oligonucleotide in this assay. If present, "N.D." indicates "no data".

TABLE 2

Inhibition of mouse eIF4E-BP2 mRNA levels in b.END
cells by chimeric phosphorothioate oligonucleotides
having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 232759 | 5'UTR | 11 | 9 | tctcaactcgcctgctctcg | 92 | 109 |
| 232760 | 5'UTR | 11 | 26 | ggctcctcacgctcggctct | 81 | 110 |

TABLE 2-continued

Inhibition of mouse eIF4E-BP2 mRNA levels in b.END cells by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 232761 | 5'UTR | 11 | 86 | tcgaggctttgtgcagcagc | 64 | 111 |
| 232762 | Coding | 11 | 132 | gctggtggctaccaccggcc | 49 | 112 |
| 232763 | Coding | 11 | 137 | gctgggctggtggctaccac | 72 | 113 |
| 232764 | Coding | 11 | 179 | gtcgctgatagccacggtgc | 77 | 114 |
| 232765 | Coding | 11 | 201 | agtcctgaggtagctgcgcg | 79 | 115 |
| 232766 | Coding | 11 | 211 | gtggtgcagtagtcctgagg | 81 | 116 |
| 232767 | Coding | 11 | 264 | cataaatgattcgtgttcct | 73 | 117 |
| 232768 | Coding | 11 | 269 | tcggtcataaatgattcgtg | 86 | 118 |
| 232769 | Coding | 11 | 274 | aactttcggtcataaatgat | 52 | 119 |
| 232770 | Coding | 11 | 281 | caacagaaactttcggtcat | 72 | 120 |
| 232771 | Coding | 11 | 286 | cggtccaacagaaactttcg | 84 | 121 |
| 232772 | Coding | 11 | 299 | gggagaattgcgacggtcca | 80 | 122 |
| 232773 | Coding | 11 | 304 | gccatgggagaattgcgacg | 83 | 29 |
| 232774 | Coding | 11 | 309 | tctgcgccatgggagaattg | 66 | 123 |
| 232775 | Coding | 11 | 354 | caggactggtgactccaggg | 87 | 124 |
| 232776 | Coding | 11 | 377 | tttggagtcttcaattaagg | 24 | 30 |
| 232777 | Coding | 11 | 382 | tctactttggagtcttcaat | 69 | 31 |
| 232778 | Coding | 11 | 388 | ttcacttctactttggagtc | 71 | 125 |
| 232779 | Coding | 11 | 449 | aaactgagcctcatccccaa | 89 | 126 |
| 232780 | Coding | 11 | 454 | atctcaaactgagcctcatc | 85 | 127 |
| 232781 | Coding | 11 | 461 | gatgtccatctcaaactgag | 73 | 128 |
| 232782 | Stop Codon | 11 | 473 | tggcagtagtcagatgtcca | 91 | 129 |
| 232783 | 3'UTR | 11 | 500 | ggctgctccacgaggcctcc | 90 | 130 |
| 232784 | 3'UTR | 11 | 521 | tgggccagtcaggtgcacac | 77 | 131 |
| 232785 | 3'UTR | 11 | 540 | ctgtacactgtgttcctact | 87 | 132 |
| 232786 | 3'UTR | 11 | 607 | atgtgatcagacagtgcaca | 67 | 133 |
| 232787 | 3'UTR | 11 | 614 | cgggaagatgtgatcagaca | 59 | 134 |
| 232788 | 3'UTR | 11 | 696 | ttcttctgtggactgtcagc | 44 | 135 |
| 232789 | 3'UTR | 11 | 787 | gtgctgcttggagactgccc | 54 | 136 |
| 232790 | 3'UTR | 11 | 798 | tacaagcagaggtgctgctt | 47 | 137 |
| 232791 | 3'UTR | 11 | 827 | ggcactaaacctccttcacc | 87 | 138 |
| 232792 | 3'UTR | 11 | 835 | acacaatgggcactaaacct | 68 | 139 |
| 232793 | 3'UTR | 11 | 845 | gagcccaggaacacaatggg | 61 | 140 |
| 232794 | 3'UTR | 11 | 900 | aatgtccccacatccagcg | 88 | 141 |
| 232795 | 3'UTR | 11 | 909 | ctgaggacaaatgtccccca | 81 | 142 |

TABLE 2-continued

Inhibition of mouse eIF4E-BP2 mRNA levels in b.END cells by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 232796 | 3'UTR | 11 | 927 | caggactgtgctccagagct | 78 | 143 |
| 232797 | 3'UTR | 11 | 934 | ggaggtacaggactgtgctc | 69 | 144 |
| 232798 | 3'UTR | 11 | 975 | gaggctgctgtcacatgtcc | 68 | 145 |
| 232799 | 3'UTR | 11 | 998 | aagccttcctcccagagaaa | 81 | 146 |
| 232800 | 3'UTR | 11 | 1020 | tatcacacccaagacaagac | 70 | 147 |
| 232801 | 3'UTR | 11 | 1030 | gatgatgagctatcacaccc | 83 | 148 |
| 232802 | 3'UTR | 11 | 1093 | cccttcaggagggcttaaaa | 70 | 149 |
| 232803 | 3'UTR | 11 | 1127 | cagacaggcaaagaccagct | 85 | 150 |
| 232804 | 3'UTR | 11 | 1156 | tgcctacgggatgcaggtag | 71 | 151 |
| 232805 | 3'UTR | 11 | 1204 | cttctgctctaaaagcagac | 1 | 152 |
| 232806 | 3'UTR | 11 | 1222 | caggccaaggtgttggcact | 57 | 153 |
| 232807 | 3'UTR | 11 | 1250 | gctgagagcaggctggactc | 66 | 154 |
| 232808 | 3'UTR | 11 | 1263 | tctcaggcagaccgctgaga | 54 | 155 |
| 232809 | 3'UTR | 11 | 1276 | gccctgatgtattctcagg | 72 | 156 |
| 232810 | 3'UTR | 11 | 1282 | tcagaggcccctgatgtatt | 51 | 157 |
| 232811 | 3'UTR | 11 | 1289 | gtcctcttcagaggcccctg | 89 | 158 |
| 232812 | 3'UTR | 11 | 1303 | tgcacggcggctcagtcctc | 69 | 159 |
| 232813 | 3'UTR | 11 | 1308 | ctggctgcacggcggctcag | 71 | 160 |
| 232814 | 3'UTR | 11 | 1327 | aaaaccatgaccccgaggc | 92 | 161 |
| 232815 | 3'UTR | 11 | 1340 | tacacctggttttaaaacca | 67 | 162 |
| 232816 | 3'UTR | 11 | 1355 | acacccaacgtaaggtacac | 86 | 163 |
| 232817 | 3'UTR | 11 | 1361 | tgcaggacacccaacgtaag | 85 | 164 |
| 232818 | 3'UTR | 11 | 1381 | aaactcaaggtatagtaacc | 73 | 165 |
| 232819 | 3'UTR | 11 | 1392 | aagtcgactttaaactcaag | 66 | 166 |
| 232820 | 3'UTR | 11 | 1399 | taagaggaagtcgactttaa | 75 | 167 |
| 232821 | 3'UTR | 11 | 1455 | ctgtgctgctctctcagcag | 21 | 168 |
| 232822 | 3'UTR | 11 | 1467 | cactgtcttagcctgtgctg | 90 | 169 |
| 232823 | 3'UTR | 11 | 1584 | tggaaaatggcccggtggaa | 82 | 170 |
| 232824 | 3'UTR | 11 | 1619 | tactaacatggaggcatct | 84 | 171 |
| 232825 | 3'UTR | 11 | 1646 | tgataaggagagactgatat | 28 | 172 |
| 232826 | 3'UTR | 11 | 1662 | taaaaggtctctcctctgat | 33 | 173 |
| 232827 | 3'UTR | 11 | 1668 | taaaaataaaaggtctctcc | 24 | 174 |
| 232828 | 3'UTR | 11 | 1682 | gtctgtagtcatcttaaaaa | 93 | 32 |
| 232829 | 3'UTR | 11 | 1699 | aacttatctaaaaataggtc | 30 | 175 |
| 232830 | 3'UTR | 11 | 1708 | tgtactgaaaacttatctaa | 74 | 176 |
| 232831 | 3'UTR | 11 | 1749 | atactggaagatgttttgtt | 70 | 177 |

TABLE 2-continued

Inhibition of mouse eIF4E-BP2 mRNA levels in b.END cells by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 232832 | 3'UTR | 11 | 1761 | ataaccttcccaatactgga | 82 | 178 |
| 232833 | 3'UTR | 107 | 365 | acagctcatggcaaggcaga | 79 | 179 |
| 232834 | 3'UTR | 107 | 437 | aactgctcttctatgtgtgg | 4 | 180 |
| 232835 | 3'UTR | 107 | 454 | tcgctgatagtctcttgaac | 0 | 181 |
| 232836 | 5'UTR | 108 | 36 | ggctcttcacgctcggctct | 73 | 182 |

As shown in Table 2, SEQ ID NOs 29, 31, 32, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 153, 154, 155, 156, 157, 158, 159, 160, 161, 162, 163, 164, 165, 166, 167, 169, 170, 171, 176, 177, 178, 179 and 182 demonstrated at least 44% inhibition of mouse eIF4E-BP2 expression in this experiment and are therefore preferred. The target regions to which these preferred sequences are complementary are herein referred to as "preferred target segments" and are therefore preferred for targeting by compounds of the present invention. These preferred target segments are shown in Table 4. These sequences are shown to contain thymine (T) but one of skill in the art will appreciate that thymine (T) is generally replaced by uracil (U) in RNA sequences. The sequences represent the reverse complement of the preferred antisense compounds disclosed herein. "Target site" indicates the first (5'-most) nucleotide number on the particular target nucleic acid to which the oligonucleotide binds. Also shown in Table 5 is the species in which each of the preferred target segments was found.

In a further embodiment, antisense oligonucleotides targeting mouse eIF4E-BP2 were tested in EMT-6 cells. The compounds were analyzed for their effect on mouse eIF4E-BP2 mRNA levels by quantitative real-time PCR as described in other examples herein. Data, shown in Table 3, are averages from two experiments in which EMT-6 cells were treated with 150 nM of the antisense oligonucleotides of the present invention. SEQ ID NO: 2 was used as the control oligonucleotide in this assay. If present, "N.D." indicates "no data".

TABLE 3

Inhibition of mouse eIF4E-BP2 mRNA levels in EMT-6 cells by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 232759 | 5'UTR | 11 | 9 | tctcaactcgcctgctctcg | 95 | 109 |
| 232760 | 5'UTR | 11 | 26 | ggctcctcacgctcggctct | 93 | 110 |
| 232761 | 5'UTR | 11 | 86 | tcgaggctttgtgcagcagc | 96 | 111 |
| 232762 | Coding | 11 | 132 | gctggtggctaccaccggcc | 88 | 112 |
| 232763 | Coding | 11 | 137 | gctgggctggtggctaccac | 94 | 113 |
| 232764 | Coding | 11 | 179 | gtcgctgatagccacggtgc | 95 | 114 |
| 232765 | Coding | 11 | 201 | agtcctgaggtagctgcgcg | 97 | 115 |
| 232766 | Coding | 11 | 211 | gtggtgcagtagtcctgagg | 93 | 116 |
| 232767 | Coding | 11 | 264 | cataaatgattcgtgttcct | 92 | 117 |
| 232768 | Coding | 11 | 269 | tcggtcataaatgattcgtg | 98 | 118 |
| 232769 | Coding | 11 | 274 | aactttcggtcataaatgat | 80 | 119 |
| 232770 | Coding | 11 | 281 | caacagaaactttcggtcat | 84 | 120 |
| 232771 | Coding | 11 | 286 | cggtccaacagaaactttcg | 97 | 121 |
| 232772 | Coding | 11 | 299 | gggagaattgcgacggtcca | 95 | 122 |
| 232773 | Coding | 11 | 304 | gccatgggagaattgcgacg | 96 | 29 |

TABLE 3-continued

Inhibition of mouse eIF4E-BP2 mRNA levels in EMT-6 cells by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 232774 | Coding | 11 | 309 | tctgcgccatgggagaattg | 93 | 123 |
| 232775 | Coding | 11 | 354 | caggactggtgactccaggg | 98 | 124 |
| 232776 | Coding | 11 | 377 | tttggagtcttcaattaagg | 73 | 30 |
| 232777 | Coding | 11 | 382 | tctactttggagtcttcaat | 85 | 31 |
| 232778 | Coding | 11 | 388 | ttcacttctactttggagtc | 93 | 125 |
| 232779 | Coding | 11 | 449 | aaactgagcctcatccccaa | 93 | 126 |
| 232780 | Coding | 11 | 454 | atctcaaactgagcctcatc | 92 | 127 |
| 232781 | Coding | 11 | 461 | gatgtccatctcaaactgag | 89 | 128 |
| 232782 | Stop Codon | 11 | 473 | tggcagtagtcagatgtcca | 95 | 129 |
| 232783 | 3'UTR | 11 | 500 | ggctgctccacgaggcctcc | 98 | 130 |
| 232784 | 3'UTR | 11 | 521 | tgggccagtcaggtgcacac | 95 | 131 |
| 232785 | 3'UTR | 11 | 540 | ctgtacactgtgttcctact | 98 | 132 |
| 232786 | 3'UTR | 11 | 607 | atgtgatcagacagtgcaca | 89 | 133 |
| 232787 | 3'UTR | 11 | 614 | cgggaagatgtgatcagaca | 75 | 134 |
| 232788 | 3'UTR | 11 | 696 | ttcttctgtggactgtcagc | 59 | 135 |
| 232789 | 3'UTR | 11 | 787 | gtgctgcttggagactgccc | 77 | 136 |
| 232790 | 3'UTR | 11 | 798 | tacaagcagaggtgctgctt | 87 | 137 |
| 232791 | 3'UTR | 11 | 827 | ggcactaaacctccttcacc | 91 | 138 |
| 232792 | 3'UTR | 11 | 835 | acacaatgggcactaaacct | 87 | 139 |
| 232793 | 3'UTR | 11 | 845 | gagcccaggaacacaatggg | 89 | 140 |
| 232794 | 3'UTR | 11 | 900 | aatgtcccccacatccagcg | 95 | 141 |
| 232795 | 3'UTR | 11 | 909 | ctgaggacaaatgtccccca | 92 | 142 |
| 232796 | 3'UTR | 11 | 927 | caggactgtgctccagagct | 95 | 143 |
| 232797 | 3'UTR | 11 | 934 | ggaggtacaggactgtgctc | 91 | 144 |
| 232798 | 3'UTR | 11 | 975 | gaggctgctgtcacatgtcc | 95 | 145 |
| 232799 | 3'UTR | 11 | 998 | aagccttcctcccagagaaa | 83 | 146 |
| 232800 | 3'UTR | 11 | 1020 | tatcacacccaagacaagac | 80 | 147 |
| 232801 | 3'UTR | 11 | 1030 | gatgatgagctatcacaccc | 91 | 148 |
| 232802 | 3'UTR | 11 | 1093 | cccttcaggagggcttaaaa | 85 | 149 |
| 232803 | 3'UTR | 11 | 1127 | cagacaggcaaagaccagct | 94 | 150 |
| 232804 | 3'UTR | 11 | 1156 | tgcctacgggatgcaggtag | 95 | 151 |
| 232805 | 3'UTR | 11 | 1204 | cttctgctctaaaagcagac | 36 | 152 |
| 232806 | 3'UTR | 11 | 1222 | caggccaaggtgttggcact | 83 | 153 |
| 232807 | 3'UTR | 11 | 1250 | gctgagagcaggctggactc | 82 | 154 |
| 232808 | 3'UTR | 11 | 1263 | tctcaggcagaccgctgaga | 74 | 155 |
| 232809 | 3'UTR | 11 | 1276 | gcccctgatgtattctcagg | 93 | 156 |

TABLE 3-continued

Inhibition of mouse eIF4E-BP2 mRNA levels in EMT-6 cells by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 232810 | 3'UTR | 11 | 1282 | tcagaggcccctgatgtatt | 86 | 157 |
| 232811 | 3'UTR | 11 | 1289 | gtcctcttcagaggccctg | 95 | 158 |
| 232812 | 3'UTR | 11 | 1303 | tgcacggcggctcagtcctc | 86 | 159 |
| 232813 | 3'UTR | 11 | 1308 | ctggctgcacggcggctcag | 91 | 160 |
| 232814 | 3'UTR | 11 | 1327 | aaaaccatgacccccgaggc | 96 | 161 |
| 232815 | 3'UTR | 11 | 1340 | tacacctggttttaaaacca | 93 | 162 |
| 232816 | 3'UTR | 11 | 1355 | acacccaacgtaaggtacac | 95 | 163 |
| 232817 | 3'UTR | 11 | 1361 | tgcaggacacccaacgtaag | 97 | 164 |
| 232818 | 3'UTR | 11 | 1381 | aaactcaaggtatagtaacc | 89 | 165 |
| 232819 | 3'UTR | 11 | 1392 | aagtcgactttaaactcaag | 96 | 166 |
| 232820 | 3'UTR | 11 | 1399 | taagaggaagtcgactttaa | 96 | 167 |
| 232821 | 3'UTR | 11 | 1455 | ctgtgctgctctctcagcag | 79 | 168 |
| 232822 | 3'UTR | 11 | 1467 | cactgtcttagcctgtgctg | 96 | 169 |
| 232823 | 3'UTR | 11 | 1584 | tggaaaatggcccggtggaa | 96 | 170 |
| 232824 | 3'UTR | 11 | 1619 | tactaacatgggaggcatct | 95 | 171 |
| 232825 | 3'UTR | 11 | 1646 | tgataaggagagactgatat | 60 | 172 |
| 232826 | 3'UTR | 11 | 1662 | taaaaggtctctcctctgat | 67 | 173 |
| 232827 | 3'UTR | 11 | 1668 | taaaaataaaaggtctctcc | 23 | 174 |
| 232828 | 3'UTR | 11 | 1682 | gtctgtagtcatcttaaaaa | 98 | 32 |
| 232829 | 3'UTR | 11 | 1699 | aacttatctaaaaataggtc | 69 | 175 |
| 232830 | 3'UTR | 11 | 1708 | tgtactgaaaacttatctaa | 97 | 176 |
| 232831 | 3'UTR | 11 | 1749 | atactggaagatgttttgtt | 89 | 177 |
| 232832 | 3'UTR | 11 | 1761 | ataaccttcccaatactgga | 95 | 178 |
| 232833 | 3'UTR | 107 | 365 | acagctcatggcaaggcaga | 96 | 179 |
| 232834 | 3'UTR | 107 | 437 | aactgctcttctatgtgtgg | 40 | 180 |
| 232835 | 3'UTR | 107 | 454 | tcgctgatagtctcttgaac | 23 | 181 |
| 232836 | 5'UTR | 108 | 36 | ggctcttcacgctcggctct | 88 | 182 |

As shown in Table 3, SEQ ID NOs 29, 30, 31, 32, 109, 110, 111, 112, 113, 114, 115, 116, 117, 118, 119, 120, 121, 122, 123, 124, 125, 126, 127, 128, 129, 130, 131, 132, 133, 134, 136, 137, 138, 139, 140, 141, 142, 143, 144, 145, 146, 147, 148, 149, 150, 151, 153, 154, 155, 156, 157, 158, 159, 160, 161, 162, 163, 164, 165, 166, 167, 168, 169, 170, 171, 173, 175, 176, 177, 178, 179 and 182 demonstrated at least 67% inhibition of mouse eIF4E-BP2 expression in this assay and are therefore preferred.

Example 13

Antisense Inhibition of Rat eIF4E-BP2 Expression by Chimeric Phosphorothioate Oligonucleotides Having 2'-MOE Wings and a Deoxy Gap In accordance with the present invention, a third series of antisense compounds was designed to target different regions of the rat eIF4E-BP2 RNA, using published sequences (GenBank® accession number XM_215414.1, incorporated herein as SEQ ID NO: 18). The compounds are shown in Table 4. "Target site" indicates the first (5'-most) nucleotide number on the particular target nucleic acid to which the compound binds. All compounds in Table 4 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl (2'-MOE) nucleotides. The internucleoside (backbone) linkages are phosphorothioate (P=S) throughout the oligonucleotide. All cytidine residues are 5-methylcytidines. The compounds were analyzed for their effect on rat eIF4E-BP2 mRNA levels by quantitative real-time PCR as described in other examples herein. Data, shown in Table 4, are averages from two experiments in which A10 cells were treated with 50 nM of the antisense oligonucleotides of the present invention. SEQ ID NO: 2 was used as the control oligonucleotide in this assay. If present, "N.D." indicates "no data".

TABLE 4

Inhibition of rat eIF4E-BP2 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 232773 | Coding | 11 | 304 | gccatgggagaattgcgacg | 90 | 29 |
| 322907 | 5'UTR | 18 | 7 | ggctcgtggctttgtgcagc | 48 | 183 |
| 322908 | Coding | 18 | 48 | tggtgtccaccaccggccga | 49 | 184 |
| 322909 | Coding | 18 | 57 | tggctgggctggtgtccacc | 65 | 185 |
| 322910 | Coding | 18 | 59 | tctggctgggctggtgtcca | 50 | 186 |
| 322911 | Coding | 18 | 71 | gaatggcgcggctctggctg | 65 | 187 |
| 322912 | Coding | 18 | 93 | ctaatagccacggtgcgtgt | 65 | 188 |
| 322913 | Coding | 18 | 97 | gtcgctaatagccacggtgc | 83 | 189 |
| 322914 | Coding | 18 | 102 | gctgcgtcgctaatagccac | 80 | 190 |
| 322915 | Coding | 18 | 114 | tgaggtagctgcgctgcgtc | 62 | 191 |
| 322916 | Coding | 18 | 116 | cctgaggtagctgcgctgcg | 68 | 192 |
| 322917 | Coding | 18 | 120 | tagtcctgaggtagctgcgc | 77 | 193 |
| 322918 | Coding | 18 | 122 | agtagtcctgaggtagctgc | 75 | 194 |
| 322919 | Coding | 18 | 125 | tgcagtagtcctgaggtagc | 80 | 195 |
| 322920 | Coding | 18 | 127 | ggtgcagtagtcctgaggta | 85 | 196 |
| 322921 | Coding | 18 | 130 | cgtggtgcagtagtcctgag | 78 | 197 |
| 322922 | Coding | 18 | 132 | ggcgtggtgcagtagtcctg | 74 | 198 |
| 322923 | Coding | 18 | 159 | ggtgttgtggagaacagcgt | 35 | 199 |
| 322924 | Coding | 18 | 164 | ctcccggtgttgtggagaac | 48 | 200 |
| 322925 | Coding | 18 | 168 | gttcctcccggtgttgtgga | 78 | 201 |
| 322926 | Coding | 18 | 193 | aaactttcggtcataaatga | 53 | 202 |
| 322927 | Coding | 18 | 195 | agaaactttcggtcataaat | 41 | 203 |
| 322928 | Coding | 18 | 197 | acagaaactttcggtcataa | 65 | 204 |
| 322929 | Coding | 18 | 198 | aacagaaactttcggtcata | 79 | 205 |
| 322930 | Coding | 18 | 201 | tccaacagaaactttcggtc | 83 | 206 |
| 322931 | Coding | 18 | 203 | ggtccaacagaaactttcgg | 83 | 207 |
| 322932 | Coding | 18 | 208 | gcgacggtccaacagaaact | 80 | 208 |
| 322933 | Coding | 18 | 210 | ttgcgacggtccaacagaaa | 76 | 209 |
| 322934 | Coding | 18 | 213 | gaattgcgacggtccaacag | 78 | 210 |
| 322935 | Coding | 18 | 215 | gagaattgcgacggtccaac | 75 | 211 |

TABLE 4-continued

Inhibition of rat eIF4E-BP2 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 322936 | Coding | 18 | 218 | tgggagaattgcgacggtcc | 36 | 212 |
| 322937 | Coding | 18 | 223 | cgccatgggagaattgcgac | 73 | 213 |
| 322938 | Coding | 18 | 225 | tgcgccatgggagaattgcg | 52 | 214 |
| 322939 | Coding | 18 | 228 | gtctgcgccatgggagaatt | 67 | 215 |
| 322940 | Coding | 18 | 250 | attgggcagatggcaaggtg | 33 | 216 |
| 322941 | Coding | 18 | 265 | ggtgactccagggatattgg | 35 | 217 |
| 322942 | Coding | 18 | 270 | ggactggtgactccagggat | 74 | 218 |
| 322943 | Coding | 18 | 275 | cgccaggactggtgactcca | 83 | 219 |
| 322944 | Coding | 18 | 292 | ggagtcttccattaaggcgc | 64 | 220 |
| 322945 | Coding | 18 | 294 | ttggagtcttccattaaggc | 66 | 221 |
| 322946 | Coding | 18 | 298 | tactttggagtcttccatta | 27 | 222 |
| 322947 | Coding | 18 | 303 | acttctactttggagtcttc | 68 | 33 |
| 322948 | Coding | 18 | 304 | cacttctactttggagtctt | 64 | 223 |
| 322949 | Coding | 18 | 308 | tgttcacttctactttggag | 87 | 224 |
| 322950 | Coding | 18 | 313 | caagttgttcacttctactt | 80 | 225 |
| 322951 | Coding | 18 | 316 | gttcaagttgttcacttcta | 82 | 226 |
| 322952 | Coding | 18 | 323 | tcaggttgttcaagttgttc | 83 | 227 |
| 322953 | Coding | 18 | 326 | tgttcaggttgttcaagttg | 84 | 228 |
| 322954 | Coding | 18 | 329 | gattgttcaggttgttcaag | 68 | 229 |
| 322955 | Coding | 18 | 332 | cgtgattgttcaggttgttc | 95 | 230 |
| 322956 | Coding | 18 | 335 | tgtcgtgattgttcaggttg | 95 | 231 |
| 322957 | Coding | 18 | 339 | ttcctgtcgtgattgttcag | 88 | 232 |
| 322958 | Coding | 18 | 341 | gcttcctgtcgtgattgttc | 95 | 233 |
| 322959 | Coding | 18 | 343 | gtgcttcctgtcgtgattgt | 92 | 234 |
| 322960 | Coding | 18 | 348 | actgcgtgcttcctgtcgtg | 97 | 235 |
| 322961 | Coding | 18 | 350 | caactgcgtgcttcctgtcg | 91 | 236 |
| 322962 | Coding | 18 | 353 | ccccaactgcgtgcttcctg | 85 | 237 |
| 322963 | Coding | 18 | 355 | atccccaactgcgtgcttcc | 48 | 238 |
| 322964 | Coding | 18 | 358 | ctcatccccaactgcgtgct | 83 | 239 |
| 322965 | Coding | 18 | 360 | gcctcatccccaactgcgtg | 90 | 240 |
| 322966 | Coding | 18 | 362 | gagcctcatccccaactgcg | 94 | 241 |
| 322967 | Coding | 18 | 364 | ctgagcctcatccccaactg | 89 | 242 |
| 322968 | Coding | 18 | 369 | tcaaactgagcctcatcccc | 50 | 243 |
| 322969 | Stop Codon | 18 | 390 | cagcagggtcagatgtccat | 81 | 244 |
| 322970 | 3'UTR | 18 | 402 | ccttcgacactgcagcaggg | 88 | 245 |
| 322971 | 3'UTR | 18 | 406 | gccgccttcgacactgcagc | 83 | 246 |

TABLE 4-continued

Inhibition of rat eIF4E-BP2 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 322972 | 3'UTR | 18 | 428 | gtgcacacgggccgtgtcag | 76 | 247 |
| 322973 | 3'UTR | 18 | 436 | ccagtcaggtgcacacgggc | 84 | 248 |
| 322974 | 3'UTR | 18 | 439 | ggtccagtcaggtgcacacg | 86 | 249 |
| 322975 | 3'UTR | 18 | 443 | tactggtccagtcaggtgca | 80 | 250 |
| 322976 | 3'UTR | 18 | 446 | tcctactggtccagtcaggt | 72 | 251 |
| 322977 | 3'UTR | 18 | 450 | gtgttcctactggtccagtc | 84 | 252 |
| 322978 | 3'UTR | 18 | 454 | cacggtgttcctactggtcc | 83 | 253 |
| 322979 | 3'UTR | 18 | 458 | tgtacacggtgttcctactg | 76 | 254 |
| 322980 | 3'UTR | 18 | 462 | tctctgtacacggtgttcct | 89 | 255 |
| 322981 | 3'UTR | 18 | 464 | cttctctgtacacggtgttc | 90 | 256 |
| 322982 | 3'UTR | 18 | 469 | tggagcttctctgtacacgg | 90 | 257 |
| 322983 | 3'UTR | 18 | 471 | actggagcttctctgtacac | 85 | 258 |

As shown in Table 4, SEQ ID NOs 183, 184, 185, 186, 187, 188, 189, 190, 191, 192, 193, 194, 195, 196, 197, 198, 200, 201, 202, 204, 205, 206, 207, 208, 209, 210, 211, 213, 214, 215, 218, 219, 220, 221, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257 and 258 demonstrated at least 48% inhibition of rat eIF4E-BP2 expression in this experiment and are therefore preferred. The target regions to which these preferred sequences are complementary are herein referred to as "preferred target segments" and are therefore preferred for targeting by compounds of the present invention. These sequences are shown to contain thymine (T) but one of skill in the art will appreciate that thymine (T) is generally replaced by uracil (U) in RNA sequences. The sequences represent the reverse complement of the preferred antisense compounds shown in tables above. "Target site" indicates the first (5'-most) nucleotide number on the particular target nucleic acid to which the compound binds.

"Preferred target segments," as described in Table 5 of U.S. Patent Application No. 60/538,752, filed Jan. 22, 2004, which is herein incorporated by reference in its entirety, have been found by experimentation to be open to, and accessible for, hybridization with the antisense compounds of the present invention, one of skill in the art will recognize or be able to ascertain, using no more than routine experimentation, further embodiments of the invention that encompass other compounds that specifically hybridize to these preferred target segments and consequently inhibit the expression of eIF4E-BP2.

According to the present invention, antisense compounds include antisense oligomeric compounds, antisense oligonucleotides, siRNAs, external guide sequence (EGS) oligonucleotides, alternate splicers, primers, probes, and other short oligomeric compounds which hybridize to at least a portion of the target nucleic acid.

Example 14

Western Blot Analysis of eIF4E-BP2 Protein Levels

Western blot analysis (immunoblot analysis) is carried out using standard methods. Cells are harvested 16-20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to eIF4E-BP2 is used, with a radiolabeled or fluorescently labeled secondary antibody directed against the primary antibody species. Bands are visualized using a PHOSPHORIMAGER™ (Molecular Dynamics, Sunnyvale Calif.).

Example 15

Reduction of Blood Glucose Levels in Ob/Ob Mice by Antisense Inhibition of eIF4E-BP2

Ob/ob mice have a mutation in the leptin gene which results in obesity and hyperglycemia. As such, these mice are a useful model for the investigation of obesity and diabetes and treatments designed to treat these conditions. In accordance with the present invention, compounds targeted to eIF4E-BP2 are tested in the ob/ob model of obesity and diabetes.

Seven-week old male C57Bl/6J-Lepr ob/ob mice (Jackson Laboratory, Bar Harbor, Me.) are fed a diet with a fat content of 10-15% and are subcutaneously injected with oligonucleotides at a dose of 25 mg/kg two times per week for 4 weeks. Saline-injected animals, leptin wildtype littermates (i.e. lean littermates) and ob/ob mice fed a standard rodent diet serve as controls. After the treatment period, mice are sacrificed and target levels are evaluated in liver, brown adipose tissue (BAT) and white adipose tissue (WAT). RNA isolation and target mRNA expression level quantitation are performed as described by other examples herein.

To assess the physiological effects resulting from antisense inhibition of target mRNA, the ob/ob mice that receive antisense oligonucleotide treatment are further evaluated at the end of the treatment period for serum lipids, serum free fatty acids, serum cholesterol, liver triglycerides, fat tissue triglycerides and liver enzyme levels. Hepatic steatosis, accumulation of lipids in the liver, is assessed by measuring the liver triglyceride content. Hepatic steatosis is assessed by routine histological analysis of frozen liver tissue sections stained with oil red O stain, which is commonly used to visualize lipid deposits, and counterstained with hematoxylin and eosin, to visualize nuclei and cytoplasm, respectively.

The effects of target inhibition on glucose and insulin metabolism are evaluated in the ob/ob mice treated with antisense oligonucleotides. Plasma glucose is measured at the start of the antisense oligonucleotide treatment and following two and four weeks of treatment. Both fed and fasted plasma glucose levels were measured. At start of study, the treatment groups of mice are chosen to have an average fed plasma glucose level of about 350 mg/dL. Plasma insulin is also measured at the beginning of the treatment, and following 2 weeks and 4 weeks of treatment. Glucose and insulin tolerance tests are also administered in fed and fasted mice. Mice receive intraperitoneal injections of either glucose or insulin, and the blood glucose and insulin levels are measured before the insulin or glucose challenge and at 15, 20 or 30 minute intervals for up to 3 hours.

In mice treated with ISIS 232828 (SEQ ID NO: 32), an antisense inhibitor of eIF4E-BP2, fed plasma glucose levels were approximately 355 mg/dL at week 0, 295 mg/dL at week 2 and 210 mg/dL at week 4. In contrast, mice treated with saline alone had fed plasma glucose levels of approximately 365 mg/dL at week 0, 425 mg/dL at week 2 and 410 mg/dL at week 4. Mice treated with a positive control oligonucleotide, ISIS 116847 (CTGCTAGCCTCTGGATTTGA; SEQ ID NO: 259), targeted to PTEN, had fed plasma glucose levels of approximately 360 mg/dL at week 0, 215 mg/dL at week 2 and 180 mg/dL at week 4.

Fasted plasma glucose was measured at week 3 of antisense treatment. Plasma glucose was approximately 330 mg/dL in saline treated mice, 245 mg/dL in mice treated with ISIS 232828 (inhibitor of eIF4E-BP2) and 195 mg/dL in mice treated with the positive control oligonucleotide, ISIS 116847.

At the end of the four week study, average liver weights were approximately 3.6 grams for saline treated mice, 3.2 grams for ISIS 232828-treated mice and 4.1 grams for positive control (ISIS 116847) treated mice. White adipose tissue weights were approximately 3.9 grams for saline treated mice, 3.8 grams for ISIS 232828-treated mice and 3.7 grams for positive control (ISIS 116847) treated mice.

At the end of the study, liver transaminases were found to be lower in mice treated with antisense to eIF4E-BP2 (ISIS 232828) than in mice treated with saline or the positive control oligonucleotide (ISIS 116847). AST levels were approximately 330 IU/L for saline treated mice, 110 IU/L for ISIS 232828-treated mice and 430 IU/L for ISIS 116847-treated mice. ALT levels were approximately 435 IU/L for saline treated mice, 140 IU/L for ISIS 232828-treated mice and 710 IU/L for ISIS 116847-treated mice.

Serum lipids were also measured at the end of the study. Cholesterol levels were approximately 230 mg/dL for saline treated mice, 210 mg/dL for ISIS 232828-treated mice and 260 mg/dL for ISIS 116847-treated mice. Triglycerides were approximately 135 mg/dL for saline treated mice, 80 mg/dL for ISIS 232828-treated mice and 110 mg/dL for ISIS 116847-treated mice.

eIF4E-BP2 mRNA levels in liver were measured at the end of study using RiboGreen™ RNA quantification reagent (Molecular Probes, Inc. Eugene, Oreg.) as taught in previous examples above. eIF4E-BP2 mRNA levels were reduced by approximately 90% in mice treated with ISIS 232828, compared to saline treatment. Target reduction in mice treated with ISIS 116847 was approximately 30%.

What is claimed is:

1. A pharmaceutical composition comprising a modified antisense compound 13 to 80 nucleobases in length targeted to a nucleic acid molecule encoding eIF4E-BP2, wherein said compound has at least an 8 nucleobase portion 100% complementary within nucleotides 1393-1599 of SEQ ID NO:4 encoding eIF4E-BP2, wherein said compound has at least 95% complementarity with SEQ ID NO:4 and inhibits the expression of eIF4E-BP2 mRNA; and a pharmaceutically acceptable carrier or diluent.

2. The pharmaceutical composition of claim 1, wherein said antisense compound is 13 to 50 nucleobases in length.

3. The pharmaceutical composition of claim 1, wherein said antisense compound is 15 to 30 nucleobases in length.

4. The pharmaceutical composition of claim 1, wherein said antisense compound comprises an oligonucleotide.

5. The pharmaceutical composition of claim 1, wherein said antisense compound comprises a DNA oligonucleotide.

6. The pharmaceutical composition of claim 1, wherein said antisense compound comprises an RNA oligonucleotide.

7. The pharmaceutical composition of claim 1, wherein said antisense compound is a double-stranded oligonucleotide.

8. The pharmaceutical composition of claim 1, wherein said antisense compound comprises a chimeric oligonucleotide.

9. The pharmaceutical composition of claim 1 wherein at least a portion of said compound hybridizes with RNA to form an oligonucleotide-RNA duplex.

10. The pharmaceutical composition of claim 1, wherein said antisense compound has at least 99% complementarity with said nucleic acid molecule encoding eIF4E-BP2.

11. The pharmaceutical composition of claim 1, wherein said antisense compound has at least one modified internucleoside linkage, sugar moiety, or nucleobase.

12. The pharmaceutical composition of claim 1, wherein said antisense compound has at least one 2'-O-methoxyethyl sugar moiety.

13. The pharmaceutical composition of claim 1, wherein said antisense compound has at least one phosphorothioate internucleoside linkage.

14. A modified antisense compound 13 to 80 nucleobases in length targeted to a nucleic acid molecule encoding eIF4E-BP2, wherein said antisense compound comprises at least a 13-nucleobase portion of SEQ ID NO: 72, 74, 75, 76, or 77 and inhibits the expression of eIF4E-BP2 mRNA.

15. The antisense compound of claim 14, wherein said antisense compound has a sequence selected from the group consisting of SEQ ID NOs: 72, 74, 75, 76, and 77.

16. The antisense compound of claim 15, wherein said antisense compound has the sequence of SEQ ID NO: 75.

17. The pharmaceutical composition of claim 1, wherein said antisense compound has 100% complementarity with said nucleic acid molecule encoding eIF4E-BP2.

18. The antisense compound of claim 14, wherein said antisense compound comprises at least a 13-nucleobase portion of SEQ ID NO: 72.

19. The antisense compound of claim 14, wherein said antisense compound comprises at least a 13-nucleobase portion of SEQ ID NO: 74.

20. The antisense compound of claim 14, wherein said antisense compound comprises at least a 13-nucleobase portion of SEQ ID NO: 75.

21. The antisense compound of claim 14, wherein said antisense compound comprises at least a 13-nucleobase portion of SEQ ID NO: 76.

22. The antisense compound of claim 14, wherein said antisense compound comprises at least a 13-nucleobase portion of SEQ ID NO: 77.

23. The antisense compound of claim 15, wherein said antisense compound has the sequence of SEQ ID NO: 72.

24. The antisense compound of claim 15, wherein said antisense compound has the sequence of SEQ ID NO: 74.

25. The antisense compound of claim 15, wherein said antisense compound has the sequence of SEQ ID NO: 76.

26. The antisense compound of claim 15, wherein said antisense compound has the sequence of SEQ ID NO: 77.

27. The antisense compound of claim 14, wherein said compound is a double-stranded oligonucleotide.

28. The antisense compound of claim 14, wherein said compound is a chimeric oligonucleotide.

29. The antisense compound of claim 15, wherein said compound is a double-stranded oligonucleotide.

30. The antisense compound of claim 15, wherein said compound is a chimeric oligonucleotide.

31. A modified antisense compound 13 to 80 nucleobases in length targeted to a nucleic acid molecule encoding eIF4E-BP2, wherein said antisense compound comprises at least a 13 nucleobase portion 100% complementary within SEQ ID NO: 71, 72, 73, 74, 75, 76, or 77 and inhibits the expression of eIF4E-BP2 mRNA.

32. The modified antisense compound of claim 31, wherein said antisense compound comprises at least a 13 nucleobase portion 100% complementary within SEQ ID NO: 71.

33. The modified antisense compound of claim 31, wherein said antisense compound comprises at least a 13 nucleobase portion 100% complementary within SEQ ID NO: 72.

34. The modified antisense compound of claim 31, wherein said antisense compound comprises at least a 13 nucleobase portion 100% complementary within SEQ ID NO: 73.

35. The modified antisense compound of claim 31, wherein said antisense compound comprises at least a 13 nucleobase portion 100% complementary within SEQ ID NO: 74.

36. The modified antisense compound of claim 31, wherein said antisense compound comprises at least a 13 nucleobase portion 100% complementary within SEQ ID NO: 75.

37. The modified antisense compound of claim 31, wherein said antisense compound comprises at least a 13 nucleobase portion 100% complementary within SEQ ID NO: 76.

38. The modified antisense compound of claim 31, wherein said antisense compound comprises at least a 13 nucleobase portion 100% complementary within SEQ ID NO: 77.

39. The antisense compound of claim 31, wherein said antisense compound has the sequence of SEQ ID NO: 71.

40. The antisense compound of claim 31, wherein said antisense compound has the sequence of SEQ ID NO: 73.

41. The antisense compound of claim 31, wherein said compound is a double-stranded oligonucleotide.

42. The antisense compound of claim 31, wherein said compound is a chimeric oligonucleotide.

43. A modified antisense compound 13 to 80 nucleobases in length targeted to a nucleic acid molecule encoding eIF4E-BP2, wherein said compound has at least an 8 nucleobase portion 100% complementary within nucleotides 1393-1599 of SEQ ID NO:4 encoding eIF4E-BP2, wherein said compound has at least 95% complementarity with SEQ ID NO:4 and inhibits the expression of eIF4E-BP2 mRNA, wherein said compound is a double-stranded oligonucleotide or comprises a chimeric oligonucleotide.

44. The modified antisense compound of claim 43, wherein said compound is a double-stranded oligonucleotide.

45. The modified antisense compound of claim 43, wherein said compound is a chimeric oligonucleotide.

46. The modified antisense compound of claim 43 which is 13 to 50 nucleobases in length.

47. The modified antisense compound of claim 43 which is 15 to 30 nucleobases in length.

48. The modified antisense compound of claim 43 comprising a DNA oligonucleotide.

49. The modified antisense compound of claim 43 comprising an RNA oligonucleotide.

50. The modified antisense compound of claim 43 wherein at least a portion of said compound hybridizes with RNA to form an oligonucleotide-RNA duplex.

51. The modified antisense compound of claim 43 having at least 99% complementarity with said nucleic acid molecule encoding eIF4E-BP2.

52. The modified antisense compound of claim 43 having 100% complementarity with said nucleic acid molecule encoding eIF4E-BP2.

53. The modified antisense compound of claim 43 having at least one modified internucleoside linkage, sugar moiety, or nucleobase.

54. The antisense compound of claim 43 having at least one 2'-O-methoxyethyl sugar moiety.

55. The antisense compound of claim 43 having at least one phosphorothioate internucleoside linkage.

* * * * *